US012421535B2

(12) United States Patent
Daviet et al.

(10) Patent No.: US 12,421,535 B2
(45) Date of Patent: Sep. 23, 2025

(54) BIOCHEMICALLY PRODUCED SANDALWOOD OIL

(71) Applicant: FIRMENICH SA, Satigny (CH)

(72) Inventors: Laurent Daviet, Satigny (CH); Yang Huang, Shanghai (CN); Vincent Harraca, Satigny (CH); Michel Schalk, Satigny (CH); Monica Bandera, Satigny (CH)

(73) Assignee: FIRMENICH SA, Satigny (CH)

( * ) Notice: Subject to any disclaimer, the term of this patent is extended or adjusted under 35 U.S.C. 154(b) by 91 days.

(21) Appl. No.: 17/757,752

(22) PCT Filed: Dec. 22, 2020

(86) PCT No.: PCT/EP2020/087658
§ 371 (c)(1),
(2) Date: Jun. 20, 2022

(87) PCT Pub. No.: WO2021/130241
PCT Pub. Date: Jul. 1, 2021

(65) Prior Publication Data
US 2024/0287560 A1 Aug. 29, 2024

(30) Foreign Application Priority Data

Dec. 23, 2019 (WO) ............... PCT/CN2019/127624
May 28, 2020 (EP) ................................... 20177072

(51) Int. Cl.
| | | |
|---|---|---|
| C12P 15/00 | (2006.01) |
| A01N 65/08 | (2009.01) |
| A01P 7/04 | (2006.01) |
| A61K 31/045 | (2006.01) |
| A61K 31/11 | (2006.01) |
| A61K 36/185 | (2006.01) |
| C11B 9/00 | (2006.01) |
| C11B 9/02 | (2006.01) |
| C12N 9/02 | (2006.01) |
| C12N 9/88 | (2006.01) |
| C12P 5/00 | (2006.01) |
| C12P 7/02 | (2006.01) |

(52) U.S. Cl.
CPC ............. *C12P 15/00* (2013.01); *A01N 65/08* (2013.01); *A01P 7/04* (2021.08); *A61K 31/045* (2013.01); *A61K 31/11* (2013.01); *A61K 36/185* (2013.01); *C11B 9/0003* (2013.01); *C11B 9/02* (2013.01); *C12N 9/0042* (2013.01); *C12N 9/0071* (2013.01); *C12N 9/88* (2013.01); *C12P 5/007* (2013.01); *C12P 7/02* (2013.01); *C12Y 106/02004* (2013.01); *C12Y 402/03082* (2013.01)

(58) Field of Classification Search
CPC . C12Y 114/00; C12Y 402/03081; C11B 9/02; C12N 9/0042
See application file for complete search history.

(56) References Cited

U.S. PATENT DOCUMENTS

| | | |
|---|---|---|
| 6,132,756 A | 10/2000 | Haque et al. |
| 6,368,639 B1 | 4/2002 | Farooqi et al. |
| 10,501,760 B2 | 12/2019 | Kumaran et al. |

FOREIGN PATENT DOCUMENTS

| | | |
|---|---|---|
| CN | 103796650 A | 5/2014 |
| CN | 105705478 A | 6/2016 |
| JP | 2017525395 A | 9/2017 |
| WO | 2011000026 A1 | 1/2011 |
| WO | 2014067007 A1 | 5/2014 |
| WO | 2015040197 A1 | 3/2015 |
| WO | 2016087179 A1 | 6/2016 |
| WO | 2017036863 A1 | 3/2017 |

OTHER PUBLICATIONS

Biosynthesis of Sandalwood Oil: Santalum album CYP76F Cytochromes P450 Produce Santalols and Bergamotol Maria L. Diaz-Chavez et al. (PLOS ONE Sep. 2013 | vol. 8 | Issue 9 | e75053 (Year: 2013).*
Fang et al., "Study on Enrichment of Characteristic Fragrance Components in Sandalwood Oil by Molecular Distillation", Tianjin Chemical Industry, 2016, pp. 50-52, 30(4).
Maria L. Diaz-Chavez et al, "Biosynthesis of Sandalwood Oil: Santalum album CYP76F Cytochromes P450 Produce Santalols and Bergamotol", Sep. 18, 2013 (Sep. 18, 2013), p. e75053, PLOS ONE, vol. 8, No. 9.
Pankaj P. Daramwar et al, "Preparative separation of [alpha]- and [beta]-santalenes and (Z)-[alpha]- and (Z)-[beta]-santalols using silver nitrate-impregnated silica gel medium pressure liquid chromatography and analysis of sandalwood oil", Analyst, Jan. 1, 2012 (Jan. 1, 2012), p. 4564, vol. 137, No. 19.
Nicolas Baldovini et al, "Phytochemistry of the heartwood from fragrant Santalum species: a review", Flavour and Fragrance Journal., Jan. 1, 2011 (Jan. 1, 2011), pp. 7-26, vol. 26, No. 1.
Ronald L Moy et al, "Sandalwood Album Oil as a Botanical Therapeutic in Dermatology", Oct. 1, 2017 (Oct. 1, 2017), pp. 34-39, vol. 10, No. 10.
Hyun Sik Roh et al, "Acaricidal and oviposition deterring effects of santalol identified in sandalwood oil against two-spotted spider mite,Koch (Acari: Tetranychidae)", Journal of Pest Science, Springer, Berlin, DE, Jul. 26, 2011 (Jul. 26, 2011), pp. 495-501, vol. 84, No. 4.

(Continued)

*Primary Examiner* — Tekchand Saidha
(74) *Attorney, Agent, or Firm* — Armstrong Teasdale LLP

(57) ABSTRACT

Described herein is a biochemically produced sandalwood oil including at least 85% santalol and bergamotol and 1% or less cis-lanceol, where the oil has one or more of the following features: i) 5% or less alpha-santalal; ii) 5% or less farnesol; and iii) 0.5% or less spirosantalol. Also described herein are a perfuming composition including the sandalwood oil and a perfuming consumer product including the sandalwood oil. Also described herein are a method of using the biochemically produced sandalwood oil as an antimicrobial and anti-inflammatory agent, and an arthropod control composition including the sandalwood oil.

17 Claims, 18 Drawing Sheets

Specification includes a Sequence Listing.

(56) References Cited

OTHER PUBLICATIONS

Gionata Scalcinati et al, "Dynamic control of gene expression inengineered for the production of plant sesquitepene-santalene in a fed-batch mode", Jan. 26, 2012 (Jan. 26, 2012), pp. 91-103, vol. 14, No. 2.
International Search Report and Written Opinion for corresponding PCT/EP2020/087658 mailed Apr. 16, 2021; 22 pages.

* cited by examiner

SEQUENCE LISTING

<160> NUMBER OF SEQ ID NOS: 7

<210> SEQ ID NO 1
<211> LENGTH: 1500
<212> TYPE: DNA
<213> ORGANISM: Santalum album

<400> SEQUENCE: 1

| | | | | | |
|---|---|---|---|---|---|
| atggcactgt | tgttggcggt | tttctggagc | gctttgatta | ttctggttag | catcttattg | 60 |
| cgtcgtcgtc | aaaaacgcaa | caatttgcca | ccgggcccac | cggccctgcc | gatcatcggt | 120 |
| aacattcaca | ttctgggcac | cctgccgcac | cagagcctgt | acaatctggc | gaagaagtac | 180 |
| ggtccgatca | tgtccatgcg | tttgggcttg | gttccggcgg | tggtcatcag | cagcccggaa | 240 |
| gcggccgagc | tggtcctgaa | aacccacgac | atcgttttg | cttctcgccc | tcgtctgcaa | 300 |
| gttgcagatt | actttcacta | tggcaccaaa | ggcgtgattc | tgaccgaata | tggtacctac | 360 |
| tggcgtaaca | tgcgtcgcct | gtgcacggtc | aaactgctga | acaccgttaa | gattgatagc | 420 |
| tttgcaggca | cccgcaagaa | agaagtcgct | agcttcgttc | agagcctgaa | agaagcaagc | 480 |
| gtggcgcaca | aaatggttaa | cctgtccgca | cgcgtcgcta | atgttattga | aatatggtt | 540 |
| tgtctgatgg | ttattggtag | atcgtctgac | gagcgtttca | agctgaaaga | agtgatccaa | 600 |
| gaagcggcac | agctggcggg | tgccttcaat | attggtgact | atgtcccgtt | tctgatgccg | 660 |
| ctggatctgc | agggcctgac | tcgccgtatc | aagagcggta | gcaaggcatt | cgatgacatc | 720 |
| ctcgaggtca | ttatcgacga | gcatgtgcaa | gacattaaag | atcatgacga | tgagcagcat | 780 |
| ggtgacttca | tcgacgtgct | gctggcgatg | atgaataagc | cgatggattc | tcgtgagggt | 840 |
| ctgtccatca | ttgatcgcac | gaacattaaa | gcgatcctgg | tggatatgat | cggtgccgcg | 900 |
| atggacacga | gcaccagcgg | tgtggagtgg | gcgatttcgg | agctgattaa | gcatcctcgt | 960 |
| gtcatgaaga | aactgcaaga | cgaagtgaaa | accgtaatcg | gtatgaaccg | catggtggaa | 1020 |
| gaagcggatc | tgccgaaact | gccgtacctg | gacatggttg | tcaaggaaac | gatgcgtctg | 1080 |
| catccgccag | gcccgctgct | ggtgccgcgt | gaaagcatgg | aagatattac | gatcaacggt | 1140 |
| tactatatcc | cgaagaaatc | ccgcattatt | gtgaatgcat | gggcgatcgg | ccgtgacacc | 1200 |
| aacgcctgga | gcaataatgc | gcacgagttt | ttccctgagc | gttttatgag | ctctaacgtt | 1260 |
| gatctgcaag | gccaggactt | ccagctgatc | ccgttcggta | gcggtcgtcg | cggttgtccg | 1320 |
| ggcatgcgtc | tgggtctgac | gacggtccgc | ttggtgctgg | cccaactgat | tcactgcttc | 1380 |
| gacctggagc | ttccgaaggg | caccgtcgcg | actgacctgg | atatgagcga | aagtttggt | 1440 |
| ctggcaatgc | cgcgtgcgca | gcacttactg | gcctttccga | cctaccgtct | ggagagctaa | 1500 |

<210> SEQ ID NO 2
<211> LENGTH: 499
<212> TYPE: PRT
<213> ORGANISM: Santalum album

<400> SEQUENCE: 2

Met Ala Leu Leu Leu Ala Val Phe Trp Ser Ala Leu Ile Ile Leu Val
1               5                   10                  15

Ser Ile Leu Leu Arg Arg Arg Gln Lys Arg Asn Asn Leu Pro Pro Gly
            20                  25                  30

Pro Pro Ala Leu Pro Ile Ile Gly Asn Ile His Ile Leu Gly Thr Leu
        35                  40                  45

Pro His Gln Ser Leu Tyr Asn Leu Ala Lys Lys Tyr Gly Pro Ile Met
    50                  55                  60

-continued

```
Ser Met Arg Leu Gly Leu Val Pro Ala Val Ile Ser Ser Pro Glu
 65                  70                  75                  80

Ala Ala Glu Leu Val Leu Lys Thr His Asp Ile Val Phe Ala Ser Arg
                 85                  90                  95

Pro Arg Leu Gln Val Ala Asp Tyr Phe His Tyr Gly Thr Lys Gly Val
                100                 105                 110

Ile Leu Thr Glu Tyr Gly Thr Tyr Trp Arg Asn Met Arg Arg Leu Cys
                115                 120                 125

Thr Val Lys Leu Leu Asn Thr Val Lys Ile Asp Ser Phe Ala Gly Thr
    130                 135                 140

Arg Lys Lys Glu Val Ala Ser Phe Val Gln Ser Leu Lys Glu Ala Ser
145                 150                 155                 160

Val Ala His Lys Met Val Asn Leu Ser Ala Arg Val Ala Asn Val Ile
                165                 170                 175

Glu Asn Met Val Cys Leu Met Val Ile Gly Arg Ser Ser Asp Glu Arg
                180                 185                 190

Phe Lys Leu Lys Glu Val Ile Gln Glu Ala Ala Gln Leu Ala Gly Ala
                195                 200                 205

Phe Asn Ile Gly Asp Tyr Val Pro Phe Leu Met Pro Leu Asp Leu Gln
    210                 215                 220

Gly Leu Thr Arg Arg Ile Lys Ser Gly Ser Lys Ala Phe Asp Asp Ile
225                 230                 235                 240

Leu Glu Val Ile Ile Asp Glu His Val Gln Asp Ile Lys Asp His Asp
                245                 250                 255

Asp Glu Gln His Gly Asp Phe Ile Asp Val Leu Leu Ala Met Met Asn
                260                 265                 270

Lys Pro Met Asp Ser Arg Glu Gly Leu Ser Ile Ile Asp Arg Thr Asn
                275                 280                 285

Ile Lys Ala Ile Leu Val Asp Met Ile Gly Ala Ala Met Asp Thr Ser
    290                 295                 300

Thr Ser Gly Val Glu Trp Ala Ile Ser Glu Leu Ile Lys His Pro Arg
305                 310                 315                 320

Val Met Lys Lys Leu Gln Asp Glu Val Lys Thr Val Ile Gly Met Asn
                325                 330                 335

Arg Met Val Glu Glu Ala Asp Leu Pro Lys Leu Pro Tyr Leu Asp Met
                340                 345                 350

Val Val Lys Glu Thr Met Arg Leu His Pro Pro Gly Pro Leu Leu Val
                355                 360                 365

Pro Arg Glu Ser Met Glu Asp Ile Thr Ile Asn Gly Tyr Tyr Ile Pro
    370                 375                 380

Lys Lys Ser Arg Ile Ile Val Asn Ala Trp Ala Ile Gly Arg Asp Thr
385                 390                 395                 400

Asn Ala Trp Ser Asn Asn Ala His Glu Phe Phe Pro Glu Arg Phe Met
                405                 410                 415

Ser Ser Asn Val Asp Leu Gln Gly Gln Asp Phe Gln Leu Ile Pro Phe
                420                 425                 430

Gly Ser Gly Arg Arg Gly Cys Pro Gly Met Arg Leu Gly Leu Thr Thr
                435                 440                 445

Val Arg Leu Val Leu Ala Gln Leu Ile His Cys Phe Asp Leu Glu Leu
    450                 455                 460

Pro Lys Gly Thr Val Ala Thr Asp Leu Asp Met Ser Glu Lys Phe Gly
465                 470                 475                 480
```

Leu Ala Met Pro Arg Ala Gln His Leu Leu Ala Phe Pro Thr Tyr Arg
          485                 490                 495

Leu Glu Ser

<210> SEQ ID NO 3
<211> LENGTH: 2133
<212> TYPE: DNA
<213> ORGANISM: Mentha piperita

<400> SEQUENCE: 3

| | | |
|---|---|---|
| atggaaccta gctctcagaa actgtctccg ttggaatttg ttgctgctat cctgaagggc | 60 |
| gactacagca gcggtcaggt tgaaggtggt ccaccgccag gtctggcagc tatgttgatg | 120 |
| gaaaataagg atttggtgat ggttctgacg acgtccgtgg cagtcctgat cggctgtgtc | 180 |
| gtggtcctgg catggcgtcg tgcggcaggt agcggtaagt acaagcaacc tgaactgcct | 240 |
| aaactggtgg tcccgaaagc agccgaaccg gaggaggcag aggatgataa aaccaagatc | 300 |
| agcgtgtttt tcggcaccca aaccggtacg gcagaaggtt tcgcgaaggc ttttgttgaa | 360 |
| gaggccaagg cgcgttatca gcaggcccgt ttcaaagtta tcgacctgga cgactatgcg | 420 |
| gcagacgatg acgagtacga agagaaactg aagaaggaaa acttggcatt cttcttcttg | 480 |
| gcgtcctacg gtgacggcga gccgacggac aacgcggcac gcttttacaa atggtttacg | 540 |
| gagggtaagg accgtggtga atggctgaac aatctgcagt acggcgtttt tggtctgggt | 600 |
| aaccgtcaat atgagcattt caataagatc gccattgtcg tcgatgatct gatcttcgag | 660 |
| caaggtggca gaagctggt tccggtgggt ctgggtgacg atgaccagtg cattgaggat | 720 |
| gatttttgcgg cgtggcgtga actggtctgg ccggaactgg ataaactgct gcgtaacgaa | 780 |
| gacgacgcta ccgtggcaac cccgtacagc gccgctgtgc tgcaataccg cgtggttttc | 840 |
| cacgatcaca ttgacggcct gattagcgaa acggtagcc gaacggtca tgctaatggc | 900 |
| aataccgtgt acgatgcgca caccccgtgc cgtagcaacg tcgcggtcaa gaaggaattg | 960 |
| catactccgg cgagcgatcg cagctgcacc cacctggaat ttaacattag cggtaccggc | 1020 |
| ctgatgtacg agacgggtga ccacgtcggt gtgtattgcg agaacctgtt ggaaaccgtg | 1080 |
| gaggaggccg agaagttgtt gaacctgagc ccgcagacgt acttctccgt tcacaccgac | 1140 |
| aacgaggacg gtacgccgtt gagcggcagc agcctgccgc caccgtttcc gccgtgcacc | 1200 |
| ttgcgcacgg cattgaccaa atacgcagac ttgacttctg caccgaaaaa gtcggtgctg | 1260 |
| gtggcgctgg ccgagtacgc atctgaccag ggtgaagcgg atcgtttgcg tttcttggcg | 1320 |
| agcccgagcg gcaaagagga atatgcacag tacatcttgg caagccagcg cacgctgctg | 1380 |
| gaggtcatgg cggagttccc gtcggcgaaa ccgccgctgg gtgtcttttt cgcgggtgtc | 1440 |
| gctccgcgcc tgcagccgcg tttctattcc attagctcta gcccgaagat cgcaccgttc | 1500 |
| cgtattcacg tgacctgcgc cctggtttat gacaaatccc ctaccggtcg cgttcataag | 1560 |
| ggcatctgta gcacgtggat gaaaaatgcg gtcccgctgg aagaaagcaa cgattgttcc | 1620 |
| tgggctccga tcttcgtccg caacagcaac ttcaagctgc cgaccgaccc gaaggttccg | 1680 |
| attatcatga ttggtccggg taccggtctg gcccctttc gtggcttttt gcaagagcgc | 1740 |
| ttggcgttga aagagagcgg tgctgaattg ggtccggcga tcttgttctt ggttgccgt | 1800 |
| aaccgtaaaa tggactttat ttacgaggat gaactgaatg atttcgtcaa agcgggcgtt | 1860 |
| gtcagcgagc tgatcgtcgc ttttagccgc gaaggcccga tgaaagaata cgtgcaacac | 1920 |
| aaaatgagcc aacgtgcctc cgatgtgtgg aacatcatta gcgacggtgg ttatgtttat | 1980 |

```
gtttgcggtg acgcgaaggg tatggctcgt gatgttcacc gtaccctgca taccatcgca    2040
caggagcaag gtagcatgtc cagctcggag gccgaaggta tggtcaaaaa cctgcaaacc    2100
accggtcgtt acctgcgtga tgtgtggtaa taa                                 2133
```

<210> SEQ ID NO 4
<211> LENGTH: 709
<212> TYPE: PRT
<213> ORGANISM: Mentha piperita

<400> SEQUENCE: 4

```
Met Glu Pro Ser Ser Gln Lys Leu Ser Pro Leu Glu Phe Val Ala Ala
1               5                   10                  15

Ile Leu Lys Gly Asp Tyr Ser Ser Gly Gln Val Glu Gly Gly Pro Pro
            20                  25                  30

Pro Gly Leu Ala Ala Met Leu Met Glu Asn Lys Asp Leu Val Met Val
        35                  40                  45

Leu Thr Thr Ser Val Ala Val Leu Ile Gly Cys Val Val Leu Ala
    50                  55                  60

Trp Arg Arg Ala Ala Gly Ser Gly Lys Tyr Lys Gln Pro Glu Leu Pro
65                  70                  75                  80

Lys Leu Val Val Pro Lys Ala Ala Glu Pro Glu Glu Ala Glu Asp Asp
                85                  90                  95

Lys Thr Lys Ile Ser Val Phe Phe Gly Thr Gln Thr Gly Thr Ala Glu
            100                 105                 110

Gly Phe Ala Lys Ala Phe Val Glu Glu Ala Lys Ala Arg Tyr Gln Gln
        115                 120                 125

Ala Arg Phe Lys Val Ile Asp Leu Asp Asp Tyr Ala Ala Asp Asp Asp
    130                 135                 140

Glu Tyr Glu Glu Lys Leu Lys Lys Glu Asn Leu Ala Phe Phe Phe Leu
145                 150                 155                 160

Ala Ser Tyr Gly Asp Gly Glu Pro Thr Asp Asn Ala Ala Arg Phe Tyr
                165                 170                 175

Lys Trp Phe Thr Glu Gly Lys Asp Arg Gly Glu Trp Leu Asn Asn Leu
            180                 185                 190

Gln Tyr Gly Val Phe Gly Leu Gly Asn Arg Gln Tyr Glu His Phe Asn
        195                 200                 205

Lys Ile Ala Ile Val Val Asp Asp Leu Ile Phe Glu Gln Gly Gly Lys
    210                 215                 220

Lys Leu Val Pro Val Gly Leu Gly Asp Asp Gln Cys Ile Glu Asp
225                 230                 235                 240

Asp Phe Ala Ala Trp Arg Glu Leu Val Trp Pro Glu Leu Asp Lys Leu
                245                 250                 255

Leu Arg Asn Glu Asp Asp Ala Thr Val Ala Thr Pro Tyr Ser Ala Ala
            260                 265                 270

Val Leu Gln Tyr Arg Val Val Phe His Asp His Ile Asp Gly Leu Ile
        275                 280                 285

Ser Glu Asn Gly Ser Pro Asn Gly His Ala Asn Gly Asn Thr Val Tyr
    290                 295                 300

Asp Ala Gln His Pro Cys Arg Ser Asn Val Ala Val Lys Lys Glu Leu
305                 310                 315                 320

His Thr Pro Ala Ser Asp Arg Ser Cys Thr His Leu Glu Phe Asn Ile
                325                 330                 335

Ser Gly Thr Gly Leu Met Tyr Glu Thr Gly Asp His Val Gly Val Tyr
            340                 345                 350
```

```
Cys Glu Asn Leu Leu Glu Thr Val Glu Glu Ala Glu Lys Leu Leu Asn
        355                 360                 365

Leu Ser Pro Gln Thr Tyr Phe Ser Val His Thr Asp Asn Glu Asp Gly
    370                 375                 380

Thr Pro Leu Ser Gly Ser Ser Leu Pro Pro Pro Phe Pro Pro Cys Thr
385                 390                 395                 400

Leu Arg Thr Ala Leu Thr Lys Tyr Ala Asp Leu Thr Ser Ala Pro Lys
                405                 410                 415

Lys Ser Val Leu Val Ala Leu Ala Glu Tyr Ala Ser Asp Gln Gly Glu
            420                 425                 430

Ala Asp Arg Leu Arg Phe Leu Ala Ser Pro Ser Gly Lys Glu Glu Tyr
            435                 440                 445

Ala Gln Tyr Ile Leu Ala Ser Gln Arg Thr Leu Leu Glu Val Met Ala
        450                 455                 460

Glu Phe Pro Ser Ala Lys Pro Pro Leu Gly Val Phe Ala Gly Val
465                 470                 475                 480

Ala Pro Arg Leu Gln Pro Arg Phe Tyr Ser Ile Ser Ser Pro Lys
                485                 490                 495

Ile Ala Pro Phe Arg Ile His Val Thr Cys Ala Leu Val Tyr Asp Lys
            500                 505                 510

Ser Pro Thr Gly Arg Val His Lys Gly Ile Cys Ser Thr Trp Met Lys
        515                 520                 525

Asn Ala Val Pro Leu Glu Glu Ser Asn Asp Cys Ser Trp Ala Pro Ile
    530                 535                 540

Phe Val Arg Asn Ser Asn Phe Lys Leu Pro Thr Asp Pro Lys Val Pro
545                 550                 555                 560

Ile Ile Met Ile Gly Pro Gly Thr Gly Leu Ala Pro Phe Arg Gly Phe
                565                 570                 575

Leu Gln Glu Arg Leu Ala Leu Lys Glu Ser Gly Ala Glu Leu Gly Pro
            580                 585                 590

Ala Ile Leu Phe Phe Gly Cys Arg Asn Arg Lys Met Asp Phe Ile Tyr
        595                 600                 605

Glu Asp Glu Leu Asn Asp Phe Val Lys Ala Gly Val Val Ser Glu Leu
    610                 615                 620

Ile Val Ala Phe Ser Arg Glu Gly Pro Met Lys Glu Tyr Val Gln His
625                 630                 635                 640

Lys Met Ser Gln Arg Ala Ser Asp Val Trp Asn Ile Ile Ser Asp Gly
                645                 650                 655

Gly Tyr Val Tyr Val Cys Gly Asp Ala Lys Gly Met Ala Arg Asp Val
            660                 665                 670

His Arg Thr Leu His Thr Ile Ala Gln Glu Gln Gly Ser Met Ser Ser
        675                 680                 685

Ser Glu Ala Glu Gly Met Val Lys Asn Leu Gln Thr Thr Gly Arg Tyr
    690                 695                 700

Leu Arg Asp Val Trp
705

<210> SEQ ID NO 5
<211> LENGTH: 1710
<212> TYPE: DNA
<213> ORGANISM: artificial sequence
<220> FEATURE:
<223> OTHER INFORMATION: synthetic codon optimized cDNA encoding for
      SaTps 8201
```

<400> SEQUENCE: 5

```
atggacagca gcaccgccac cgcaatgacc gcaccattca tcgacccgac ggatcatgtg      60
aatctgaaaa ccgacacgga tgcgagcgaa atcgtcgta tgggtaacta caagccgagc     120
atttggaact acgattttct gcagtccctg gcgacgcacc acaacattgt tgaagagcgt     180
cacctgaagc tggcagagaa actgaaaggt caagtgaaat tcatgttcgg tgcgccgatg     240
gagccattgg ctaagttgga gctggttgat gtggtgcaac gcttgggtct gaaccacctg     300
ttcgagactg aaatcaaaga agctctgttc agcatctaca aagatggcag caatggctgg     360
tggtttggcc atctgcatgc tacctctttg cgcttccgtc tgttgcgcca atgtggcctg     420
tttatcccgc aggacgtttt caaaaccttt caaaacaaga ccggtgagtt tgacatgaag     480
ctgtgggaca cgttaaggg cctgctgagc ctgtacgagg cgagctacct gggctggaag     540
ggcgagaaca tcttggatga agcaaaggcg ttcacgacca agtgcctgaa gagcgcatgg     600
gagaacatta gcgagaagtg gctggcgaag cgtgttaaac atgcgttggc gctgccgctg     660
cactggcgtg ttccgcgtat tgaagcacgc tggtttatcg aggtgtacga caagaggcc     720
aatatgaatc cgacgctgct gaaactggcg aaactggact tcaacatggt ccaaagcatt     780
caccagaaag aaatcggtga actggcccgc tggtgggtta ctaccggcct ggacaagctg     840
gatttcgcac gcaacaatct gttgcagtct tatatgtgga gctgcgccat cgcgtccgac     900
ccgaaattca aactggcgcg tgaaaccatt gtcgagatcg gttccgtgtt gacggttgtc     960
gacgacggct atgatgtgta cggttctatg gatgagctgg acctgtacac cagctcggtg    1020
gagcgttggt cctgtgtcaa aattgacaag ctgcctaata cgctgaagct gatctttatg    1080
tctatgttca caaaaccaa cgaggtgggt ctgcgtgttc aacacgagcg tggttacaat    1140
agcatcccga ccttcattaa ggcgtggggt gaacagtgta agagctatca aaagaggcg    1200
cgttggtttc atggtggtca cacgcctccg ctggaagaat acagcctgaa cggtctggtc    1260
agcattggtt ttccgctgtt gctgatcacc ggctatgttg cgattgctga gaatgaagca    1320
gccctggata agtccaccc gctgccggac ctgctgcatt attccagctt gctgagccgt    1380
ctgattaatg atatcggcac tagcccggat gaaatggcgc gtggtgacaa tctgaagagc    1440
attcactgct atatgaatga aaccggtgcc agcgaagagg tcgcacgcga gcacatcaaa    1500
ggcgtcatcg aagagaattg gaaaattctg aaccagtgtt gctttgacca gtcccagttc    1560
caggagccgt tcatcacgtt taacctgaac agcgtgcgcg gctcgcattt cttctatgaa    1620
tttggtgatg gttttggtgt taccgacagc tggaccaagg tggatatgaa aagcgtcctg    1680
attgatccga ttccgctggg tgaagagtaa                                     1710
```

<210> SEQ ID NO 6
<211> LENGTH: 569
<212> TYPE: PRT
<213> ORGANISM: Santalum album

<400> SEQUENCE: 6

```
Met Asp Ser Ser Thr Ala Thr Ala Met Thr Ala Pro Phe Ile Asp Pro
1               5                  10                  15

Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr His His Asn Ile Val Glu Glu Arg His Leu Lys Leu
    50                  55                  60
```

```
Ala Glu Lys Leu Lys Gly Gln Val Lys Phe Met Phe Gly Ala Pro Met
 65              70                  75                  80

Glu Pro Leu Ala Lys Leu Glu Leu Val Asp Val Val Gln Arg Leu Gly
                 85                  90                  95

Leu Asn His Leu Phe Glu Thr Glu Ile Lys Glu Ala Leu Phe Ser Ile
            100                 105                 110

Tyr Lys Asp Gly Ser Asn Gly Trp Trp Phe Gly His Leu His Ala Thr
        115                 120                 125

Ser Leu Arg Phe Arg Leu Leu Arg Gln Cys Gly Leu Phe Ile Pro Gln
    130                 135                 140

Asp Val Phe Lys Thr Phe Gln Asn Lys Thr Gly Glu Phe Asp Met Lys
145                 150                 155                 160

Leu Trp Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Thr
            180                 185                 190

Thr Lys Cys Leu Lys Ser Ala Trp Glu Asn Ile Ser Glu Lys Trp Leu
        195                 200                 205

Ala Lys Arg Val Lys His Ala Leu Ala Leu Pro Leu His Trp Arg Val
    210                 215                 220

Pro Arg Ile Glu Ala Arg Trp Phe Ile Glu Val Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Asp Phe Ala Arg Asn Asn Leu Leu
        275                 280                 285

Gln Ser Tyr Met Trp Ser Cys Ala Ile Ala Ser Asp Pro Lys Phe Lys
    290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Met Asp Glu Leu Asp Leu Tyr
                325                 330                 335

Thr Ser Ser Val Glu Arg Trp Ser Cys Val Lys Ile Asp Lys Leu Pro
            340                 345                 350

Asn Thr Leu Lys Leu Ile Phe Met Ser Met Phe Asn Lys Thr Asn Glu
        355                 360                 365

Val Gly Leu Arg Val Gln His Glu Arg Gly Tyr Asn Ser Ile Pro Thr
    370                 375                 380

Phe Ile Lys Ala Trp Val Glu Gln Cys Lys Ser Tyr Gln Lys Glu Ala
385                 390                 395                 400

Arg Trp Phe His Gly His Thr Pro Pro Leu Glu Glu Tyr Ser Leu
                405                 410                 415

Asn Gly Leu Val Ser Ile Gly Phe Pro Leu Leu Leu Ile Thr Gly Tyr
            420                 425                 430

Val Ala Ile Ala Glu Asn Glu Ala Ala Leu Asp Lys Val His Pro Leu
        435                 440                 445

Pro Asp Leu Leu His Tyr Ser Ser Leu Leu Ser Arg Leu Ile Asn Asp
    450                 455                 460

Ile Gly Thr Ser Pro Asp Glu Met Ala Arg Gly Asp Asn Leu Lys Ser
465                 470                 475                 480
```

-continued

```
Ile His Cys Tyr Met Asn Glu Thr Gly Ala Ser Glu Glu Val Ala Arg
            485                 490                 495

Glu His Ile Lys Gly Val Ile Glu Glu Asn Trp Lys Ile Leu Asn Gln
        500                 505                 510

Cys Cys Phe Asp Gln Ser Gln Phe Gln Glu Pro Phe Ile Thr Phe Asn
            515                 520                 525

Leu Asn Ser Val Arg Gly Ser His Phe Phe Tyr Glu Phe Gly Asp Gly
        530                 535                 540

Phe Gly Val Thr Asp Ser Trp Thr Lys Val Asp Met Lys Ser Val Leu
545                 550                 555                 560

Ile Asp Pro Ile Pro Leu Gly Glu Glu
            565

<210> SEQ ID NO 7
<211> LENGTH: 5402
<212> TYPE: DNA
<213> ORGANISM: artificial sequence
<220> FEATURE:
<223> OTHER INFORMATION: synthetic operon encoding for SaCP816, CPRm and
      SaSAS

<400> SEQUENCE: 7
catatggcac tgttgttggc ggttttctgg agcgctttga ttattctggt tagcatctta        60
ttgcgtcgtc gtcaaaaacg caacaatttg ccaccgggcc accggcccct gccgatcatc       120
ggtaacattc acattctggg caccctgccg caccagagcc tgtacaatct ggcgaagaag       180
tacggtccga tcatgtccat gcgtttgggc ttggttccgg cggtggtcat cagcagcccg       240
gaagcggccg agctggtcct gaaaacccac gacatcgttt ttgcttctcg ccctcgtctg       300
caagttgcag attactttca ctatggcacc aaaggcgtga ttctgaccga atatggtacc       360
tactggcgta acatgcgtcg cctgtgcacg gtcaaactgc tgaacaccgt taagattgat       420
agctttgcag gcacccgcaa gaaagaagtc gctagcttcg ttcagagcct gaaagaagca       480
agcgtggcgc acaaaatggt taacctgtcc gcacgcgtcg ctaatgttat tgagaatatg       540
gtttgtctga tggttattgg tagatcgtct gacgagcgtt tcaagctgaa agaagtgatc       600
caagaagcgg cacagctggc gggtgccttc aatattggtg actatgtccc gtttctgatg       660
ccgctggatc tgcagggcct gactcgccgt atcaagagcg gtagcaaggc attcgatgac       720
atcctcgagg tcattatcga cgagcatgtg caagacatta agatcatga cgatgagcag       780 catggtgact tcatcgacgt gctgctggcg atgatgaata gccgatgga ttctcgtgag       840 ggtctgtcca tcattgatcg cacgaacatt aaagcgatcc tggtggatat gatcggtgcc       900
gcgatggaca cgagcaccag cggtgtggag tgggcgattt cggagctgat taagcatcct       960
cgtgtcatga gaaactgca agacgaagtg aaaaccgtaa tcggtatgaa ccgcatggtg      1020
gaagaagcgg atctgccgaa actgccgtac ctggacatgg ttgtcaagga acgatgcgt      1080 ctgcatccgc aggcccgct gctggtgccg cgtgaaagca tggaagatat tacgatcaac      1140
ggttactata tcccgaagaa atcccgcatt attgtgaatg catgggcgat cggccgtgac      1200
accaacgcct ggagcaataa tgcgcacgag ttttccctg agcgttttat gagctctaac      1260
gttgatctgc aaggccagga cttccagctg atcccgttcg gtagcggtcg tcgcggttgt      1320
ccgggcatgc gtctgggtct gacgacggtc cgcttggtgc tggcccaact gattcactgc      1380
ttcgacctgg agcttccgaa gggcaccgtc gcgactgacc tggatatgag cgagaagttt      1440
ggtctggcaa tgccgcgtgc gcagcactta ctggccttc cgacctaccg tctggagagc      1500
```

```
taagtcgact aactttaaga aggagatata tccatggaac ctagctctca gaaactgtct    1560
ccgttggaat tgttgctgc tatcctgaag ggcgactaca gcagcggtca ggttgaaggt    1620
ggtccaccgc caggtctggc agctatgttg atggaaaata aggatttggt gatggttctg    1680
acgacgtccg tggcagtcct gatcggctgt gtcgtggtcc tggcatggcg tcgtgcggca    1740
ggtagcggta agtacaagca acctgaactg cctaaactgg tggtcccgaa agcagccgaa    1800
ccggaggagg cagaggatga taaaaccaag atcagcgtgt ttttcggcac ccaaaccggt    1860
acggcagaag gtttcgcgaa ggcttttgtt gaagaggcca aggcgcgtta tcagcaggcc    1920
cgtttcaaag ttatcgacct ggacgactat gcggcagacg atgacgagta cgaagagaaa    1980
ctgaagaagg aaaacttggc attcttcttc ttggcgtcct acggtgacgg cgagccgacg    2040
gacaacgcgg cacgctttta caaatggttt acggagggta aggaccgtgg tgaatggctg    2100
aacaatctgc agtacggcgt ttttggtctg ggtaaccgtc aatatgagca tttcaataag    2160
atcgccattg tcgtcgatga tctgatcttc gagcaaggtg gcaagaagct ggttccggtg    2220
ggtctgggtg acgatgacca gtgcattgag atgattttg cggcgtggcg tgaactggtc    2280
tggccggaac tggataaact gctgcgtaac gaagacgacg ctaccgtggc aaccccgtac    2340
agcgccgctg tgctgcaata ccgcgtggtt ttccacgatc acattgacgg cctgattagc    2400
gaaaacggta gcccgaacgg tcatgctaat ggcaataccg tgtacgatgc gcaacacccg    2460
tgccgtagca acgtcgcggt caagaaggaa ttgcatactc cggcgagcga tcgcagctgc    2520
acccacctgg aatttaacat tagcggtacc ggcctgatgt acgagacggg tgaccacgtc    2580
ggtgtgtatt gcgagaacct gttggaaacc gtggaggagg ccgagaagtt gttgaacctg    2640
agcccgcaga cgtacttctc cgttcacacc gacaacgagg acggtacgcc gttgagcggc    2700
agcagcctgc cgccaccgtt tccgccgtgc accttgcgca cggcattgac caaatacgca    2760
gacttgactt ctgcaccgaa aaagtcggtg ctggtggcgc tggccgagta cgcatctgac    2820
cagggtgaag cggatcgttt gcgtttcttg gcgagcccga gcggcaaaga ggaatatgca    2880
cagtacatct tggcaagcca gcgcacgctg ctggaggtca tggcggagtt cccgtcggcg    2940
aaaccgccgc tgggtgtctt tttcgcgggt gtcgctccgc gcctgcagcc gcgtttctat    3000
tccattagct ctagcccgaa gatcgcaccg ttccgtattc acgtgacctg cgccctggtt    3060
tatgacaaat cccctaccgg tcgcgttcat aagggcatct gtagcacgtg gatgaaaaat    3120
gcggtcccgc tggaagaaag caacgattgt tcctgggctc cgatcttcgt ccgcaacagc    3180
aacttcaagc tgccgaccga cccgaaggtt ccgattatca tgattggtcc gggtaccggt    3240
ctggccccctt ttcgtggctt tttgcaagag cgcttggcgt tgaaagagag cggtgctgaa    3300
ttgggtccgg cgatcttgtt ctttggttgc cgtaaccgta aaatggactt tatttacgag    3360
gatgaactga atgatttcgt caaagcgggc gttgtcagcg agctgatcgt cgcttttagc    3420
cgcgaaggcc cgatgaaaga atacgtgcaa cacaaaatga gccaacgtgc ctccgatgtg    3480
tggaacatca ttagcgacgg tggttatgtt tatgtttgcg gtgacgcgaa gggtatggct    3540
cgtgatgttc accgtacccct gcataccatc gcacaggagc aaggtagcat gtccagctcg    3600
gaggccgaag gtatggtcaa aaacctgcaa accaccggtc gttacctgcg tgatgtgtgg    3660
taataaaagc ttaggaggta aaacatatgg acagcagcac cgccaccgca atgaccgcac    3720
cattcatcga cccgacggat catgtgaatc tgaaaaccga cacgcgatgcg agcgaaaatc    3780
gtcgtatggg taactacaag ccgagcattt ggaactacga ttttctgcag tccctggcga    3840
cgcaccacaa cattgttgaa gagcgtcacc tgaagctggc agagaaactg aaaggtcaag    3900
```

```
tgaaattcat gttcggtgcg ccgatggagc cattggctaa gttggagctg gttgatgtgg    3960
tgcaacgctt gggtctgaac cacctgttcg agactgaaat caaagaagct ctgttcagca    4020
tctacaaaga tggcagcaat ggctggtggt ttggccatct gcatgctacc tctttgcgct    4080
tccgtctgtt gcgccaatgt ggcctgttta tcccgcagga cgttttcaaa accttcaaa     4140
acaagaccgg tgagtttgac atgaagctgt gggacaacgt taagggcctg ctgagcctgt    4200
acgaggcgag ctacctgggc tggaaggcg agaacatctt ggatgaagca aaggcgttca     4260
cgaccaagtg cctgaagagc gcatgggaga acattagcga gaagtggctg gcgaagcgtg    4320
ttaaacatgc gttggcgctg ccgctgcact ggcgtgttcc gcgtattgaa gcacgctggt    4380
ttatcgaggt gtacgaacaa gaggccaata tgaatccgac gctgctgaaa ctggcgaaac    4440
tggacttcaa catggtccaa agcattcacc agaaagaaat cggtgaactg gcccgctggt    4500
gggttactac cggcctggac aagctggatt tcgcacgcaa caatctgttg cagtcttata    4560
tgtggagctg cgccatcgcg tccgacccga aattcaaact ggcgcgtgaa accattgtcg    4620
agatcggttc cgtgttgacg gttgtcgacg acggctatga tgtgtacggt tctatggatg    4680
agctggacct gtacaccagc tcggtggagc gttggtcctg tgtcaaaatt gacaagctgc    4740
ctaatacgct gaagctgatc tttatgtcta tgttcaacaa aaccaacgag gtgggtctgc    4800
gtgttcaaca cgagcgtggt tacaatagca tcccgacctt cattaaggcg tgggtggaac    4860
agtgtaagag ctatcaaaaa gaggcgcgtt ggtttcatgg tggtcacacg cctccgctgg    4920
aagaatacag cctgaacggt ctggtcagca ttggttttcc gctgttgctg atcaccggct    4980
atgttgcgat tgctgagaat gaagcagccc tggataaagt ccacccgctg ccggacctgc    5040
tgcattattc cagcttgctg agccgtctga ttaatgatat cggcactagc ccggatgaaa    5100
tggcgcgtgg tgacaatctg aagagcattc actgctatat gaatgaaacc ggtgccagcg    5160
aagaggtcgc acgcgagcac atcaaaggcg tcatcgaaga gaattggaaa attctgaacc    5220
agtgttgctt tgaccagtcc cagttccagg agccgttcat cacgtttaac ctgaacagcg    5280
tgcgcggctc gcatttcttc tatgaatttg gtgatggttt tggtgttacc gacagctgga    5340
ccaaggtgga tatgaaaagc gtcctgattg atccgattcc gctgggtgaa gagtaagctt    5400
gc                                                                   5402
```

BIOCHEMICALLY PRODUCED SANDALWOOD OIL

TECHNICAL FIELD

The present invention relates to the field of perfumery. More particularly, it concerns a biochemically produced sandalwood oil, as defined herein. Moreover, the present invention comprises the use of the biochemically produced sandalwood oil as part of a perfuming composition or of a perfuming consumer produce. The present invention comprises the use of the biochemically produced sandalwood oil as an anti-microbial and anti-inflammatory agent, and also as an arthropod control composition.

BACKGROUND

Sandalwood oil, distilled from the heart wood and roots of the sandalwood tree, is one of the most valuable essential oils, valued by perfumers for its woody notes, providing a deep rich base note to perfumes and acting as a natural fixative. In addition to acting as a feed stock for the production of the essential oil, the wood is also valued for carving, and furniture making. Rising demand and very high prices for both wood and essential oil, a slow growing tree which takes 30 to 60 years to give a crop, a destructive harvest to get at the roots and heartwood with no sustainable harvesting options, and the scene is set for uncontrolled and illegal harvesting and destruction of the natural resource. 40 years ago sandalwood oil was sold at under US$100/kg; today its market value is over US$2,000/kg reflecting the constraint to supply Sandalwood oils come from a range of species, and while they all have similar uses, quality and characteristics vary between the oils of the different species. The key species used for distillation of essential oils are listed below, with East Indian Sandalwood oil and Australian Sandalwood oil dominating supplies to the market: East Indian Sandalwood oil (*Santalum album*) is the most well-known and oldest traded type of sandalwood, and has been in use for thousands of years. Cultivation centered in India (it is native to the highlands of southern India and the Malayan Archipelago) with the center of production in India in Mysore. Its natural distribution extends down to Indonesia (particularly Timor), and it has been introduced into Australia and plantations established in the tropical north-western areas—an estimated 8,000 ha with annual additions of around 1,000 ha; more recently it has also been introduced into a number of the S Pacific Islands and plantations established (Fiji, Tonga, Vanuatu, New Caledonia); Australian Sandalwood oil (*Santalum spicatum*, syn. *Eucarya spicata* (also referred to as West Australian Sandalwood oil) is native to the desert-like areas of SW Australia, close to Perth. Substantial plantations have also now been established—around 15,000 ha with annual additions of 1-2,000 ha. A second sandalwood species, *S. lanceolatum*, is also found in Australia, principally in Queensland, NSW, and northwestern part of Western Australia, but is little used commercially. *Santalum paniculatum*. Only found in Hawaii. Around 7,000 ha reported to be under sustainable management. Commercial oil now coming onto the market. *Santalum yasi*. Found in Fiji, Samoa and Tonga. Traditionally included in mixed cropping agroforestry cultivation systems. The species hybridizes readily with *S. album* resulting in variable quality of oil depending on the source trees.

Heartwood and roots are chipped and pulverized to a coarse grind before distillation. Oil yield varies with the plant part, the age of the tree and the environment of cultivation. Roots can give up to 10% oil; heartwood up to 4%. Distillation takes 48 to 72 hours, and effectively ends when the yield of oil ceases to be economical. High pressure steam distillation will give a higher yield and reduced distillation time but will lose some of the delicate notes.

A rise in the number of working populations in the developing economies has led to increased stress levels, which inclines consumers toward spas for relaxation. This ultimately has a positive impact on the sandalwood oil market since it is a widely used essential oil for aromatherapy. Increase in demand for natural perfume over synthetic perfume is a major driver for the sandalwood oil market. With rise in disposable income of the population, there is an escalation in the demand for personal care products such as aromatic soaps, shampoos, and lotions, which drives the growth of the market. However, high price of sandalwood oil is expected to hinder the growth of the sandalwood oil market.

Unfortunately, because of the high value placed on sandalwood products, especially on sandalwood oil, the sandalwood tree has a long history of exploitation. High demand for the tree's valuable oil has resulted in over-harvesting, and consequently, the sandalwood tree is one of the most exploited groups of plants across its range. Today, many sandalwood species are considered "vulnerable" by the IUCN.

Hence there is a need for alternative means of preparing sandalwood oils which can be used for the commercial uses mentioned above.

SUMMARY OF THE INVENTION

The present invention provides a biochemically produced sandalwood oil.

An aspect of the invention provides a biochemically produced sandalwood oil comprising at least 85% santalol and bergamotol and 1% or less cis-lanceol, wherein the oil has one or more of the following features: i) 5% or less alpha-santalal, ii) 5% or less farnesol; iii) 0.5% or less spirosantalol.

An embodiment of this aspect of the invention is wherein the 85% santalol and bergamotol comprises 37-65% alpha-santalol, 13-37% beta-santalol and 1 to 35% bergamotol.

An embodiment of this aspect of the invention is wherein the ratio of cis-alpha-santalol to trans-alpha-santalol is 90:1 or less.

An embodiment of this aspect of the invention is wherein the alpha-santalal is 90% or more trans-alpha-santalal.

An embodiment of this aspect of the invention is wherein the biochemically produced sandalwood oil comprises 0-1% cis-beta-sinensol.

An embodiment of this aspect of the invention is wherein the biochemically produced sandalwood oil comprises: i) 50-60% alpha-santalol, ii) 20-35% beta-santalol; iii) 5% or less alpha-santalal; iv) 5% or less farnesol; v) 5% or less spirosantalol; vi) 4-10% bergamotol; vii) 0-5% cis-beta-sinensol; viii) 5% or less epi-beta-santalol.

An embodiment of this aspect of the invention is wherein the biochemically produced sandalwood oil comprises: i) 54%-59% alpha-santalol; ii) 25.1%-30% beta-santalol; iii) 0.7%-3% alpha-santalal; iv) 1%-2.3% farnesol; v) 0.5% or less spirosantalol; vi) 6.3%-7.2% bergamotol; vii) 0.6%—1.4% cis-beta-sinensol; viii) 1%-2% epi-beta-santalol.

An embodiment of this aspect of the invention is wherein the biochemically produced sandalwood oil is microbially produced.

An embodiment of this aspect of the invention is wherein the biochemically produced sandalwood oil is encapsulated within a matrix material.

An aspect of the invention provides a method of preparing the biochemically produced sandalwood oil the invention comprising (i) cultivating a genetically engineered organism capable of producing FPP and which expresses a suitable sesquiterpene synthase, a cytochrome P450 and a CPR, and (ii) isolating the biochemically produced sandalwood oil of the invention.

An aspect of the invention provides a perfuming composition comprising: i) the sandalwood oil of the invention; ii) at least one ingredient selected from the group consisting of a perfumery carrier and a perfumery base; and iii) optionally at least one perfumery adjuvant.

An aspect of the invention provides a perfumed consumer product comprising the biochemically produced sandalwood oil or perfuming composition of the invention.

An embodiment of this aspect of the invention is wherein the perfumery consumer product is a perfume, a fabric care product, a body-care product, a cosmetic preparation, a skin-care product, an air care product or a home care product or wherein the perfumery consumer product is a fine perfume, a splash or eau de perfume, a cologne, a shave or an after-shave lotion, a liquid or solid detergent, a fabric softener, a fabric refresher, an ironing water, a paper, a bleach, a carpet cleaner, curtain-care products, a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, a car care product.

An aspect of the invention provides a sandalwood oil of the invention for use in the treatment of a microbial infection, an inflammatory condition and/or increase skin moisturizing, or for use in the treatment of acne, eczema, psoriasis, seborrheic or atopic dermatitis.

An aspect of the invention provides an arthropod control composition comprising the sandalwood oil of the invention.

DESCRIPTION OF THE INVENTION

Figure 1:
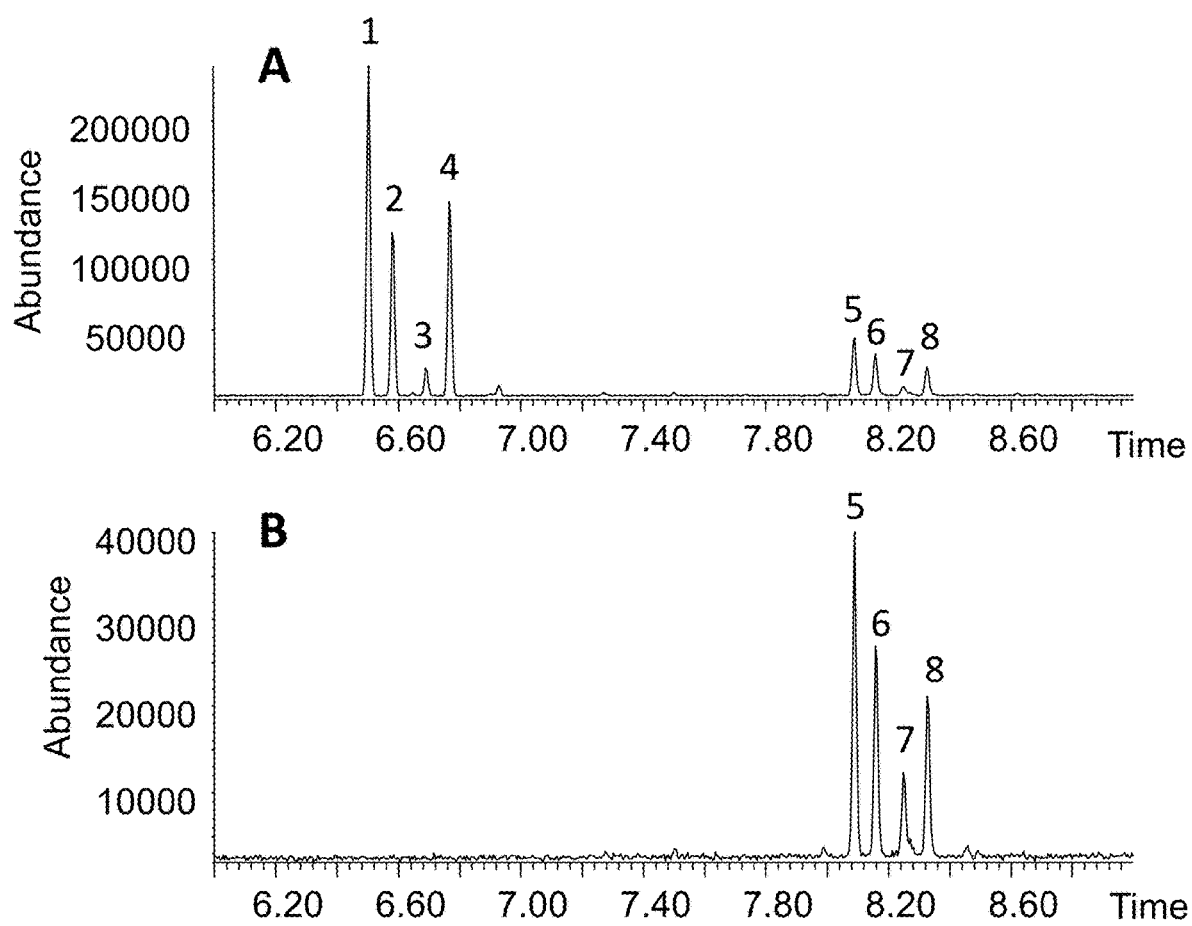
FIG. 1: GCMS analysis of the molecules produced by *E. Coli* engineered to produced sesquiterpenes and expressing an alpha-santalene/beta-santalene synthase (SaSAS), cytochrome P450 reductase (CPRm) and a cytochrome P450 monooxygenase SaCP816. A. Total sesquiterpene mixture obtained after solvent extraction of the culture medium. B. Oxygenated sesquiterpene fraction obtained after an additional purification step. 1, α-santalene; 2, α-trans-bergamotene; 3, epi-β-santalene; 4, β-santalene; 5, (Z)-α-santalol; 6, (Z)-α-trans-bergamotol; 7, (Z)-epi-β-santalol; 8, (Z)-β-santalol.

In the context of the descriptions provided herein and of the appended claims, the use of "or" means "and/or" unless stated otherwise.

Similarly, "comprise," "comprises," "comprising", "include," "includes," and "including" are interchangeable and not intended to be limiting.

The term"about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 98.5%, like 95 to 99%.

The biochemically produced sandalwood oil of the invention may comprise the following compounds.

cis-alpha-santalol, (+)-cis-alpha-santalol (alpha(2Z)-santalol), (+)-(2Z)-5-[(1S,3R,4R)-2,3-dimethyltricyclo [2.2.1.0~2,6~]hept-3-yl]-2-methyl-2-penten-1-ol.

trans-alpha-santalol, (+)-trans-alpha-santalol (alpha(2E)-santalol), (2E)-5-[(3S)-2,3-dimethyltricyclo[2.2.1.0~2, 6~]hept-3-yl]-2-methyl-2-penten-1-ol.

cis-beta-santalol, (−)-cis-beta-santalol (beta (2Z)-santalol), (−)-(2Z)-2-methyl-5-[(1S,2R,4R)-2-methyl-3-methylenebicyclo[2.2.1]hept-2-yl]-2-penten-1-ol.

trans-beta-santalol, (−)-trans-beta-santalol (beta (2E)-santalol), (E)-2-methyl-5-((1RS,2SR,4SR)-2-methyl-3-methylenebicyclo[2.2.1]heptan-2-yl)pent-2-en-1-ol.

cis-lanceol, (−)-cis-lanceol, 2,6-Heptadien-1-ol, 2-methyl-6-[(1S)-4-methyl-3-cyclohexen-1-yl]-, (2Z)-.

cis-alpha-santalal (alpha-santalal (Z)-), (+)-(2Z)-5-[(3R)-2,
   3-dimethyltricyclo[2.2.1.0~2,6~]hept-3-yl]-2-methyl-2-
   pentenal.
trans-alpha-santalal (alpha-santalal, (E)-), (+)-(2E)-5-[(3R)-
   2,3-dimethyltricyclo[2.2.1.0~2,6~]hept-3-yl]-2-methyl-
   2-pentenal.
spirosantalol, Spiro[bicyclo[2.2.1]heptane-2,1'-cyclopentane]-3'-ethanol, β,3-bis(methylene)-.
farnesol, (2E,6E)-farnesol, (2E,6E)-3,7,11-trimethyl-2,6,10-
   dodecatrien-1-ol, CAS number 106-28-5
trans-beta-santalal, (2E)-2-methyl-5-[(1S,2R,4R)-2-methyl-
   3-methylenebicyclo[2.2.1]hept-2-yl]-2-pentenal.
bergamotol, (−)-(Z)-alpha-bergamotol, (−)-(Z)-5-((1S,5S,
   6R)-2,6-dimethylbicyclo[3.1.1]hept-2-en-6-yl)-2-methyl-
   pent-2-en-1-ol.

The following components can also be present in the biochemically produced sandalwood oil of the invention.
(1S,2R,4S,7R)-1,7-dimethyl-7-(4-methyl-3-penten-1-yl)bicyclo[2.2.1]heptan-2-ol.
epi-beta-santalol, (Z)-epi-beta-santalol, (2Z)-2-methyl-5-
   [(1S,2R,4R)-2-methyl-3-methylenebicyclo[2.2.1]hept-2-
   yl]-2-pentenal.
Dihydro-alpha-santalol 5-[(3R)-2,3-dimethyltricyclo
   [2.2.1.0~2,6~]hept-3-yl]-2-methyl-1-pentanol.
cis-beta-sinensol, (2Z,6E)-2,6-dimethyl-10-methylidene-2,
   6,11-dodecatrien-1-ol,
5-(2,3-dimethyltricyclo[2.2.1.0~2,6]heptan-3-yl)pent-3-en-
   2-one.
2,3-dimethyl-3-(4-methyl-3-penten-1-yl)bicyclo[2.2.1]heptan-2-ol.
(E,Z)-beta-sinensol, 2,6,11-Dodecatrien-1-ol, 2,6-dimethyl-
   10-methylene-, (E,Z)-.
(2E,6E)-beta-sinensol 2,6,11-Dodecatrien-1-ol, 2,6-dimethyl-10-methylene-, (2E,6E)-.
alpha-santalene, alpha-santalene, (7R)-1,7-dimethyl-7-(4-
   methyl-3-penten-1-yl)tricyclo[2.2.1.0~2,6~]heptane.
alpha-farnesene, (z;z)-alpha-farnesene, (3Z,6Z)-3,7,11-trimethyl-1,3,6,10-dodecatetraene.
(−)-beta-santalene isomer, (1S,2R,4R)-2-methyl-3-methylidene-2-(4-methyl-3-penten-1-yl)bicyclo[2.2.1]heptane.
beta-santalene (1S,2R,4R)-2-methyl-3-methylidene-2-(4-methyl-3-penten-1-yl)bicyclo[2.2.1]heptane.
alpha-curcumene, (+/−)-alpha-curcumene, 4-(1,5-DIMETHYL-4-HEXENYL)-1-METHYLBENZENE.
beta-curcumene, (+−)-beta-curcumene, 1-methyl-4-(6-methyl-5-hepten-2-yl)-1,4-cyclohexadiene.

The present invention provides a biochemically produced sandalwood oil comprising at least 85% santalol and bergamotol and 1% or less cis-lanceol, wherein the oil has one or more of the following features: i) 5% or less alpha-santalal, ii) 5% or less farnesol; iii) 0.5% or less spirosantalol.

As used herein the term "biochemically produced" means that the sandalwood oil of the invention is not prepared from the sandalwood tree. Rather, the sandalwood oil is biochemically produced using organisms which have been genetically engineered to generate a biochemical pathway which leads to the production of sandalwood oil of the invention. An example of genes which can to provide such a biochemical pathway is provided herein. However it should be understood that the scope of the invention also includes sandalwood oils having the claimed chemical composition and provided using other biochemical pathways, including synthetic pathways genes isolated from other species, and genes modified to produce the chemical composition of the sandalwood oil of the invention.

The invention provides a number of advantages over the prior known sandalwood oil.

As outlined in the accompanying statement in the background to the invention, due to the high value placed on sandalwood oil, the sandalwood tree has a long history of exploitation. High demand for the tree's valuable oil has resulted in over-harvesting, and consequently, the sandalwood tree is one of the most exploited groups of plants across its range. This has resulted in the sandalwood species as being considered "vulnerable" by the IUCN.

Moreover, existing methods of extracting sandalwood oil from trees requires the wood to be ground into a fine powder before the oil is extracted using a distillation process. Such methods are highly energy demanding and may also use solvents which are detrimental to the environment.

The present invention overcomes these environmental and conservation issues since the oil is prepared using genetically engineered organisms. Indeed the biochemically produced sandalwood oil of the invention is the first sandalwood oil to ever be prepared to a commercially acceptable quality using such techniques.

In addition to these clearly important environmental advantages, the sandalwood oil of the invention also has a number of surprising technical advantages over prior known sandalwood oil.

One such surprising technical advantage is that the sandalwood oil of the invention has a higher proportion of santalol and bergamotol (at least 85%) to any prior known sandalwood oil. Santalol, comprising alpha and beta santalol, and bergamotol, are key olfactory components of sandalwood oil. Furthermore, the ratio of alpha and beta santalol in the sandalwood oil of the invention respects that of the prior known sandalwood oil and thus retains the characteristic odour of the oil.

Another rising technical advantage is that the sandalwood oil of the invention has a 1% or less cis-lanceol. It is known in the art that this compound is nearly odourless (Baldovini et al (2011) Flavour and Fragrance Journal vol. 26, 7-26). Hence by having less of the odourless compound the sandalwood oil of the invention does not contain what is essentially a contaminating compound which adds no value to the overall olfactory quality of the oil.

According the sandalwood oil of the invention has environmental advantages and surprising technical advantages over prior known sandalwood oil.

Embodiments of each of the above aspects are described in further detail below. As the skilled person would understand, any features of an embodiment described which are broader than the corresponding feature in an above aspect do not apply to that aspect.

The sandalwood oil of the invention comprises at least 85% santalol and bergamotol.

By "at least 85% santalol and bergamotol" we include where there sandalwood oil of the invention comprises at least 85% santalol and bergamotol. In some embodiments the sandalwood oil comprises at least 86% santalol and bergamotol. In some embodiments the sandalwood oil comprises at least 87% santalol and bergamotol. In some embodiments the sandalwood oil comprises at least 88% santalol and bergamotol. In some embodiments the sandalwood oil comprises at least 89% santalol and bergamotol. In some embodiments the sandalwood oil comprises at least 90% santalol and bergamotol. In some embodiments the sandalwood oil comprises at least 91% santalol and bergamotol. In some embodiments the sandalwood oil comprises at least 92% santalol and bergamotol. In some embodiments the sandalwood oil comprises at least 93% santalol and bergamotol. In some embodiments the sandalwood oil comprises at least 94% santalol and bergamotol. In some embodiments the sandalwood oil comprises at least 95% santalol and bergamotol.

By "santalol" we include alpha-santalol, beta-santalol and epi-beta-santalol. Information on the structure and characteristics of these compounds are provided herein. In one embodiment of the invention the sandalwood oil comprises comprises 37-65% alpha-santalol and 13-37% beta-santalol. The sandalwood oil can also comprise 5% or less epi-beta-santalol In another embodiment of the invention the sandalwood oil comprises 37-65% alpha-santalol. In another embodiment of the invention the sandalwood oil comprises 40-65% alpha-santalol. In another embodiment of the invention the sandalwood oil comprises 45-65% alpha-santalol In another embodiment of the invention the sandalwood oil comprises 50-65% alpha-santalol In another embodiment of the invention the sandalwood oil comprises 55-65% alpha-santalol In another embodiment of the invention the sandalwood oil comprises 60-65% alpha-santalol In another embodiment of the invention the sandalwood oil comprises 37-60% alpha-santalol. In another embodiment of the invention the sandalwood oil comprises 37-55% alpha-santalol. In another embodiment of the invention the sandalwood oil comprises 37-50% alpha-santalol. In another embodiment of the invention the sandalwood oil comprises 37-45% alpha-santalol. In another embodiment of the invention the sandalwood oil comprises 37-40% alpha-santalol. In another embodiment of the invention the sandalwood oil comprises 40-60% alpha-santalol. In another embodiment of the invention the sandalwood oil comprises 45-60% alpha-santalol. In another embodiment of the invention the sandalwood oil comprises 50-60% alpha-santalol. In another embodiment of the invention the sandalwood oil comprises 50-59% alpha-santalol. In another embodiment of the invention the sandalwood oil comprises 51-59% alpha-santalol. In another embodiment of the invention the sandalwood oil comprises 52-59% alpha-santalol. In another embodiment of the invention the sandalwood oil comprises 53-59% alpha-santalol. In another embodiment of the invention the sandalwood oil comprises 54-59% alpha-santalol. In another embodiment of the invention the sandalwood oil comprises 20-37% beta-santalol. In another embodiment of the invention the sandalwood oil comprises 22-37% beta-santalol. In another embodiment of the invention the sandalwood oil comprises 24-37% beta-santalol. In another embodiment of the invention the sandalwood oil comprises 25-37% beta-santalol. In another embodiment of the invention the sandalwood oil comprises 20-35% beta-santalol. In another embodiment of the invention the sandalwood oil comprises 20-33% beta-santalol. In another embodiment of the invention the sandalwood oil comprises 20-31% beta-santalol. In another embodiment of the invention the sandalwood oil comprises 20-30% beta-santalol. In another embodiment of the invention the sandalwood oil comprises 22-30% beta-santalol. In another embodiment of the invention the sandalwood oil comprises 24-30% beta-santalol. In another embodiment of the invention the sandalwood oil comprises 25-30% beta-santalol. In another embodiment of the invention the sandalwood oil comprises 25.1-30% beta-santalol. In another embodiment of the invention the sandalwood oil comprises 0.5-10% epi-beta-santalol. In another embodiment of the invention the sandalwood oil comprises 1-4% epi-beta-santalol. In another embodiment of the invention the sandalwood oil comprises 1-3% epi-beta-santalol. In another embodiment of the invention the sandalwood oil comprises 1-2% epi-beta-santalol.

The sandalwood oil of the invention comprises at least 85% santalol and bergamotol.

Information on the structure and characteristics of bergamotol is provided herein.

In one embodiment of the invention the sandalwood oil comprises comprises 37-65% alpha-santalol and 13-37% beta-santalol and 1 to 35% bergamotol.

In one embodiment of the invention sandalwood oil comprises 1 to 35% bergamotol. In one embodiment of the invention sandalwood oil comprises 1 to 34% bergamotol. In one embodiment of the invention sandalwood oil comprises 1 to 33% bergamotol. In one embodiment of the invention sandalwood oil comprises 1 to 32% bergamotol. In one embodiment of the invention sandalwood oil comprises 1 to 31% bergamotol. In one embodiment of the invention sandalwood oil comprises 1 to 30% bergamotol. In one embodiment of the invention sandalwood oil comprises 1 to 29% bergamotol. In one embodiment of the invention sandalwood oil comprises 1 to 28% bergamotol. In one embodiment of the invention sandalwood oil comprises 1 to 27% bergamotol. In one embodiment of the invention sandalwood oil comprises 1 to 26% bergamotol. In one embodiment of the invention sandalwood oil comprises 1 to 25% bergamotol. In one embodiment of the invention sandalwood oil comprises 1 to 20% bergamotol. In one embodiment of the invention sandalwood oil comprises 1 to 15% bergamotol. In one embodiment of the invention sandalwood oil comprises 1 to 10% bergamotol. In one embodiment of the invention sandalwood oil comprises 2 to 8% bergamotol. In one embodiment of the invention sandalwood oil comprises 3 to 8% bergamotol. In one embodiment of the invention sandalwood oil comprises 4 to 8% bergamotol. In one embodiment of the invention sandalwood oil comprises 5 to 7.5% bergamotol. In one embodiment of the invention sandalwood oil comprises 5.5 to 7.5% bergamotol. In one embodiment of the invention sandalwood oil comprises 6 to 7.4% bergamotol. In one embodiment of the invention sandalwood oil comprises 6.2 to 7.3% bergamotol. In one embodiment of the invention sandalwood oil comprises 6.3 to 7.2% bergamotol.

The present invention provides a biochemically produced sandalwood oil comprising at least 85% santalol and bergamotol and 1% or less cis-lanceol. Information on the structure and characteristics of cis-lanceol is provided herein.

In one embodiment of the invention sandalwood oil comprises 0.9% or less cis-lanceol. In one embodiment of the invention sandalwood oil comprises 0.8% or less cis-lanceol. In one embodiment of the invention sandalwood oil comprises 0.7% or less cis-lanceol. In one embodiment of the invention sandalwood oil comprises 0.6% or less cis-lanceol. In one embodiment of the invention sandalwood oil comprises 0.5% or less cis-lanceol. In one embodiment of the invention sandalwood oil comprises 0.4% or less cis-lanceol. In one embodiment of the invention sandalwood oil comprises 0.3% or less cis-lanceol. In one embodiment of the invention sandalwood oil comprises 0.2% or less cis-lanceol. In one embodiment of the invention sandalwood oil comprises 0.2% or less cis-lanceol. In one embodiment of the invention sandalwood oil comprises 0.1% or less cis-lanceol. In one embodiment of the invention sandalwood oil comprises 0.05% or less cis-lanceol. In one embodiment of the invention sandalwood oil comprises 0.01% or less cis-lanceol. In one embodiment of the invention sandalwood oil comprises 0% cis-lanceol.

In one embodiment the present invention provides a biochemically produced sandalwood oil comprising 5% or less alpha-santalal. Information on the structure and characteristics of alpha-santalal is provided herein.

In one embodiment of the invention sandalwood oil comprises 4% or less alpha-santalal. In one embodiment of the invention sandalwood oil comprises 3% or less alpha-santalal. In one embodiment of the invention sandalwood oil comprises 2% or less alpha-santalal. In one embodiment of the invention sandalwood oil comprises 0.2% to 4% alpha-santalal. In one embodiment of the invention sandalwood oil comprises 0.4% to 4% alpha-santalal. In one embodiment of the invention sandalwood oil comprises 0.6% to 4% alpha-santalal. In one embodiment of the invention sandalwood oil comprises 0.2% to 3% alpha-santalal. In one embodiment of the invention sandalwood oil comprises 0.4% to 3% alpha-santalal. In one embodiment of the invention sandalwood oil comprises 0.6% to 3% alpha-santalal. In one embodiment of the invention sandalwood oil comprises 0.7% to 3% alpha-santalal.

In one embodiment the present invention provides a biochemically produced sandalwood oil comprising 5% or less farnesol. Information on the structure and characteristics of farnesol is provided herein.

In one embodiment of the invention sandalwood oil comprises 4% or less farnesol. In one embodiment of the invention sandalwood oil comprises 3% or less farnesol. In one embodiment of the invention sandalwood oil comprises 1% to 3% farnesol. In another embodiment of the invention sandalwood oil comprises 1% to 2.5% farnesol. In another embodiment of the invention sandalwood oil comprises 1% to 2.4% farnesol. In another embodiment of the invention sandalwood oil comprises 1% to 2.3% farnesol.

In one embodiment the present invention provides a biochemically produced sandalwood oil comprising 0.5% or less spirosantalol. Information on the structure and characteristics of spirosantalol is provided herein.

In one embodiment of the invention sandalwood oil comprises 0.5% or less spirosantalol. In one embodiment of the invention sandalwood oil comprises 0.4% or less spirosantalol. In one embodiment of the invention sandalwood oil comprises 0.3% or less spirosantalol. In one embodiment of the invention sandalwood oil comprises 0.2% or less spirosantalol. In one embodiment of the invention sandalwood oil comprises 0.1% or less spirosantalol. In one embodiment of the invention sandalwood oil comprises 0.05% or less spirosantalol. In one embodiment of the invention sandalwood oil comprises 0.01% or less spirosantalol. In one embodiment of the invention sandalwood oil comprises 0% spirosantalol.

By "alpha-santalol" we include both cis-alpha-santalol and trans-alpha-santalol. Information on the structure and characteristics of these compounds are provided herein.

One embodiment of the invention is wherein ratio of cis-alpha-santalol to trans-alpha-santalol is 90:1 or less. One embodiment of the invention is wherein ratio of cis-alpha-santalol to trans-alpha-santalol is 85:1 or less. In one embodiment of the invention is wherein ratio of cis-alpha-santalol to trans-alpha-santalol is 80:1 or less. In one embodiment of the invention is wherein ratio of cis-alpha-santalol to trans-alpha-santalol is 78:1 or less. In one embodiment of the invention is wherein ratio of cis-alpha-santalol to trans-alpha-santalol is 75:1 or less. In one embodiment of the invention is wherein ratio of cis-alpha-santalol to trans-alpha-santalol is 72:1 or less. In one embodiment of the invention is wherein ratio of cis-alpha-santalol to trans-alpha-santalol is 70:1 or less. In one embodiment of the invention is wherein ratio of cis-alpha-santalol to trans-alpha-santalol is 68:1 or less. In one embodiment of the invention is wherein ratio of cis-alpha-santalol to trans-alpha-santalol is 66:1 or less.

By "alpha-santalal" we include both cis-alpha-santalal and trans-alpha-santalal. Information on the structure and characteristics of these compounds are provided herein.

One embodiment of the invention is wherein the alpha-santalal is 90% or more trans-alpha-santalal. One embodiment of the invention is wherein the alpha-santalal is 92% or more trans-alpha-santalal. One embodiment of the invention is wherein the alpha-santalal is 94% or more trans-alpha-santalal. One embodiment of the invention is wherein the alpha-santalal is 96% or more trans-alpha-santalal. One embodiment of the invention is wherein the alpha-santalal is 98% or more trans-alpha-santalal. One embodiment of the invention is wherein the alpha-santalal is 99% or more trans-alpha-santalal.

In one embodiment the present invention provides a biochemically produced sandalwood oil comprising 2% or less cis-beta-sinensol. Information on the structure and characteristics of cis-beta-sinensol is provided herein.

In one embodiment of the invention sandalwood oil comprises 0.1-1.9% cis-beta-sinensol. In one embodiment of the invention sandalwood oil comprises 0.2-1.7% cis-beta-sinensol. In one embodiment of the invention sandalwood oil comprises 0.3-1.6% cis-beta-sinensol. In one embodiment of the invention sandalwood oil comprises 0.4-1.5% cis-beta-sinensol. In one embodiment of the invention sandalwood oil comprises 0.5-1.4% cis-beta-sinensol. In one embodiment of the invention sandalwood oil comprises 0.6-1.4% cis-beta-sinensol.

In one embodiment of the invention sandalwood oil is wherein at least 85% santalol and bergamotol comprises 37-65% alpha-santalol, 13-37% beta-santalol and 1 to 35% bergamotol.

In one embodiment of the invention the sandalwood oil comprises: i) 50-60% alpha-santalol, ii) 20-35% beta-santalol; iii) 5% or less alpha-santalal; iv) 5% or less farnesol; v) 0.5% or less spirosantalol; vi) 4-10% bergamotol; vii) 0-5% cis-beta-sinensol; viii) 5% or less epi-beta-santalol.

In one embodiment of the invention the sandalwood oil comprises: i) 54%-59% alpha-santalol; ii) 25.1%-30% beta-santalol; iii) 0.7%-3% alpha-santalal; iv) 1%-2.3% farnesol; v) 0.5% or less spirosantalol; vi) 6.3%-7.2% bergamotol; vii) 0.6%—1.4% cis-beta-sinensol; viii) 1-2% epi-beta-santalol.

In addition to the compounds listed above, the biochemically produced sandalwood oil may comprise additional compounds. For example, (1S,2R,4S,7R)-1,7-dimethyl-7-(4-methyl-3-penten-1-yl)bicyclo[2.2.1]heptan-2-ol, epi-beta-santalol, 5-[(3R)-2,3-dimethyltricyclo[2.2.1.0~2,6~] hept-3-yl]-2-methyl-1-pentanol, alpha-santalene, alpha-farnesene, beta-santalene isomer, beta-santalene, alpha-curcumene, beta-curcumene. Further additional compounds may also be included, not least those compounds discussed in Baldovini et al (2011) Flavour and Fragrance Journal vol. 26, 7-26.

cis-beta-sinensol, (2Z,6E)-2,6-dimethyl-10-methylidene-2,6,11-dodecatrien-1-ol and 2,3-dimethyl-3-(4-methyl-3-penten-1-yl)bicyclo[2.2.1]heptan-2-ol are new.

Hence a further aspect of the invention provides cis-beta-sinensol ((2Z,6E)-2,6-dimethyl-10-methylidene-2,6,11-dodecatrien-1-ol).

A further aspect of the invention provides 2,3-dimethyl-3-(4-methyl-3-penten-1-yl)bicyclo[2.2.1]heptan-2-ol.

Preparation of the Biochemically Produced Sandalwood Oil of the Invention

The present invention provides a biochemically produced sandalwood oil. The sandalwood oil is produced from genetically engineered organisms. As stated above the biochemically produced sandalwood oil of the invention is the first sandalwood oil to ever be prepared to a commercially acceptable quality using such techniques.

Sandalwood oil comprises different sesquiterpene alcohol compounds which contribute towards the olfactory property of the oil. The sesquiterpene alcohols are derived from terpene hydrocarbons in a multi-step enzymic process. The enzymatic synthesis of sesquiterpene alcohol compounds is known in the art. In brief, farnesyl diphosphate (FPP) is converted into, amongst other compounds, alpha- and beta-santalene via sesquiterpene synthases. They are subsequently converted to sesquiterpene alcohol compounds via cytochrome P450s.

It can be appreciated that in order to prepare the biochemically produced sandalwood oil of the invention a genetically engineered organism can be used which expresses suitable sesquiterpene synthases and cytochrome P450s. Examples of such enzymes are known in the art. For example, WO2010067309 and WO2015040197 provide details of enzymes suitable for the preparation of the biochemically produced sandalwood oil of the invention. Further sesquiterpene synthases and cytochrome P450s may include those provided in the art. For example, Jones et al, Journal of biological chemistry (2011), 286(20), 17445-54 and Srivastava et al, Scientific Reports (2015), 5, 10095 provide details of sesquiterpene synthases while Celedon et al, Plant Journal (2016), 86(4), 289-29. provide details of cytochrome P450s Moreover, it is also known in the art that the presence of a cytochrome P450-reductase (CPR) is beneficial in order to reconstitute the activity of the cytochrome P450 enzyme. Examples of such CPRs are also known in the art. For example, WO2015040197 provide details of CPRs suitable for this process.

As stated above, FPP is converted into sesquiterpenes via sesquiterpene synthases. It is possible that the biochemically produced sandalwood oil of the invention can be prepared using a method in which FPP is exogenously supplied to a suitable genetically engineered organism. However it is preferable that that organism is capable of producing FPP. Such an organism may produce FPP naturally or it does not produce FPP naturally but is transformed to produce FPP. Methods to transform organisms, for example microorganisms, so that they produce FPP are already known in the art. Such methods can for example be found in the literature, for example in the following publications: Martin, V. J., Pitera, D. J., Withers, S. T., Newman, J. D., and Keasling, J. D. Nat BiotechnoL, 2003, 21(7), 796-802 (transformation of E. coli); Wu, S., Schalk, M., Clark, A., Miles, R. B., Coates, R., and Chappell, J., Nat BiotechnoL, 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, Biotechnology and Bioengineering, 2007, 97(1), 170-181 (transformation of yeast). Examples of enzymes which can be used to produce FPP in a genetically engineered organism are provided in, for example, WO2013064411 or in Schalk et al (2013) J. Am. Chem. Soc. 134, 18900-18903.

To prepare the biochemically produced sandalwood oil of the invention, a genetically engineered organism capable of producing FPP and which expresses a suitable sesquiterpene synthase, cytochrome P450 and CPR is prepared. We provide detailed information in the examples herein of the preparation of such a genetically engineered organism, which is in no way limiting to the scope of the present invention.

Hence an aspect of the present invention provides a method of preparing a biochemically produced sandalwood oil of the invention comprising; (i) cultivating a genetically engineered organism capable of producing FPP and which expresses a suitable sesquiterpene synthase, cytochrome P450 and CPR, and (ii) isolating the biochemically produced sandalwood oil of the invention.

According to a preferred embodiment, the genetically engineered organism capable of producing FPP and which expresses a suitable sesquiterpene synthase, cytochrome P450 and CPR comprises a polypeptide having alpha and beta-santalene synthase activity having at least 55%, preferably at least 60%, preferably at least 65%, preferably at least 70%, preferably at least 75%, preferably at least 80%, preferably at least 85%, preferably at least, 90%, preferably at least, 95%, and even more preferably at least 98% identical to SEQ ID NO: 6. Preferably the genetically engineered organism also comprises a polypeptide having cytochrome P450 activity having at least 55%, preferably at least 60%, preferably at least 65%, preferably at least 70%, preferably at least 75%, preferably at least 80%, preferably at least 85%, preferably at least, 90%, preferably at least, 95%, and even more preferably at least 98% identical to SEQ ID NO: 2. Preferably the genetically engineered organism also comprises a polypeptide having CPR activity having at least 55%, preferably at least 60%, preferably at least 65%, preferably at least 70%, preferably at least 75%, preferably at least 80%, preferably at least 85%, preferably at least, 90%, preferably at least, 95%, and even more preferably at least 98% identical to SEQ ID NO: 4.

As used herein, the polypeptide is intended as a polypeptide or peptide fragment that encompasses the amino acid sequences identified herein, as well as truncated or variant polypeptides, provided that they keep their alpha and beta-santalene synthase, cytochrome P450 or CPR activity as defined above and that they share at least the defined percentage of identity with the corresponding fragment of SEQ ID NOs: 6, 2 or 4 appropriate.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

Preferably the genetically engineered organism capable of producing FPP comprises a polypeptide having alpha and beta-santalene synthase activity having the amino acid sequence as shown in SEQ ID NO: 6, a polypeptide having cytochrome P450 activity having the amino acid sequence as shown in SEQ ID NO: 2 and a polypeptide having CPR activity having the amino acid sequence as shown in SEQ ID NO: 4.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the examples.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed. There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al, Cloning Vectors: A Laboratory Manual, 1985, Elsevier, New York and Sambrook et al., Molecular Cloning: A Laboratory Manual, $2^{nd}$ edition, 1989, Cold Spring Harbor Laboratory Press. Cloning and expression vectors for higher plants and/or plant cells in particular are available to the skilled person. See for example Schardl et al. Gene 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

Preferably the genetically engineered organism capable of producing FPP comprises a nucleic acid sequence of SEQ ID NO: 5, a nucleic acid sequence of SEQ ID NO: 1 and nucleic acid sequence as shown in SEQ ID NO: 3.

To carry out the invention in vivo, the host organism or cell is cultivated under conditions conducive to the production of the sandalwood oil of the invention. Accordingly, if the host is a transgenic plant, optimal growth conditions are provided, such as optimal light, water and nutrient conditions, for example. If the host is a unicellular organism, conditions conducive to the production of biochemically produced sandalwood oil of the invention may comprise addition of suitable cofactors to the culture medium of the host. In addition, a culture medium may be selected, so as to maximize β-santalene synthesis. Optimal culture conditions are described in a more detailed manner in the following Examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism used to carry out the method of the invention in vivo is a microorganism. Any microorganism can be used but according to an even more preferred embodiment said microorganism is a bacteria or yeast. Most preferably, said bacteria is *E. coli* and said yeast is *Saccharomyces cerevisiae*.

Isolated higher eukaryotic cells can also be used, instead of complete organisms, as hosts to carry out the method of the invention in vivo. Suitable eukaryotic cells may be any non-human cell, but are preferably plant or fungal cells.

The method of the aspect of the invention includes a step of isolating the biochemically produced sandalwood oil of the invention.

Methods of isolating the biochemically produced sandalwood oil of the invention include the use of flash chromatography or distillation, as would be known to a person skilled in the art. Further information on the isolation processes which can be used are provided in the accompanying examples.

Perfume Uses

As mentioned above, the invention concerns the use of the sandalwood oil of the invention as a perfuming ingredient. In other words, it concerns a method or a process to confer, enhance, improve or modify the odor properties of a perfuming composition or of a perfumed article or of a surface, which method comprises adding to said composition or article an effective amount of the sandalwood oil of the invention, e.g. to impart its typical note. Understood that the final hedonic effect may depend on the precise dosage and on the organoleptic properties of the sandalwood oil of the invention, but anyway the addition of the sandalwood oil of the invention will impart to the final product its typical touch in the form of a note, touch or aspect depending on the dosage.

By "use of the sandalwood oil of the invention" it has to be understood here also the use of any composition containing the sandalwood oil of the invention and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, the sandalwood oil of the invention as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar (origin: Exxon Chemical) or glycol ethers and glycol ether esters such as those known under the trademark Dowanol (origin: Dow Chemical Company), or hydrogenated castors oils such as those known under the trademark Cremophor RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. Solid carriers are of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate*, origin: Mitsui Chemicals), among which a trimer of xylylene diisocyanate with trimethylolpropane and a Biuret of hexamethylene diisocyanate are preferred.

Some of the seminal literature related to the encapsulation of perfumes by polycondensation of amino resins, namely melamine based resins with aldehydes includes articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-8054.

By "perfumery base" what is meant here is a composition comprising at least one perfuming co-ingredient.

Said perfuming co-ingredient is not the sandalwood oil of the invention. Moreover, by "perfuming co ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, IO-undecenal, octanal and/or nonanal and/or nonenal;

Aromatic-herbal ingredients: eucalyptus oil, camphor, eucalyptol, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino) benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, β-menth-1-en-8-ol, 4-(1,1-dimethylethyl)-1-cyclohexyl acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyl acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl[3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one, Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl)ethoxycarbonyl]methyl propanoate;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal, A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds. also known as properfume or profragrance. Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate or a mixture thereof.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of sandalwood oil of the invention and at least one perfumery carrier consists of a particular embodiment of the invention as well as a perfuming composition comprising at least the sandalwood oil of the invention, at least one perfumery carrier, at least one perfumery base, and optionally at least one perfumery adjuvant.

According to a particular embodiment, the compositions mentioned above, comprise more than the sandalwood oil of the invention and enable the perfumer to prepare accords or perfumes possessing the odor tonality of the sandalwood oil of the invention, creating thus new building block for creation purposes The sandalwood oil of the invention can also be advantageously used in all the fields of modern perfumery, i.e. fine or functional perfumery, to positively impart or modify the odor of a consumer product into which the sandalwood oil of the invention is added. Consequently, another object of the present invention consists of by a perfumed consumer product comprising, as a perfuming ingredient, the sandalwood oil of the invention, as defined above.

The sandalwood oil of the invention can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or an after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a face mask, a skin serum, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the sandalwood oil of the invention, so that it may be necessary to protect the latter from premature decomposition, for example by encapsulation.

The proportions in which the sandalwood oil of the invention can be incorporated into the various aforementioned products or compositions vary within a wide range of values. These values are dependent on the nature of the article to be perfumed and on the desired organoleptic effect as well as on the nature of the co-ingredients in a given base when the sandalwood oil of the invention are mixed with perfuming co-ingredients, solvents or additives commonly used in the art.

For example, in the case of perfuming compositions, typical concentrations are in the order of 0.001% to 10% by weight, or even more, of the sandalwood oil of the invention based on the weight of the composition into which they are incorporated. In the case of perfumed consumer product, typical concentrations are in the order of 0.0001% to 2% by weight, preferably in the order of 0.0001% to 1% by weight, or even more, of the compounds of the formula (I) based on the weight of the consumer product into which they are incorporated.

A preferred embodiment of the invention provides a perfuming composition comprising the sandalwood oil of the invention and a synthetic sandalwood ingredient. The synthetic sandalwood ingredient may be, for example, at least one of the following compounds: (−)-(2E)-2-ethyl-4-[(1R)-2,2,3-trimethyl-3-cyclopenten-1-yl]-2-buten-1-ol; (+−)-2-ETHYL-4-(2,2,3-TRIMETHYL-3-CYCLOPENTEN-1-YL)-2-BUTEN-1-OL; 3-(BICYCLO[2.2.1]HEPT-2-YL)-1-CYCLOHEXANOL; (−)-(2R,4E)-3,3-dimethyl-5-[(1R)-2,2,3-trimethyl-3-cyclopenten-1-yl]-4-penten-2-ol (A)+(−)-(2S,4E)-3,3-dimethyl-5-[(1R)-2,2,3-trimethyl-3-cyclopenten-1-yl]-4-penten-2-ol (B); 3-[(2',2',3'-TRIMETHYL-3'-CYCLOPENTEN-1'-YL)METHOXY]-2-BUTANOL; (+)-(2S,4E)-3,3-dimethyl-5-[(1S)-2,2,3-trimethyl-3-cyclopenten-1-yl]-4-penten-2-ol (A)+(+)-(2R,4E)-3,3-dimethyl-5-[(1S)-2,2,3-trimethyl-3-cyclopenten-1-yl]-4-penten-2-ol (B); (+−)-7-METHOXY-3,7-DIMETHYL-2-OCTANOL; (2S)-2-methyl-4-[(1R)-2,2,3-trimethyl-3-cyclopenten-1-yl]-4-penten-1-ol (A)+(2R)-2-methyl-4-[(1R)-2,2,3-trimethyl-3-cyclopenten-1-yl]-4-penten-1-ol (B); (2R)-2-methyl-4-[(1R)-2,2,3-trimethyl-3-cyclopenten-1-yl]-4-pentenal (A)+(2S)-2-methyl-4-[(1R)-2,2,3-trimethyl-3-cyclopenten-1-yl]-4-pentenal (B); (1'S,3'R)-{1-METHYL-2-[(1',2',2'-TRIMETHYLBICYCLO[3.1.0]HEX-3'-YL)METHYL]CYCLOPROPYL}METHANOL. It is can be understood that the sandalwood oil of the invention would bring a naturalness, creaminess and more tenacity to the sandalwood facet.

A preferred embodiment of the invention provides a perfuming composition comprising the sandalwood oil of the invention and a musky ingredient. The musky ingredients ingredient may be, for example, at least one of the following compounds: 1-OXA-12-CYCLOHEXADECEN-2-ONE (A)+1-OXA-13-CYCLOHEXADECEN-2-ONE (B); (+−)-4,6,6,7,8,8-hexamethyl-1,3,4,6,7,8-hexahydrocyclopenta[g]isochromene; 1,4-dioxacycloheptadecane-5,17-dione; oxacyclohexadecan-2-one; (+)-(1S,1'R)-2-[1-(3',3'-DIMETHYL-1'-CYCLOHEXYL)ETHOXY]-2-METHYLPROPYL PROPANOATE; 2-{(1RS)-1-[(1SR)-3,3-dimethylcyclohexyl]ethoxy}-2-oxoethyl propionate (A)+2-{(1RS)-1-[(1RS)-3,3-dimethylcyclohexyl]ethoxy}-2-oxoethyl propionate (B)+2-oxo-2-{[(1RS,2RS)-2,6,6- trimethylcycloheptyl]oxy}ethyl propionate (C)+2-oxo-2-{[(1RS,2SR)-2,6,6-trimethylcycloheptyl]oxy}ethyl propionate (D); (+−)-(4E)-3-METHYL-4-CYCLOPENTADECEN-1-ONE (A)+(+−)-(5E)-3-METHYL-5-CYCLOPENTADECEN-1-ONE (B)+(+−)-(5Z)-3-METHYL-5-CYCLOPENTADECEN-1-ONE (C); 1,2,3,5,6,7-HEXAHYDRO-1,1,2,3,3-PENTAMETHYL-4-INDENONE; (+−)-1-(3,5,5,6,8,8-hexamethyl-5,6,7,8-tetrahydro-2-naphthalenyl)ethanone; (10E)-oxacycloheptadec-10-en-2-one; (+−)-3-methylcyclopentadecanone; 1-(4-TERT-BUTYL-3,5-DINITRO-2,6-DIMETHYLPHENYL)-1-ETHANONE. It is can be understood that the sandalwood oil of the invention would enhance the musky perception and brings more tenacity to the perfuming composition.

A preferred embodiment of the invention provides a perfuming composition comprising the sandalwood oil of the invention and a floral ingredient The floral ingredient may be, for example, at least one of the following compounds: methyl 2-((1RS,2RS)-3-oxo-2-pentylcyclopentyl)acetate; (2E)-2-benzylideneoctanal; (E)-2-PENTYL-3-PHENYL-2-PROPENAL; (−)-(3R)-3,7-DIMETHYL-1,6-OCTADIEN-3-OL; (+−)-2-methyl-3-[4-(2-methyl-2-propanyl)phenyl]propanal; 2-PHENYLETHANOL; BENZYL 2-HYDROXYBENZOATE; Cis-4-(2-methyl-2-propanyl)cyclohexyl acetate (A)+trans-4-(2-methyl-2-propanyl)cyclohexyl acetate (B); HEXYL 2-HYDROXYBENZOATE; (3Z)-3-hexen-1-yl salicylate; PENTYL 2-HYDROXYBENZOATE; (+−)-3,7-DIMETHYL-6-OCTEN-1-OL; (+−)-(3E)-3-methyl-4-(2,6,6-trimethyl-2-cyclohexen-1-yl)-3-buten-2-one (A)+(+−)-(1E)-1-(2,6,6-trimethyl-2-cyclohexen-1-yl)-1-penten-3-one (B); (+−)-3-methyl-5-phenyl-1-pentanol; (+−)-(3E)-4-(2,6,6-trimethyl-2-cyclohexen-1-yl)-3-buten-2-one; (3E)-4-(2,6,6-trimethyl-1-cyclohexen-1-yl)-3-buten-2-one; (+−)-TETRAHYDRO-2-ISOBUTYL-4-METHYL-4(2H)-PYRANOL. It is can be understood that the sandalwood oil of the invention would bring more volume and tenacity to the floral heart of the perfuming composition.

A preferred embodiment of the invention provides a perfuming composition comprising the sandalwood oil of the invention and a woody ingredient. The woody ingredient may be, for example, at least one of the following compounds: (+−)-1-(OCTAHYDRO-2,3,8,8-TETRAME-2-NAPHTHALENYL)-1-ETHANONE (DOUBLE BOND: 4A,5 (A)+4,4A (B)+4A,8A (C); patchouli oil; Clearwood®; Vertofix coeur; boisambrene forte; cedarwood oil; Cedramber; 1-[(1RS,6SR)-2,2,6-trimethylcyclohexyl]-3-hexanol; (+−)-(1-ethoxyethoxy)cyclododecane. It is can be understood that the sandalwood oil of the invention would bring more naturalness, warmth and tenacity to the woody facet and the perfuming composition.

Encapsulated Perfume

In some aspects, the biochemically produced sandalwood oil is encapsulated within a matrix material.

Without intending to be limited to any particular theory, the matrix material forms a shell, encapsulating and retaining the biochemically produced sandalwood oil. The matrix material may be permeable to the perfuming accord, and accordingly, in some aspects, the matrix material may release the retained biochemically produced sandalwood oil slowly over time, by a mechanism, such as, for example, diffusion.

Alternatively, the matrix material may be impermeable to the biochemically produced sandalwood oil of the invention. Accordingly, in some aspects, the matrix material may release the biochemically produced sandalwood oil when the encapsulating matrix material is ruptured.

The matrix material may be any material capable of retaining fragrance. Examples include core-shell type capsules composed of a polymeric rupturable external wall enclosing a perfume accord; a spray-dried matrix type wherein the matrix comprises a water-soluble material; an extrusion granulation type; and, a composite type comprising a plurality of core shell microcapsules dispersed in a spray-dry carrier.

Examples of the core-shell capsules include but are not limited to PopScent® M, PopScent® MG, PopScent® P and PolyBloom™ An example of the spray-dried capsules include but is not limited to Fircaps®.

Examples of the extrusion granulation capsules include but are not limited to Flexarome® and Durarome®.

Examples of the composite capsules include but are not limited to PopScent® M-Dry, PopScent® P-Dry and PopScent® M-Dry Plus.

Another example of a capsule suitable for use in the present disclosure are the capsules disclosed in U.S. Pat. No. 5,135,747.

Another example of a capsule suitable for use in the present disclosure are the capsules disclosed in U.S. Pat. No. 5,508,259 A.

Another example of a capsule suitable for use in the present disclosure are the capsules disclosed in U.S. Pat. No. 6,200,949 B1.

Another example of a capsule suitable for use in the present disclosure are the capsules disclosed in U.S. Pat. No. 7,208,463 B2.

Another example of a capsule suitable for use in the present disclosure are the capsules disclosed in U.S. Patent Application Publication No. 2003/0194416 A1.

Applications of the Sandalwood Oil of the Invention

It is known in the art that sandalwood oil has a number of anti-inflammatory, antimicrobial, anti-proliferative, immunomodulatory and anti-cancer properties. Hence the sandalwood oil of the invention can be used as an anti-inflammatory, antimicrobial, anti-proliferative, immunomodulatory and anti-cancer agent.

Further uses of the sandalwood oil of the invention include antihyperglycemic, antioxidant, antineoplastic, antitanning, anti-aging, and skin softening.

Hence a further aspect of the invention provides a sandalwood oil of the invention formulated for topical application. Further embodiments of this aspect of the invention are provided below.

The present inventors investigated further the anti-microbial and anti-inflammatory effects of the sandalwood oil of the invention which are discussed below.

Antimicrobial

As shown in the examples below, the sandalwood oil of the invention presented herein demonstrates antimicrobial effects.

In one aspect, the present invention provides a composition comprising the sandalwood oil of the invention, wherein the sandalwood oil is present in an amount sufficient to provide an antimicrobial effect. Preferably the composition is topically applied In another aspect, the present invention provides a composition comprising the sandalwood oil of the invention for use as antimicrobial agent. Hence in an embodiment of the invention provides the sandalwood oil of the invention for use in the treatment of a microbial infection.

In another aspect, the present invention provides method of treating a microbial infection comprising administering an effective amount of the composition sandalwood oil of the invention to a recipient in need thereof.

By "antimicrobial", we include that the sandalwood oil of the invention can be used as an antibacterial, anti-viral and anti-fungal composition. In this context, the term "treatment" is intended to include where the composition sandalwood oil of the invention alleviates or relieves the microbial infection by, for example, killing the microbial cells and/or preventing the spread of the microbial cells and/or inhibiting the growth and reproduction of the cells.

For example, the sandalwood oil of the invention can be used in the treatment of infections caused by fungal dermatophytes and yeasts including *Trichophyton, Microsporum* and *Candida*

The sandalwood oil of the invention can be used in the treatment of infections caused by viral agents including herpes simplex viruses-1 and -2 and the influenza virus, human papillomavirus (HPV) warts and mulluscipox viruses.

In one aspect, the composition provides the antimicrobial effect by inhibiting the growth of bacteria.

The bacteria may be a gram positive or a gram negative bacterium.

For example, bacteria against which the sandalwood oil of the invention is effective may include Firmicutes, which may be Bacilli or Clostridia, for example *Clostridium botulinum*.

In a preferred embodiment, bacteria against which the sandalwood oil of the invention is effective may include Bacillales, preferably, *Staphylococcus*, for example, *Staphylococcus aureus*. Additional Bacillales with which the sandalwood oil of the invention is effective include Streptococci, for example, *Streptococcus pyogenes* or *Streptococcus pneumoniae*.

Further examples of bacteria against which the sandalwood oil of the invention is effective may include Pseudomonadales, preferably, *Pseudomonas aeruginosa*. Further examples of bacteria against which the sandalwood oil of the invention is effective may include Gammaproteobacteria, which may be independently selected from a group consisting of Enter obacteriales, *Proteus, Serratia*, Pasteurellales, and Vibrionales. Preferred Enterobacteriales include *Escherichia*. Preferred *Proteus* include *Proteus mirabilis*. Preferred *Serratia* include *Serratia marcescens*. Preferred Pasteurellales include *Haemophilus influenzae*. Preferred Vibrionales include *Vibrio cholerae*.

Further examples of bacteria against which sandalwood oil of the invention is effective may include Betaproteobacteria, including Neisseriales, for example, *Neisseria gonorrhoeae*. Further examples of bacteria against which the sandalwood oil of the invention is effective may include Delta/epsilon subdivided Proteobacteria, including Campylobacterales, for example *Helicobacter pylori*. Further examples of bacteria against which sandalwood oil of the invention is effective may include Actinobacteria, for example *Mycobacterium tuberculosis* and *Nocardia asteroides*.

Further examples of gram positive bacteria include *Micrococcus flavus, Micrococcus glutamicus*, Cuticubacterium *acnes* (*Propionibacterium acnes*) and members of the Propionibacteriaceae, *Sarcina lutea, Staphylococcus albus, Staphylococcus epidemidis, Staphylococcus equisimili*.

Further examples of gram negative bacteria include *Acinetobacter baumannii, Acinetobacter calcoaceticus, Klebsiella aerogenes, Klebsiella pneumonia, Pseudomonas aeruginosa, Pseudomonas florescens, Pseudomonas putida*.

Further examples of yeasts and fungi include *Candida albicans, Candida krusei, Epidermophyton fluccosum, Epidemophyton inguinale, Microsporum canis, Microsporum gypseum, Trichophyton asteroids, Trichophyton interdigitale, Trichophyton mentaprophytes, Trichophyton purpureum*.

In one aspect, the present invention provides a method, comprising treating a substrate comprising microbes with a composition comprising the sandalwood oil of the invention, in an amount effective to provide an antimicrobial effect.

In some aspects, the present disclosure provides a use, or a method of use of a composition comprising the sandalwood oil of the invention wherein the sandalwood oil of the invention is present in an amount sufficient to provide an antimicrobial effect.

By the term "antimicrobial effect", it is meant the normal meaning in the art; i.e. an agent which kills microorganism or inhibits their growth.

In some aspects, the composition used in the present disclosure comprises sandalwood oil of the invention in an amount above 25 ppm, alternatively in an amount between 25 ppm and 10000 ppm, alternatively in an amount between 40 ppm and 5000 ppm. Alternatively, the composition comprises sandalwood oil of the invention in an amount between 40 ppm and 500 ppm; or in an amount between 40 ppm and 300 ppm. Alternatively the composition comprises sandalwood oil of the invention in an amount between 40 ppm and 200 ppm, alternatively in an amount between ppm and 100 ppm. Alternatively, the composition comprises 40 ppm, 50 ppm, 300 ppm or 7000 ppm of sandalwood oil of the invention.

The use of the compositions as defined here-in is particularly advantageous to limit or control the growth of microorganism including bacteria, fungi, and yeasts. The antimicrobial effect is one of the main requirements of hygiene products such as body care or home care products.

As mentioned above, the disclosure concerns the use of the composition comprising the sandalwood oil of the invention as defined above as an antimicrobial agent.

In some aspects, the present disclosure provides a non-therapeutic method of affecting microbial activity, the method comprising treating a substrate comprising microbes with a composition comprising the sandalwood oil of the invention, wherein the substrate is treated with the composition in an amount sufficient to provide an antimicrobial effect.

In some aspects, the present disclosure provides a non-therapeutic method of affecting microbial activity, the method comprising treating a substrate comprising microbes with a composition comprising sandalwood oil of the invention, wherein the substrate is treated with the composition in an amount sufficient to provide an antimicrobial effect.

Anti-Inflammatory and Moisturizing

As shown in the examples below, the sandalwood oil of the invention presented herein demonstrated an anti-inflammatory effect on cellular types well-known to be relevant for skin physiology. The sandalwood oil of the invention also has a skin moisturizing benefit.

The data demonstrates that sandalwood oil of the invention, through its propensity to reduce pro-inflammatory burden and to enhance the epidermal barrier integrity and by establishing a functional protection against external threats, represents a treatment strategy to prevent skin inflammation and to repair epidermal barrier dysfunction, such as observed in various skin inflammatory pathologies and atopic dermatitis.

Also, since the sandalwood oil of the invention enhance the epidermal barrier integrity, then the composition of the invention also has a skin moisturizing benefit.

Hence a further aspect of the invention provides a composition comprising the sandalwood oil of the invention, wherein the sandalwood oil is present in an amount sufficient to provide an anti-inflammatory effect and/or moisturizing effect. Preferably the inflammation to be treated is a skin inflammation, and the composition is topically applied.

In another aspect, the present invention provides a composition comprising the sandalwood oil of the invention for use as anti-inflammatory agent and/or moisturizing agent. Hence in an embodiment of the invention provides the sandalwood oil of the invention for use in the treatment of an inflammatory condition and/or increase skin moisturizing.

In another aspect, the present invention provides method of treating an inflammatory condition and/or to increase skin moisturizing comprising administering an effective amount of the composition sandalwood oil of the invention to a recipient in need thereof.

By "anti-inflammatory and/or moisturizing effect" we include where the sandalwood oil of the invention can be used for the treatment, including alleviation, of eczema, psoriasis, seborrheic and atopic dermatitis and other such skin disorders.

In some aspects, the composition used in the present disclosure comprises sandalwood oil of the invention in an amount above 1 µg/ml, alternatively in an amount above 5 µg/ml. Alternatively, the composition comprises sandalwood oil of the invention in an amount above 10 µg/ml; or in an amount above 15 µg/ml. Alternatively, the composition comprises sandalwood oil of the invention in an amount above 20 µg/ml.

The use of the compositions as defined here-in is particularly advantageous to limit or control inflammation on a subject.

As mentioned above, the disclosure concerns the use of the composition comprising the sandalwood oil of the invention as defined above as an anti-inflammatory agent.

The composition comprising the sandalwood oil of the invention can be combined in this aspect of the invention with one or more further anti-inflammatory or analgesic compounds including non-steroidal anti-inflammatory drugs, cyclooxygenase-2 selective inhibitors, salicylates, steroids, opioids, anesthetics, and naturally derived and synthetic soothing agents with anti-inflammatory properties. The composition comprising the sandalwood oil of the invention can be combined also with cooling agents. For example, the at least one ingredient having analgesic properties may be selected from a group consisting of ibuprofen, naproxen, ketoprofen, piroxicam, indomethacin, diclofenac, nimesulide, celecoxib, valdecoxib, acetyl salicylic acid, cortisone, prednisone, morphine, fentanyl, lidocaine, prilocaine, bupivacaine, benzocaine, tetracaine, dibucaine, paracetamol, acetaminophen, evening primrose oil, borage seed oil, black currant seed oil, cannabinoids, felbinac, nicotinate esters, capsaicin, amitriptyline, glyceryl trinitrate, menthol, camphor, pimecrolimus, phenytoin, benzyl alcohol, ethyl chloride hexylresorcinol, trolarnine, pramoxine, proparacaine, almond oil, aloe vera, castor oil, eucalyptus oil, grapeseed oil, peppermint oil, tea tree oil, or turmeric.

Anti-Acne

In one embodiment of the invention, the sandalwood oil of the invention is used in the treatment of acne.

It can be appreciated that the combination of anti-microbial and anti-inflammatory effects of the sandalwood oil of the invention therefore provides evidence of its effectiveness for the treatment of acne. Indeed, the sandalwood oil of the invention can act to prevent new lesions. It also can have a synergistic effect with existing anti-acne active treatments. Moreover the sandalwood oil of the invention can alleviate side effects (in conjunction with emollient and moisturizing properties).

In a further embodiment of the invention the composition may comprise one or more anti-acne agents. Preferably, the further anti-acne agent is selected from desquamators, keratolytics, comedolytics, exfoliants and emollients, such as squalane and others. Desquamators, keratolytics, comedolytics and exfoliants aid in the penetration of the active into the skin, and compounds which are capable of serving one or more of these functions are well known in the art. A compound may have one or more of these properties, for example a desquamator may also act as a keratolytic.

The further anti-acne agent is preferably selected from one or more of benzoyl peroxide, isoprenylcysteine and derivatives, niacinamide, alpha-OH acids, lipo-OH acids, retinol-based products, linoleic acid, lauric acid, zinc, EPA (eicosapentaenoic), alpha-linolenic, DHA (docosahexaenoic) acid, resorcinol, resorcinol monoacetate, sulfur, salicylic acid, derivatives of salicylic acid having one or more ($C_1$ to $C_{12}$) alkyl and/or ($C_1$ to $C_{12}$) alkoxy groups on the aromatic ring (e.g., 5-n-octyl salicylic acid, 5-n-octanoyl salicylic acid and 2-hydroxy-3-methoxybenzoic acid), phenol, cresol, metacresyl acetate, lactic acid, glycolic acid, pyruvic acid, malic acid, urea, N-acetyl cysteine, retinoic acid, retinol, retinyl esters and combinations of retinol and retinyl esters with retinoid boosters. Retinoid boosters are compounds that mimic the effect of retinoic acid on skin by enhancing the conversion of retinol or retinyl esters to retinoic acid. Retinoid boosters may be used singly or as combinations of two or more compounds. Retinoid boosters are described in WO 02/02074, the contents of which are incorporated herein by reference. Specific retinoid boosters include, for example, ceramides, phosphatidyl choline, linoleic acid, 12-hydroxystearic acid and climbazole.

When used for topical application the composition comprising the sandalwood oil of the invention can be used in association perfuming components. Examples of such components include mixtures of natural and synthetic aromatic substances. Natural aromatic substances may include extracts of flowers (lily, lavender, rose, jasmine, neroli, ylang-ylang), stems, and leaves (geranium, patchouli, petitgrain), fruits (anise, coriander, caraway, juniper), fruit skins (bergamot, lemon, orange), roots (cumin, angelica, celery, cardamom, costus, iris, calmus), woods (pine, sandal, guaiac, cedar, rosewood), herbs and grasses (tarragon, lemon grass, sage, thyme), needles and branches (spruce, pine), resins and balms (galbanum, elemi, benzoin, myrrh, olibanum, opoponax). Animal-derived raw materials, e.g., civet and castoreum, may also be used. Typical synthetic aromatic compounds are products of the type of esters, ethers, aldehydes, ketones, alcohols, and hydrocarbons. Aromatic compounds of the type of esters include, e.g., benzyl acetate, phenoxxethyl isobutyrate, β-tert-butylcyclohexyl acetate, linalyl acetate, dimethylbenzylcarbinyl acetate, phenylethyl acetate, linalyl benzoate, benzyl formiate, ethylmethylphenyl glycinate, allylcyclohexyl propionate, styrallyl propionate, and benzyl salicylate. Ethers include, e.g., benzylethylethers, aldehydes include, e.g., the linear alkanals with 8-18 carbon atoms, citral, citronellal, citronellyl oxyacetaldehyde, cyclamenaldehyde, hydroxycitronellal, lilial, and bourgeonal, ketones include, e.g., a-isomethylionone and methylcedrylketone, alcohols include, e.g., anethol, citronellol, eugenol, isoeugenol, geraniol, linalool, phenylethyl alcohol and terpineol, and hydrocarbons primarily include terpenes and balms. In one aspect, the perfume is a mixture of various aromatic substances that, together, generate an appealing fragrance. Etheric oils with lower volatility, which are mostly used as aromatic components, are suitable as perfume oils, e.g., sage oil, camomile oil, clove oil, balm oil, mint oil, cinnamon leaf oil, lime blossom oil, juniper berry oil, vetiver oil, olibanum oil, galbanum oil, labdanum oil, and lavandin oil, bergamot oil, dihydromyrcenol, lilial, lyral, citronellol, phenylethyl alcohol, a-hexylcinnamic aldehyde, geraniol, benzyl acetone, cyclamen aldehyde, Boisambrene Forte, ambroxan, indol, hedione, sandelice, lemon oil, mandarin oil, orange oil, allylamyl glycolate, cyclovertal, lavandin oil, muscatel sage oil, 13-damascone, geranium oil, bourbon, cyclohexyl salicylate, Vertofix Coeur, Iso-E-Super, Fixolide NP, Evernyl, I raldein gamma, phenylacetic acid, geranyl acetate, benzyl acetate, rose oxide, romilate, irotyl, and floramate, alone or in mixtures, are used.

The term "dermatologically-acceptable," as used herein, means that the components so described are suitable for use in contact with human skin without undue toxicity, incompatibility, instability, allergic response, and the like. Remington's Pharmaceutical Sciences Ed. by Gennaro, Mack Publishing, Easton, Pa., 1995 discloses various carriers used in formulating pharmaceutical compositions and known techniques for the preparation of such dosage forms.

The dermatologically-acceptable carriers used can be water or aqueous solutions; oils, such as triglycerides of capric or of caprylic acid, or castor oil; fats, waxes and other natural and synthetic fatty materials, preferably esters of fatty acids with alcohols of low C number, e.g. with isopropanol, propylene glycol or glycerol, or esters of fatty alcohols with alkanoic acids of low C number or with fatty acids; alcohols of low C number, and also their ethers, preferably ethanol, isopropanol, glycerol, ethylene glycol, ethylene glycol monoethyl or monobutyl ether, propylene glycol monomethyl, monoethyl or monobutyl ether, diethylene glycol monomethyl or monoethyl ether and analogous products. In some cases, mixtures of the abovementioned solvents are used. In the case of alcoholic solvents, water can be a further constituent.

Some specific examples of dermatologically-acceptable carriers suitable for application with the invention include water, olive oil, peanut oil, sesame oil, sunflower oil, safflower oil, arachis oil, coconut oil, liquid paraffin, polyethyleneglycol, ethanol, propanol, isopropanol, glycerol, fatty alcohols, triglycerides, polyvinyl alcohol, partially hydrolysed poly vinyl acetate. Other suitable carriers would be appreciated by one having ordinary skill in the art.

The carrier component may comprise oils, which in one embodiment are present in the oil phase of an emulsion, selected from hydrocarbon oils such as paraffin or mineral oils; b) waxes such as beeswax or paraffin wax; c) natural oils such as sunflower oil, apricot kernel oil, shea butter or jojoba oil; d) silicone oils such as dimethicone, cyclomethicone or cetyldimethicone; e) fatty acid esters such as isopropyl palmitate, isopropyl myristate, dioctylmaleate, glyceryl oleate and cetostearyl isononanoate; f) fatty alcohols such as cetyl alcohol or stearyl alcohol and mixtures thereof (eg cetearyl alcohol); g) polypropylene glycol or polyethylene glycol ethers, e.g. PPG-14 butyl ether; or h) mixtures thereof, for example, the blend of waxes available commercially under the trade name Cutina (Cognis).

The carrier can be in the form of a hydroalcoholic system (e.g. liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semi-solids (such as gels and sticks); and aqueous based mousse systems. Non-limiting examples of the topical carrier systems useful in the present invention are described in the following four references, all of which are incorporated herein by reference in their entirety: "Sun Products Formulary", Cosmetics & Toiletries, Vol. 105, pp.

Various embodiments of the compositions of the invention may include a stabilizing agent. The stabilizing agent may be an antioxidant selected from the group consisting of amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotenoids, carotenes (e.g. α-carotene, β-carotene, lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa- or hepta-thioninesulphoxime) in very low tolerable doses (e.g. pmol to .mu.mol/kg), further (metal) chelators (e.g. .alpha.-hydroxy fatty acids, palmitic acid, phytic acid, lactoferrin), alpha.-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate) and coniferyl benzoate from benzoin, rutic acid and its derivatives, ferulic acid and its derivatives, butyl hydroxytoluene, butylhydroxyanisole, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide) and the derivatives suitable according to the invention (salts, esters, ethers, sugars, nucleotides, nucleosides, peptides and lipids) of these said active compounds. The stabilizing agent may be present at a concentration of from 0.2-3.0%.

The composition according to the invention may comprise one or more moisturising agents, i.e. ingredients intended to increase the water content of the top layers of the skin. Examples of such ingredients are emollients, such as squalane, glycerin, 1,3-butylene glycol, propylene glycol, urea, panthenol, a-hydroxy acids such as lactic acid, hydrolysed proteins, hyaluronic acid, pyrrolidone carbonic acid, as well as naturally-occurring materials such as aloe barbadensis. Other suitable ingredients include glycerol quat, glycerol and hydroxyethyl urea and include the Stratys-3 system sold by the company Unilever or those sold under the name Sheer Infusion. The moisturising agents will generally be water-soluble moisturising agents.

The compositions of the present invention can also include a thickening agent. Suitable thickening agents include cellulose and derivatives thereof such as carboxymethylcellulose hydroxyethylcellulose, cellulose acetate propionate carboxylate, hydroxyethylcellulose, hydroxyethylmethylcellulose, hydroxypropylcellulose, hydroxypropyl methylcellulose, methyl hydroxyethylcellulose, microcrystalline cellulose, sodium cellulose sulfate, and mixtures thereof. Further suitable thickening agents include alkyl substituted celluloses. In these polymers a proportion of the hydroxy groups of the cellulose polymer are hydroyxalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful for modifying the hydroxyalkyl cellulose include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof.

Other thickening agents suitable for use with the compositions of the invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Gels provided according to the invention may be aqueous or non-aqueous. Aqueous gels are preferred. The gel will contain a gelling agent in order to give sufficient viscosity to the gel. A particularly suitable gelling agent is a copolymer of acryloyl dimethyl tauric acid (or a salt thereof), especially a copolymer of that monomer with another vinylic monomer. The salt may be a salt of a Group I alkali metal, but is more preferably an ammonium salt. Examples of suitable copolymer gelling agents are ammonium acryloyl dimethyl taurate/vinyl pyrrolidone copolymer, ammonium acryloyl dimethyl taurate/Beheneth-25 methacrylate copolymer, ammonium acryloyldimethyltaurate/vinyl formamide copolymer. These materials are available from Clariant GmbH in the range of products under the trade name Aristoflex.

Preferred aqueous systems comprise water in an amount of at least 40% w/w, more preferably at least 50% w/wt, most preferably at least 60% w/w. Some compositions may contain at least 70% or even at least 75% w/w. The upper limit of water will depend on the amounts of other ingredients incorporated in the composition so that the water may form the remainder of the composition up to 100% w/w of the composition. A typical maximum value is less than 90% w/w, for example less than 85% or 80% w/w.

Compositions according to the invention may further include preservatives. Suitable preservatives include, but are not limited to, $C_1$-$C_3$ alkyl parabens and phenoxyethanol, calcium propionate, sodium nitrate, sodium nitrite, sulfites (sulfur dioxide, sodium bisulfite, potassium hydrogen sulfite, etc.) and disodium EDTA. Preservatives are typically present in an amount ranging from about 0.5% to about 2.0% by weight percent, based on the total composition.

In one embodiment of the invention the composition may include an anti-inflammatory agent. Examples of anti-inflammatory agents, include, but are not limited to, non-steroidal and steroidal anti-inflammatory agents such as corticosteroids such as hydrocortisone, hydroxyltriamcinolone, alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene, (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, and triamcinolone, and combinations thereof. Examples of non-steroidal anti-inflammatory agents include but not limited to COX inhibitors, LOX inhibitors, and p38 kinase inhibitors, immunosuppresant agents such as cyclosporin, and cytokine synthesis inhibitors. Other natural antiinflammatories include, but are not limited to, extracts of feverfew, soy, or oats, beta-glucan, and totarol.

In a further embodiment of the invention the composition may comprise one or more anti-acne agents. Preferably, the further anti-acne agent is selected from desquamators, keratolytics, comedolytics, non-comedolytics and exfoliants. Desquamators, keratolytics, comedolytics and exfoliants aid in the penetration of the active into the skin, and compounds which are capable of serving one or more of these functions are well known in the art. A compound may have one or more of these properties, for example a desquamator may also act as a keratolytic.

Arthropod Control

The present inventors investigated the potential of the sandalwood oil of the invention as an arthropod repellant. As shown in the accompanying examples, the composition can be used as a mosquito or tick repellant.

Hence a further aspect of the invention provides an arthropod control composition comprising the sandalwood oil of the invention.

Arthropods in the present invention's understanding relate to undesired arthropods, meaning that their presence in the air, on the surface of an article, the surface of a plant or the surface of an animal. The animal may be a bird (e.g. a chicken and the arthropod is a tick), a fish (e.g. a salmon and the arthropod is a louse), a vertebrate, such as a human subject or other mammal, preferably human subject. The preferably undesired arthropods are pest arthropods that impact plants and animals, e.g. thrips, ticks, aphids, beetles, moth, mealybug, scale etc., more preferably pest arthropods that impact animals, e.g. ants, termites, cockroaches, flies, etc., even more preferably blood feeding arthropods that impact vertebrates, e.g. biting fly, bed bug, kissing bug, flea, lice, mosquitos and ticks, even more preferably mosquitos and ticks.

The reason why the presence of an arthropod is not desired might be that the arthropod's presence in the air is unpleasant to a subject, the contact of an arthropod on an article transfers diseases and/or germs or the arthropod bites an organism and causes itching, the transmission of diseases and/or germs or the arthropod feeding may be the cause for other diseases and/or conditions.

In a particular embodiment, the arthropod is an insect or an arachnid, preferably an insect.

The term "insect" has the normal understanding by a skilled person the technical field. An insect is described by a well-defined head, thorax, and abdomen, only three pairs of legs, and typically one or two pairs of wings.

In a particular embodiment, the insect is a mosquito, biting fly, bedbug, kissing bug, flea, lice, ant, termite, cockroach, fly, aphid, beetle, thrip, tick, moth, mealybug or scale bug, more preferably a mosquito.

The term "arachnid" has the normal understanding by a skilled person the technical field. An arachnid is described having a segmented body divided into two regions of which the anterior bears four pairs of legs but no antennae.

In a particular embodiment, the arachnid is a tick, mite, chigger or spider, more preferably a tick.

The expression "control", "arthropod control", "insect control" or "arachnid control" or the like has the normal meaning for a skilled person in the technical field.

"Controlling" in the context of the present invention defines the ability of an arthropod controlling composition according to the present invention to attract, deter, inactivate, limit the development and/or reproduction or repel an arthropod, preferably deter or repel an arthropod and even more preferably repel an arthropod "Attracting" according to the present invention defines the ability of an arthropod attractant composition according to the invention to increase or encourage contact or the presence of an arthropod at the arthropod attractant source, such as in the air, on the surface of an article or on the surface of an vertebrate, such as a human subject or other mammal, preferably an article such as a trapping device, the arthropod attractant compound or composition has been applied to.

"Deterring" according to the present invention defines the ability of an arthropod deterrent composition according to the invention to minimize, reduce, discourage or prevent contact or the presence of an arthropod at the arthropod deterrent source, on the surface of an article or on the surface of an vertebrate, such as a human subject or other mammal, preferably human subject, to which the arthropod deterrent compound or composition has been applied to. Typically, the deterrent effect is shown when used as feeding deterrent hindering a pest from subsequent food intake or oviposition after an initial tasting of the arthropod deterrent compound or composition.

"Repellency" according to the present invention defines the ability of an arthropod repellent composition according to the present invention to minimize, reduce, discourage or prevent approach or the presence of an arthropod at the arthropod repellent source, such as in the air, on the surface of an article or on the surface of an vertebrate, such as a human subject or other mammal, preferably human subject, to which the arthropod repellent compound or composition has been applied to.

In a particular embodiment, the arthropod control composition is an arthropod repelling composition, preferably an insect repelling composition, more preferably a mosquito repelling composition.

In a particular embodiment, the arthropod controlling source is the surface and/or the air in the vicinity of an article, preferably a candle, coil, electric diffuser, wristband, patch, collar, ear tag, clothes, fabrics, papers, biochar, cardboard, cellulosic pads, bed nets, screen, curtains, furniture, walls, ground or paint, or the surface of a subject, preferably the surface of a vertebrate, such as a human subject or other mammal, preferably human subject, i.e. the skin of a human subject treated with a product such as spray, aerosol, cream, roll on, wristband, lotion, soap, shampoo, sunscreen or patch or a cloth treated with a product such as laundry powder, fragrance booster, softener, liquid detergent, spray, lotion, powder, liquid detergent, spray, lotion, powder.

In a particular embodiment, the arthropod control composition comprises sandalwood oil of the invention when present in the composition, in an amount of 0.1 mg/ml to 50 mg/ml, preferably in an amount of 0.2 mg/ml to 40 mg/ml, in an amount of 0.3 mg/ml to 30 mg/ml, in an amount of 0.4 mg/ml to 20 mg/ml, in an amount of 0.4 mg/ml to 10 mg/ml.

In one embodiment, the arthropod control composition may further comprise an arthropod control co-ingredient. By "arthropod control co-ingredient" is understood an ingredient capable of imparting additional arthropod controlling benefits to the arthropod controlling effect of the composition herein described.

In one embodiment, the arthropod control composition may further comprise perfume ingredients. Perfume ingredients are understood as contributing, modifying, enhancing or improving the olfactory character of the composition but does not contribute to, enhance or improve the arthropod controlling effect of the composition.

The arthropod control composition can further comprise a carrier. By "carrier" is understood a material with which the active compound is mixed or formulated to facilitate its application a locus or other object to be treated, or its storage, transport and/or handling. Said carrier may be of inorganic or organic or of synthetic natural origin. Said carrier may be a liquid or a solid.

The following examples are illustrative only and are not meant to limit the scope of the invention as set forth in the specification

EXAMPLES

Example 1: Preparation of the Sandalwood Composition of the Invention in Engineered *E. coli* Cells Codon optimized cDNAs encoding for an N-terminal variant of the *Santalum album* cytochrome P450 SaCP816 (WO2015040197), a mint cytochrome P450 reductase (CPRm) and a α-santalene/β-santalene synthase (SaSAS) (WO2010067309) were designed and synthetized for optimal expression in *E. coli*.

The optimized cytochrome P450 and cytochrome P450 reductase cDNAs were first combined with to prepare a bi-cistronic construct containing successively the P450 cDNA a linker sequence including a ribosome binding site (RBS) and the CPRm cDNA. This construct was prepared by PCR by amplifying the two cDNAs with 5' and 3' overhangs suitable for cloning using the In-Fusion® procedure (Clontech) in the NdeI-HindIII sites of the pCWori+ expression vector (Barnes H. J (1996) *Method Enzymol.* 272, 3-14) providing the plasmid pCWori-SaCP816-CPRm. The codon optimized α-santalene/β-santalene synthase cDNA was then amplified and ligated using the In-Fusion® Dry-Down PCR Cloning Kit in the HindIII enzyme recognition site of pCWori-SaCP816-CPRm providing the vector pCWori- SaCP816-CPRm-SaSAS.

A second expression vector was constructed for the expression of an heterologous mevalonate pathway and production of increased amount of farnesyl diphosphate (FPP) as described previously for example in patent WO2013064411 or in Schalk et al (2012) *J Am. Chem. Soc.* 134, 18900-18903. Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in-vitro (DNA2.0, Menlo Park, CA, USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP.

The *E. coli* KRX cells (Promega) were co-transformed with the pCWori-SaCP816-CPRm-SaSAS and pACYC-29258-4506. Transformed cells were selected on carbenicillin (50 µg/ml) and chloramphenicol (34 µg/ml) LB-agar plates. Single colonies were used to inoculate 5 mL of LB medium supplemented with appropriate antibiotics. Cultures were incubated overnight at 37° C. and 250 rpm. The next day 2 mL of TB medium in glass culture tubes containing 100 µg/L carbenicilin and 17 µg/L chloramphenicol, were inoculated with 200 µl of the LB pre-culture and incubated at 37° C. and 250 rpm. After 6 hours of cultivation (or when the optical density at 600 nm of the culture reach a value of 3, the culture were cooled down to 20° C. and the expression of the proteins was induced with 0.1 mM IPTG (Isopropyl β-D-1-thiogalactopyranoside) and 0.1% Rhamnose, and 75 µg/L 6-aminolevulinic acid (sigma) and 5% (v/v) of decane were added. After 48 h incubation with 250 rpm shaking, the whole culture broth was extracted with 1 volume of MTBE (Methyl tert-butyl ether, Sigma) and analyzed by GCMS on an Agilent 6890 Series GC system connected to an Agilent 5975 mass detector. The GC was equipped with 0.25 mm inner diameter by 30 m DB-5 ms capillary column (Agilent J & W). The carrier gas was He at a constant flow of 1 mL/min. The initial oven temperature was 80° C. (1 min hold) followed by a gradient of 20° C./min to 260° C. and 40° C./min to 300° C. The identification of the products was based on the comparison of the mass spectra and retention indices with authentic standards and internal databases.

In these conditions several sesquiterpene hydrocabons, α-santalene, β-santalene, trans-α-bergamotene and epi-β-santalene were produced as well as the corresponding sesquiterpene alcohols (E)-α-santalenol, (E)-β-santalol, (E)-α-bergamotol and (E)-epi-β-santalol (FIG. 1A). The presence of sesquiterpene hydrocarbons in addition of the sesquiterpene alcohols shows that in these conditions the conversion by the cytochrome p450 monooxygenase is incomplete. The sesquiterpene hydrocarbons can be removed using for example flash chromatography. This technique can be implemented at different scales. A microscale separation can be performed using disposable Pasteur pipettes. Glass wool is wedged inside the narrow end of the pipette and silica Gel is then poured into the pipette from the wide end. A thin layer of sand is added atop the silica and the column is equilibrated with heptane. The sesquiterpene mixture produced using the transformed *E. coli* cells was dried down, suspended in heptane and loaded on the column. The column was washed with two volumes of heptane and the sesquiterpene alcohols are eluted with one volume of a mixture of 40:60 (v:v) MTBE:heptane. The resulting sample contains a mixture of (E)-α-santalol, (E)-β-santalol, (E)-α-bergamotol and (E)-epi-β-santalol (FIG. 1B).

In additional to the flash chromatography protocol outlined above, it can be understood that the skilled person can also use fractional distillation methods to remove sesquiterpene hydrocarbons from the crude solution produced by the fermentation process and to provide the sandalwood oil of the invention.

Example 2: Analysis of the Sandalwood Oil of the Invention

Provided below is a method for analyzing the composition of the sandalwood oil of the invention Samples were diluted at 3% in dichloromethane and injected on GC/MS-FID. GC/MS-FID analysis was performed on an Agilent system equipped with two columns connected to two detectors, a mass spectrometer and a FID detector. It was equipped with two Agilent DB-1MS columns (60 m×0.25 mm×0.25 µm). 0.2 µL sample was injected at 250° C. in split mode (1:50). The initial oven temperature was maintained at 50° C. for 5 min, increased to 120° C. at 3° C./min, increased to 250° C. at 5° C./min, held for 5 min, increased to 310° C. at 15° C./min and then stayed for 20 min at that temperature.

Mass spectra were generated at 70 eV at a scan ranging from m/z: 29-250 from 0 to 20 min and 29-450 from 20 min. Linear retention indexes (LRI) were determined after injection of a series of n-alcanes ($C_5$-$C_{31}$) under similar conditions. GC-MS peaks were identified and integrated using Mass Hunter software with Search Review add in and the MS library. Quantitative analysis was performed by GC-FID using methyl octanoate as internal standard and Relative Response Factor was applied for each compound.

Example 3: Dermatological Effects of the Sandalwood Composition of the Invention

INTRODUCTION

The present inventors investigated the dermatological effects of the sandalwood oil of the invention. In particular, they investigated the (i) anti-microbial properties and (ii) anti-inflammatory properties of the composition of the invention.

For both kinds of analysis, a first study determined the non-cytotoxic concentration(s) of the composition to be used in the respective adapted in vitro model.

Material and Methods

The Sandalwood Oil of the Invention

A sample of the sandalwood oil of the invention was prepared using the method outlined in Example 1 above.

Cyto-Toxicity Assay

A preliminary study was performed in order to determine the non-cytotoxic working concentrations for both the sandalwood oil of the invention and a reference sandalwood oil. The cell viability was evaluated using the standard MTS assay (3-(4,5-dimethythiazol-2-yl)-5-(3-carboxy-methoxyphenyl)-2-(4-sulfophenyl)-2H-tetrazolium) after treatment with the test ingredients (160-80-40-20-10 µg/ml, tested in triplicate).

The test was performed both under basal conditions (i.e. without pro-inflammatory challenge) and pro-inflammatory stimuli for either 24 h-72 h or 26 h, respectively. Cells were seeded in 24-wells plates with complete medium, 24 h before treatment.

Test ingredients were solubilized in solvent (DMSO or ethanol) and applied to the culture medium of cells 2 hours prior to the pro-inflammatory challenge (when required). SDS at 0.008% or 0.08% was used as cytotoxicity positive control to validate the experiment on NHEKs keratinocytes or NHDFs fibroblasts, respectively.

Minimal Inhibitory Concentration

This test determines the lowest concentration of ingredient that can inhibit the growth of a specific bacterial strain. The method used is according to Rey et al. Comb Chem High Throughput Screen. 2014; 17 (7):614-2

Cell Culture

Monolayer cultures of Normal Human foreskin-derived Dermal Fibroblasts (NHDFs; ATCC, CRL-2522) were used for the anti-inflammatory study. The cells were grown in Dulbecco's Modified Eagle Medium (DMEM, Gibco/Life Technologies, 31885) supplemented with 10% of Foetal Bovine Serum (FBS, Gibco/Life Technologies, 10270) and antibiotics (penicillin/streptomycin, Gibco/Life Technologies, 15140). Monolayer cultures of Normal Human Epidermal Keratinocytes (NHEKs; Lonza, 00192906) were used for the anti-inflammatory study. The cells were grown in Epilife medium containing gentamycin and HKGS (Human Keratinocyte Growth Supplement).

The cells were maintained in a humidified incubator at 37° C. with a 5% $CO_2$ atmosphere for the indicated treatment periods before performing metabolic, cytokine and gene expression assays.

Anti-Inflammatory Test

Both NHEK and NHDF cell types were cultured in 24-well plates for 24 h in complete medium before being exposed to the test and reference items. Test compositions were applied on the cells 2 h before the 24 h-challenge with pro-inflammatory agents (see table below). Each sample was compared to solvent control conditions. At the end of treatment, all the supernatants were collected and stored at −20° C. until further use in specific ELISA assays for the quantification of the extracellular release of IL-8, IL-6, TNF-α, MCP-1 and CXCL5, based on a standard curve, according to the kits supplier's specifications.

Figure 2:
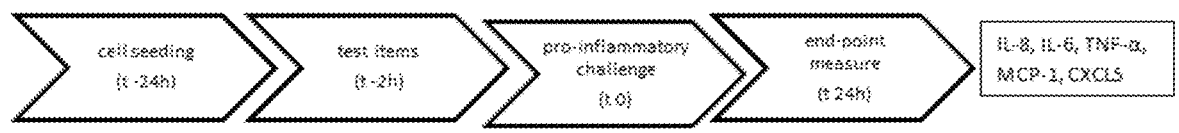
FIG. 2: Workflow for the measurement of cytokines release by NHDF and NHEK cells under pro-inflammatory challenge.

The materials used are listed in Table 1. A schematic of the experimental procedure is shown in FIG. 2.

TABLE 1

| | Concentration | Solvent | Supplier | Reference |
|---|---|---|---|---|
| Pro-inflammation Agent | | | | |
| Lipopolysaccharides (LPS) | 0.5 ug/ml | Water | Sigma Aldrich | L2630 |
| Phorbol myristate acetate (PMA) | 10 ng/ml | DMSO | | 79346 |
| Calcium ionophore A23187 | 2 uM | DMSO | | C7522 |
| Tumor necrosis factor alpha (TNFalpha) | 50 ng/ml | PBS-0.1% BSA | R&D Systems | 210-TA-020 |
| Anti-inflammatory control | | | | |
| Dexamethasone | 10 uM | Water | Sigma | D2915 |
| Ibuprofen (sodium salt) | 100-500 uM | Water | Aldrich | I1892 |

Results

Cytotoxicity

In order to ensure experiments would be carried out with test composition concentrations that are non-cytotoxic, a cytotoxicity study was performed on NHEK and NHDF after 26 h of treatment (2 h alone and 24 h under inflammatory challenge with LPS for NHDFs fibroblasts and PMA/calcium ionophore or TNF-α for NHEKs).

SDS at 0.08% and 0.008% was used as cytotoxic positive control in order to validate the experiment and the threshold of cytotoxicity was arbitrarily fixed at 80% of viability, as compared to the untreated control.

Figure 3A:
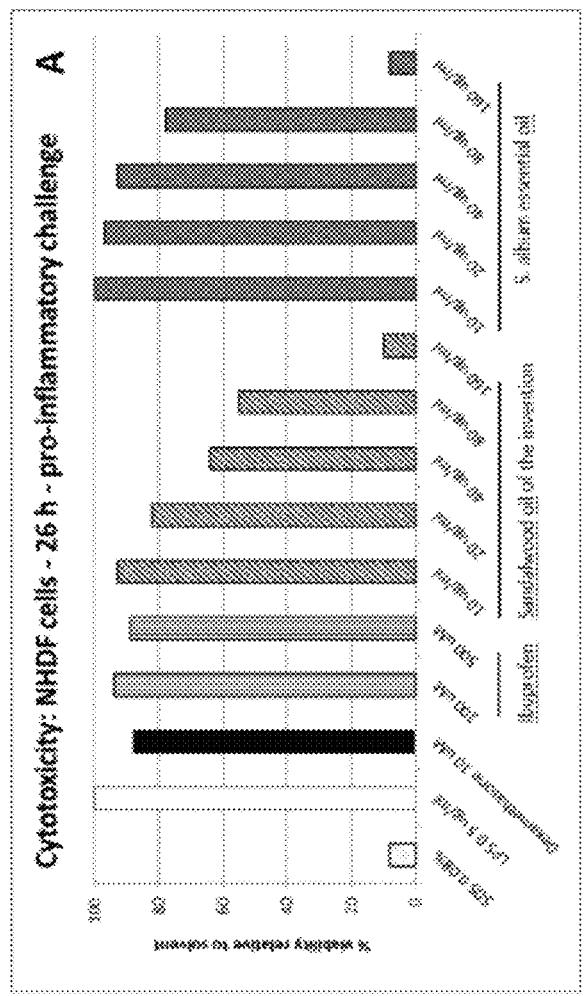
FIGS. 3A-3C: Viability of NHDF (A) and NHEK (B and C) cells under different pro-inflammatory challenges when treated with sandalwood oil of the invention and *S. album* essential oil for 26 hours. Cell viability was measured using the standard MTS assay. Each condition was measured in triplicate. In all panels—columns 4 and 5 are ibuprofen; columns 6 to 10 are sandalwood oil of the invention; columns 11 to 15 are *S. album* essential oil.
Figure 3B:
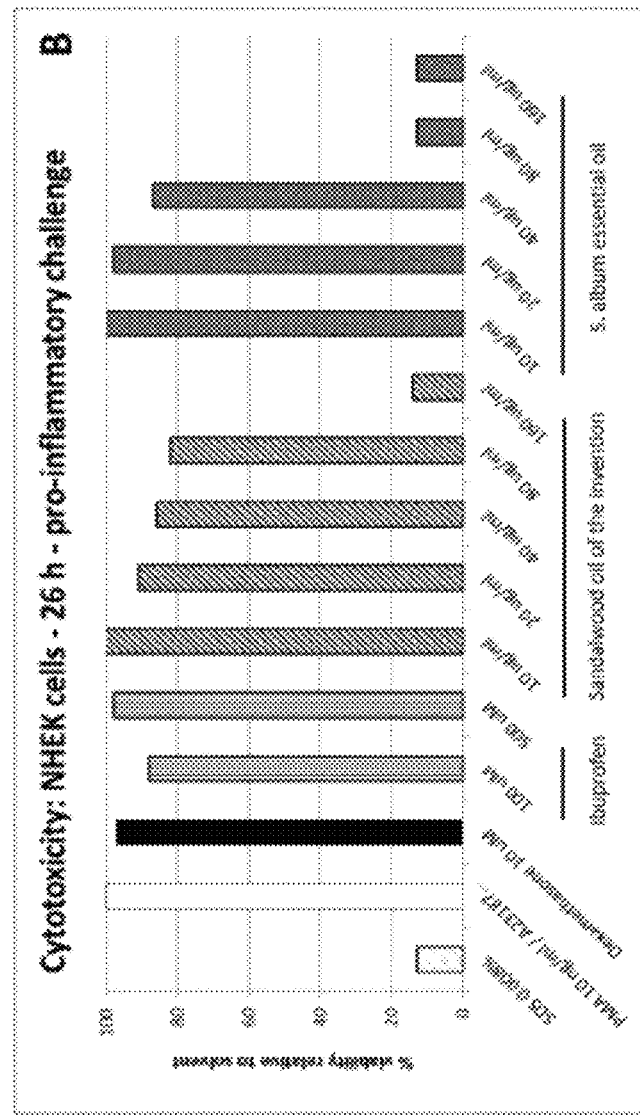
Figure 3C:
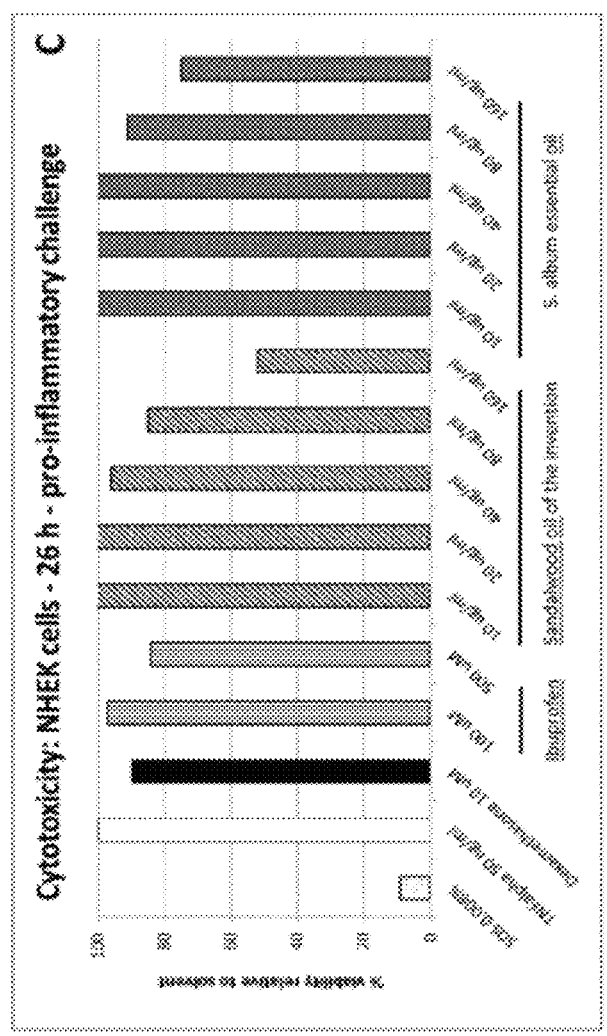

The results (FIGS. 3A-3C) obtained are expressed in percentage of viability relative to the relevant control in inflammatory condition (LPS for NHDFs fibroblasts and PMA/A23187 or TNF-α for NHEKs keratinocytes).

As expected, the positive reference SDS (0.08% and 0.008%) induced a strong decrease in cell viability after 26 h of application on both NHDFs fibroblasts and NHEKs keratinocytes. The application or the two test items (reference sandalwood oil and the sandalwood oil of the invention) at their lowest tested doses do not appear to be associated with an alteration of the cell viability exceeding 20%, as showed by results similar to that of the inflamed cell controls.

In line with these results, the concentration of 20 μg/ml for both reference sandalwood oil and the composition of the invention were selected to pursue the anti-inflammatory analysis.

To determine non-cytotoxic concentrations of composition of the invention on NHEKs under basal conditions (i.e. without inflammation challenge), the effect of 5 concentrations of test material on viability of NHEKs keratinocytes after 24 h and 72 h of treatment were measured.

The data are expressed in percentage of viability relative to the solvent control condition (ethanol 0.02% and 0.16%), arbitrarily set at 100%. The cytotoxicity threshold was fixed by convention at 80% of viability. SDS 0.008% was used as positive reference of cytotoxicity and validated the experiment.

Figure 4:
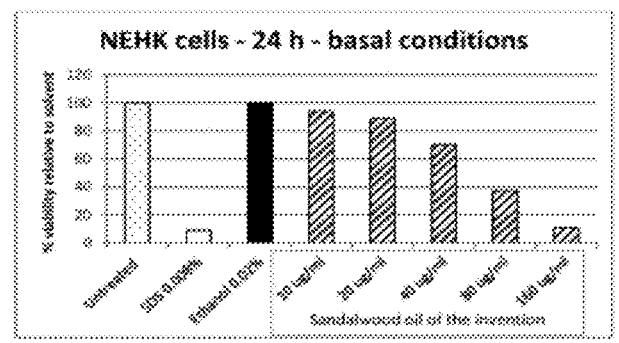
FIG. 4: Viability of NHEK cells under basal culturing conditions when exposed to sandalwood oil of the invention for 24 and 72 hours. Cell viability was measured using the standard MTS assay, with each condition performed in triplicate.
Figure 4:
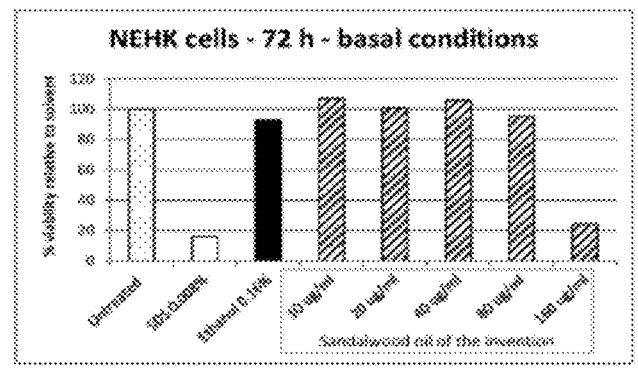

The results (FIG. 4) show that doses of 10, 20 and 40 μg/ml of biochemically-derived sandalwood do not alter significantly the viability of NHEK cells cultured under basal conditions, the latter concentration at least for the 72-hours time-point.

Anti-Inflammatory Effect of Composition of the Invention

Sandalwood oil of the invention was tested at 20 μg/ml on both keratinocytes and fibroblasts, in a comparison with *S. album* essential oil. Keratinocytes and fibroblasts were cultivated under conditions that stimulate the onset of inflammation. After induction of an inflammation state and test compounds application, cell culture supernatants were collected for further ELISA quantification. The ability of the ingredients in reducing the production of selected inflammation markers (MCP-1, CXCL5, IL-6, IL-8 and TNFalpha for NHEK only) was then measured by ELISA (Enzyme-Linked ImmunoSorbent Assay), a biochemical assay commonly used to quantify substances.

As can be seen from the accompanying Table 2, the data demonstrate that treating NHEK cells with PMA (combined with calcium ionophore A23187) or with TNF-α induces a significant release of all the tested inflammation mediators. In these conditions, the known antiinflammatories dexamethasone (with the exception of CXCL-5) and ibuprofen reduced significantly the secretion levels of mediators of inflammation.

TABLE 2

Anti-inflammatory properties of sandalwood oil of the invention. The ability of sandalwood oil of the invention to reduce the release of cytokines (MCP-1, CXCL-5, IL-6, IL-8 and TNFalpha) was measured in human fibroblast and keratinocytes challenged with pro-inflammatory stimuli. Anti-inflammatory drugs (Dexamethasone and Ibuprofen) were used as controls. The efficacy of sandalwood oil of the invention was compared to that of a traditional essential oil, extracted from S. album. The data reported represent the average of 3 replicates

| | NHDF | | | | | | | |
|---|---|---|---|---|---|---|---|---|
| | MCP-1 | | CXCL-5 | | IL-6 | | IL-8 | |
| SAMPLE | % Stimulation (vs Untreated) | % Reduction (vs LPS/EtOH) | % Stimulation (vs Untreated) | % Reduction (vs LPS/EtOH) | % Stimulation (vs Untreated) | % Reduction (vs LPS/EtOH) | % Stimulation (vs Untreated) | % Reduction (vs LPS/EtOH) |
| Untreated | 100 | NA | 100 | NA | 100 | NA | 100 | NA |
| Ethanol 0.02%/LPS 0.5 ug/ml | 1393 | 0 | 3619 | 0 | 22237 | 0 | 12783 | 0 |
| Dexamethasone 10 uM | 1067 | −23 | 6414 | 77 | 6606 | −70 | 7738 | −39 |
| Ibuprofen 100 uM | 1342 | −4 | 2929 | −19 | 16853 | −24 | 11037 | −14 |
| Ibuprofen 500 uM | 950 | −32 | 2216 | −39 | 11977 | −46 | 8242 | −36 |
| Sandalwood oil of the invention 20 ug/ml | 971 | −30 | 2995 | −17 | 13660 | −39 | 11335 | −11 |
| S. album essential oil 20 ug/ml | 881 | −37 | 3106 | −14 | 14461 | −35 | 12654 | −1 |

| | NHEK | | | | | | | | | |
|---|---|---|---|---|---|---|---|---|---|---|
| | MCP-1 | | CXCL-5 | | IL-6* | | IL-8* | | TNFα* | |
| SAMPLE | % Stimulation (vs Untreated) | % Reduction (vs TNFa/EtOH) | % Stimulation (vs Untreated) | % Reduction (vs TNFa/EtOH) | % Stimulation (vs Untreated) | % Reduction (vs A23187/EtOH) | % Stimulation (vs Untreated) | % Reduction (vs PMA + A23187/EtOH) | % Stimulation (vs Untreated) | % Reduction (vs PMA + A23187/EtOH) |
| Untreated | 100 | NA | 100 | NA | 100 | NA | 100 | NA | 100 | NA |
| Ethanol 0.02%/TNFa 50 ng/ml (or *PMA 10 ng/ml + A231872 uM) | 3031 | 0 | 434 | 0 | 611 | 0 | 19850 | 0 | 78319 | 0 |
| Dexamethasone 10 uM | 1432 | −53 | 1525 | 251 | 275 | −55 | 14801 | −25 | 33869 | −57 |
| Ibuprofen 100 uM | 2471 | −18 | 337 | −22 | 462 | −24 | 16034 | −19 | 55645 | −29 |
| Ibuprofen 500 uM | 1126 | −63 | 229 | −47 | 202 | −67 | 12190 | −39 | 12099 | −85 |
| Sandalwood oil of the invention 20 ug/ml | 2340 | −23 | 332 | −24 | 354 | −42 | 13122 | −34 | 47003 | −40 |
| S. album essential oil 20 ug/ml | 2522 | −17 | 315 | −27 | 347 | −43 | 14544 | −27 | 51984 | −34 |

Both the biochemically produced sandalwood oil of the invention and the reference Sandalwood oil significantly decreased the production of all inflammation markers.

The results presented herein demonstrate that the biochemically produced sandalwood oil of the invention significantly reduced the quantity of inflammation markers produced by keratinocytes.

Such reduction was comparable to that observed when the S. album essential oil was used.

Similarly to what observed on keratinocytes, on fibroblasts, the sandalwood oil of the invention reduced all inflammation markers.

Hence the above data demonstrates that the sandalwood oil of the invention reduces the production of inflammation mediators in human keratinocytes in vitro, and therefore supports the application of the composition as an anti-inflammatory agent.

Biological Significance of Measured Inflammation Markers

Interleukin 6 (IL-6): promptly and transiently produced in response to infections and tissue injuries, contributes to host defense through the stimulation of acute phase responses, hematopoiesis, and immune reactions The data presented in Table 3 below show an antibacterial activity on Gram positive bacterial species.

TABLE 3

| | Sandalwood oil of the invention | | | | | | |
|---|---|---|---|---|---|---|---|
| Strain | E. coli ATCC 25922 | S. aureus ATCC 6538 | S. epidermidis ATCC 14990 | S. hominis DSM 20328 | S. haemolyticus DSM 20263 | C. xerosis ATCC 373 | C. striatum DSM 20668 |
| MIC (ppm) | >10000 | 44 | 51 | 77 | 77 | 7067 | 590 |
| Solvent | ethanol | ethanol | ethanol | ethanol | ethanol | ethanol | ethanol |
| Atmosphere | aerobic | aerobic | aerobic | aerobic | aerobic | aerobic | aerobic |

| Strain | C. jeikeium K411 | C. tuberculostearicum C9 | C. acnes DSM 1897 | C. acnes Ana 22 | C. acnes Ana 20.1 |
|---|---|---|---|---|---|
| MIC (ppm) | 590 | 590 | 296 | 51 | 51 |
| Solvent | ethanol | ethanol | DMSO | DMSO | DMSO |
| Atmosphere | aerobic | aerobic | anaerobic | anaerobic | anaerobic |

Interleukin 8 (IL-8) is an important mediator of the innate immune system response. IL-8, also known as neutrophil chemotactic factor, has two primary functions. It induces chemotaxis in target cells, primarily neutrophils but also other granulocytes, causing them to migrate toward the site of infection. IL-8 also stimulates phagocytosis once they have arrived.

Monocyte chemoattractant protein-1 (MCP-1) is one of the key chemokines that regulate migration and infiltration of monocytes/macrophages. Migration of monocytes from the blood stream across the vascular endothelium is required for routine immunological surveillance of tissues, as well as in response to inflammation.

CXCL5 is well known to have chemotactic and activating functions on neutrophil, mainly during acute inflammatory responses. CXCL5 levels are also known to be elevated in some chronic inflammatory conditions (for example, atherosclerosis) without having a neutrophil infiltration role Tumor necrosis factor alpha (TNF-alpha) is one of the cytokines responsible to initiate the inflammation acute phase reaction in response to infection or disease.

Antibacterial Activity of the Composition of the Invention

The present inventors investigated the anti-microbial properties of the sandalwood oil of the invention. As outlined in the materials section above, the determined the MIC value of the composition was determined for a number of bacterial species. The MIC (minimal inhibitory concentration) measures the minimal concentration of a substance that can prevent bacterial growth. The lower the MIC the strongest is the antimicrobial activity. The testing protocol was described by Rey, S, et al. "High throughput screening of perfumery raw materials for antimicrobial properties" *Comb. Chem. High Throughput Screen.* 2014; 17(7):614-622.

The bacterial species tested are associated with different properties/benefits:

*S. aureus* is an opportunistic pathogen normally present on skin. This bacterium is normally not problematic but it can became pathogenic if the individual has an underlying condition. This bacterium has also been recently implicated in skin disorders such as atopic dermatitis. The sandalwood oil of the invention is very active on this bacterium *C. xerosis, C. striatum, C. jeikeium, C. tuberculostearicum* and *S. haemolyticus* are bacteria associated with the production of sweat body odor

*C. acnes* (formerly classified as *P. acnes*) is the causative agent of acne. The sandalwood oil of the invention is very active on this bacterium.

The antimicrobial activity on *C. acnes*, together with the anti-inflammatory action reported above, indicate a potential of the sandalwood oil of the invention for alleviation of acne symptoms.

Conclusions from the Experiments

The sandalwood oil of the invention had a number of clear properties which are of dermatological benefit.

Cell treatment with sandalwood oil of the invention alleviates the inflammation burden when applied at least at 20 µg/ml for 26 h. This reflects its potential benefit effect on skin biology, promoting its maintenance to homeostasis and protection against environmental stress and pathogens.

Therefore, sandalwood oil of the invention, through its propensity to reduce pro-inflammatory burden, represents a treatment strategy to prevent skin inflammation and to, such as observed in various skin inflammatory pathologies and atopic dermatitis.

Moreover the sandalwood oil of the invention has a clear antimicrobial activity. One of the bacterial species tested, *C. acnes*, is the causative agent of acne. Therefore, sandalwood oil of the invention shows clear potential application for the treatment of acne.

Example 4: Insect and Arthropod Repellent Effects of the Sandalwood Oil of the Invention The inventors investigated the potential of the sandalwood oil of the invention as an insect and arthropod repellent.

The repellent effect was determined on ticks (*Ixodes ricinus*) using an adaptation of the Warm Plate assay as defined in Kröber T, Bourquin M, Guerin P M. A standardised in vivo and in vitro test method for evaluating tick repellents. *Pesticide Biochemistry and Physiology.* 2013; 107(2):160-168, adapted in reducing the size of the arena and adding a controlled temperature and humid air flow to the set-up.

Figure 5:
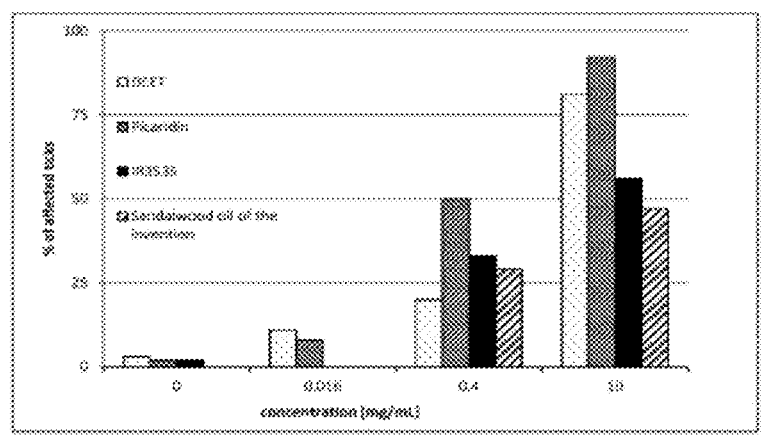
FIG. 5: Dose-response of sandalwood oil of the invention on ticks repellency (*Ixodes ricinus*) using a test adapted from Kröber T. et al. *Pesticide Biochemistry and Physiology.* 2013; 107(2):160-168.

The data for arthropod repellency is shown in FIG. 5 and Table 4 below.

TABLE 4

| | concentration [mg/mL] | % of affected ticks |
|---|---|---|
| DEET (N,N-diethyl-meta-toluamide) CAS: 134-62-3 | 0 | 3% |
| | 0.016 | 11% |
| | 0.4 | 20% |
| | 10 | 81% |
| Picaridin (sec-butyl 2-(2-hydroxyethyl) piperidine-1-carboxylate) CAS: 119515-38-7 | 0 | 2% |
| | 0.016 | 8% |
| | 0.4 | 50% |
| | 10 | 92% |
| IR3535 (Ethyl butylacetylaminopropionate) CAS: 52304-36-6 | 0 | 2% |
| | 0.016 | 0% |
| | 0.4 | 33% |
| | 10 | 56% |
| Sandalwood oil of the invention | 0 | 0% |
| | 0.016 | 0% |
| | 0.4 | 29% |
| | 10 | 47% |

The data presented herein show an increasing number of ticks being affected at increasing concentrations of the sandalwood oil of the invention (29% and 47% at 0.4 mg/ml and 10 mg/ml, respectively) at an efficacy comparable to that of IR3535, a known arthropod repellent.

Hence the data presented herein shows the sandalwood oil of the invention can be used as an arthropod repellent.

Data Obtained in a Laboratory Set-Up Known as "Warm Body Assay"

This experimental test measures the efficacy of compositions to repel blood-hungry female mosquitoes, using heat as a bait and $CO_2$ as an activator of mosquito host-seeking behavior. The assay is described by Kröber T, Kessler S, Frei J, Bourquin M, Guerin P M. 2010. An In Vitro Assay for Testing Mosquito Repellents Employing a Warm Body and Carbon Dioxide as a Behavioral Activator. *J. of the American Mosquito Control Association;* 26(4):381-386.

Figure 6:
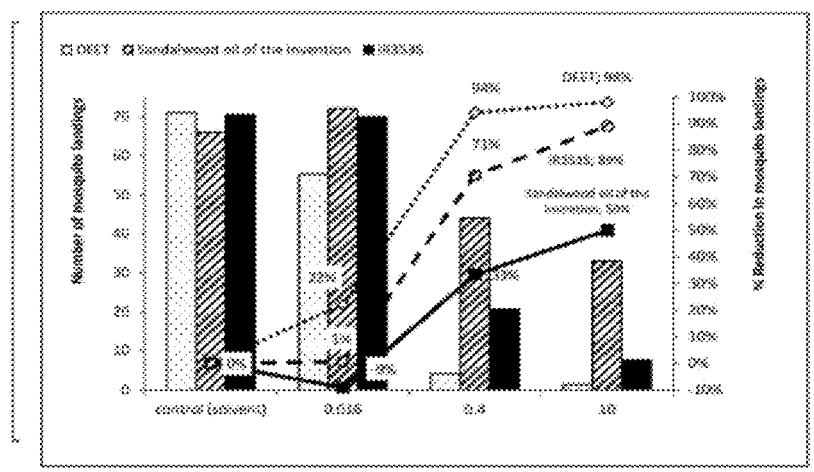
FIG. 6: Dose-response of sandalwood oil of the invention on mosquito repellency (*A. aegyptii*), measured using the Warm Body Assay as described by Kröber T. et al. *J. of the American Mosquito Control Association* (2010), 26 (4):381-386.
Figure 7A:
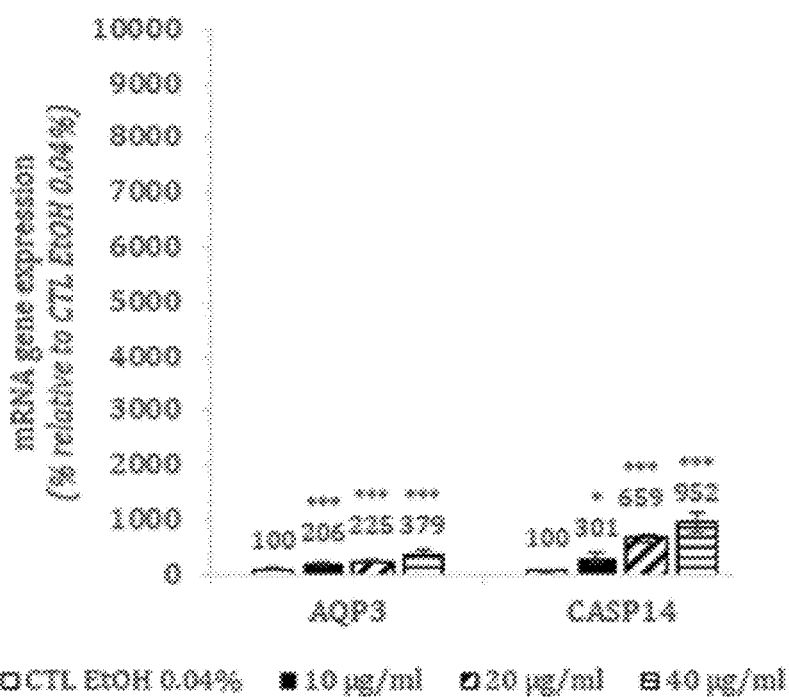
FIGS. 7A-7F: Effect the transcription of selected mRNAs in NHEKs cells treated with sandalwood oil of the invention at 10, 20 and 40 µg/ml
Figure 7B:
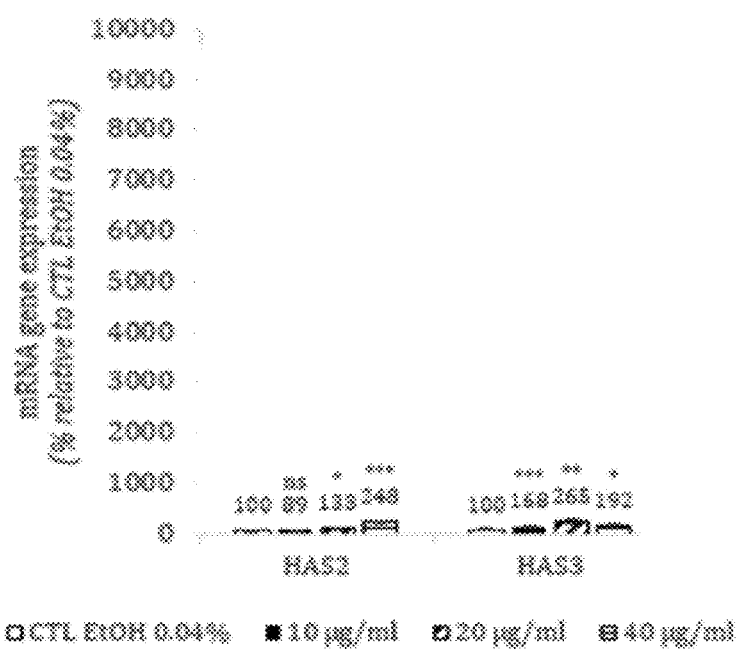
Figure 7C:
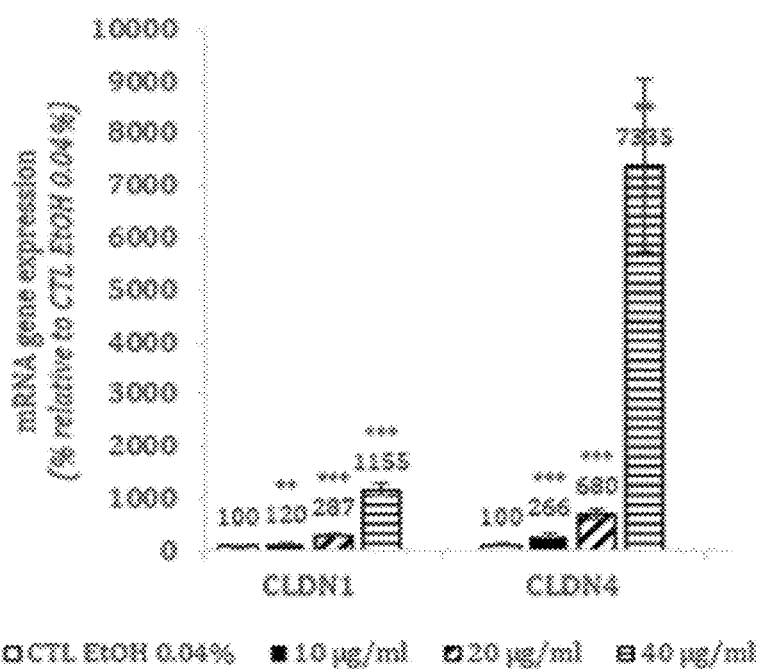
Figure 7D:
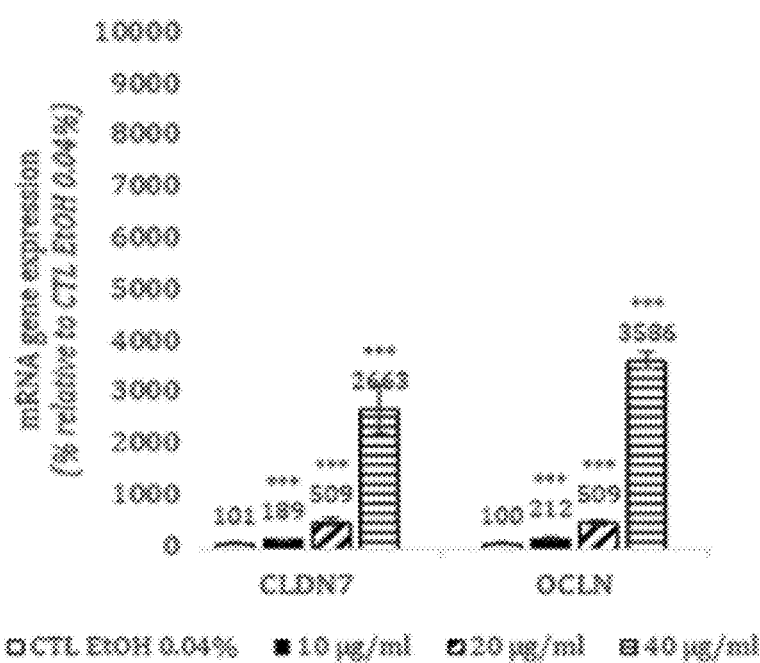
Figure 7E:
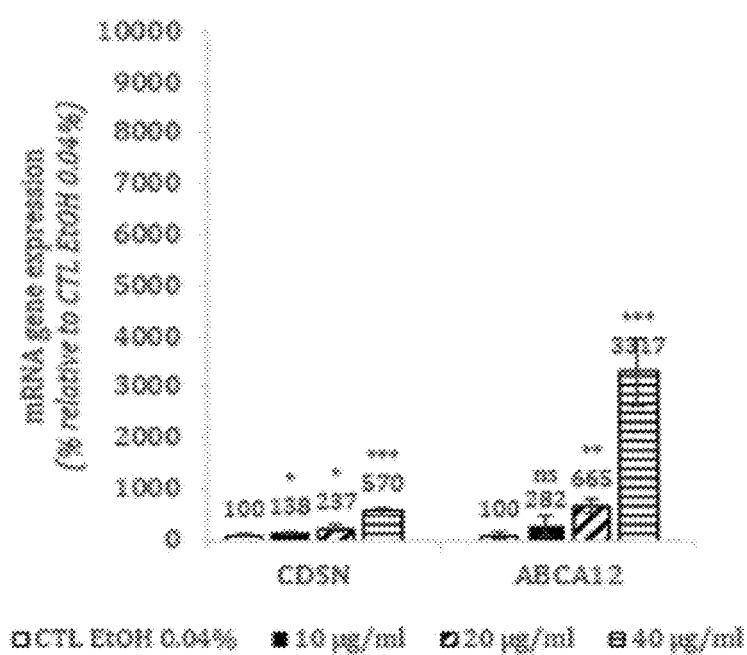
Figure 7F:
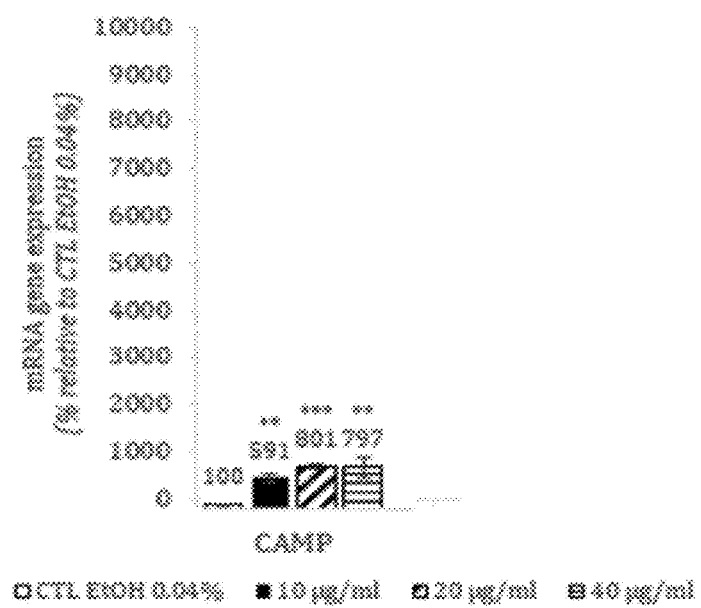
Figure 8A:
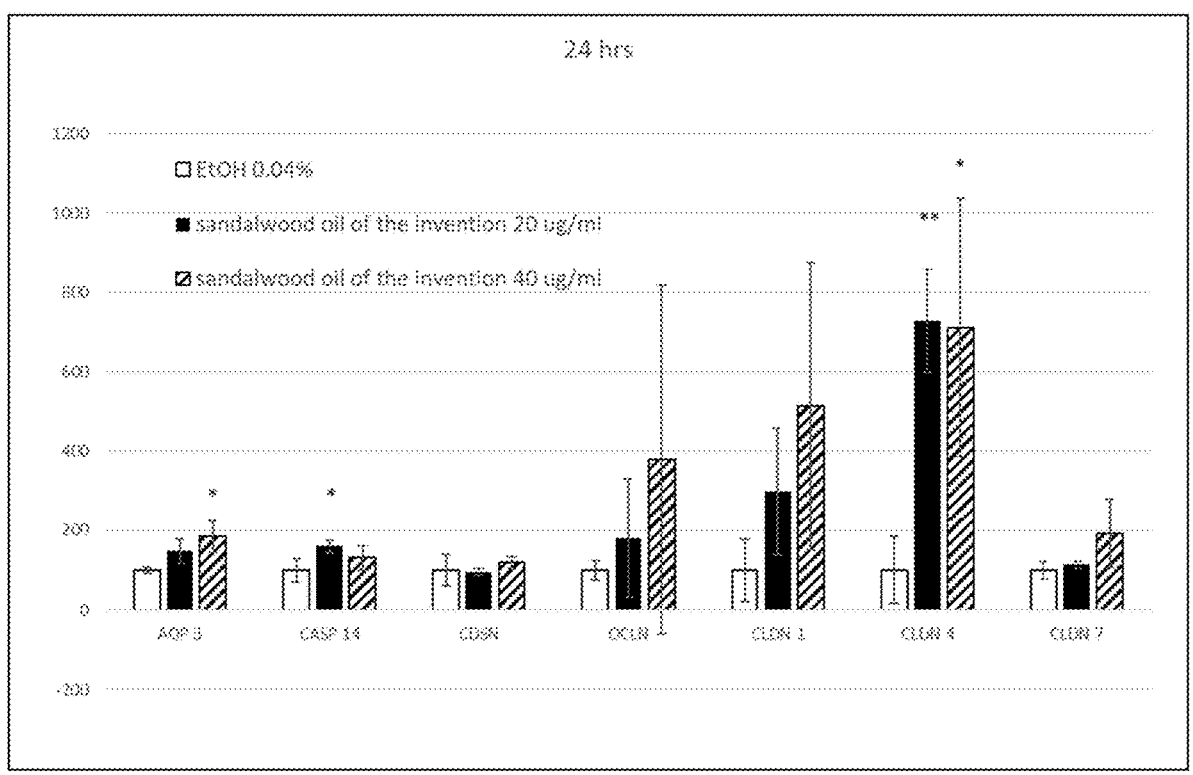
FIG. 8: Effect of sandalwood oil of the invention at 20 and 40 µg/ml on protein expression in NHEKs cells at 24 and 72 hrs (FIGS. 8A and 8B, respectively)
Figure 8B:
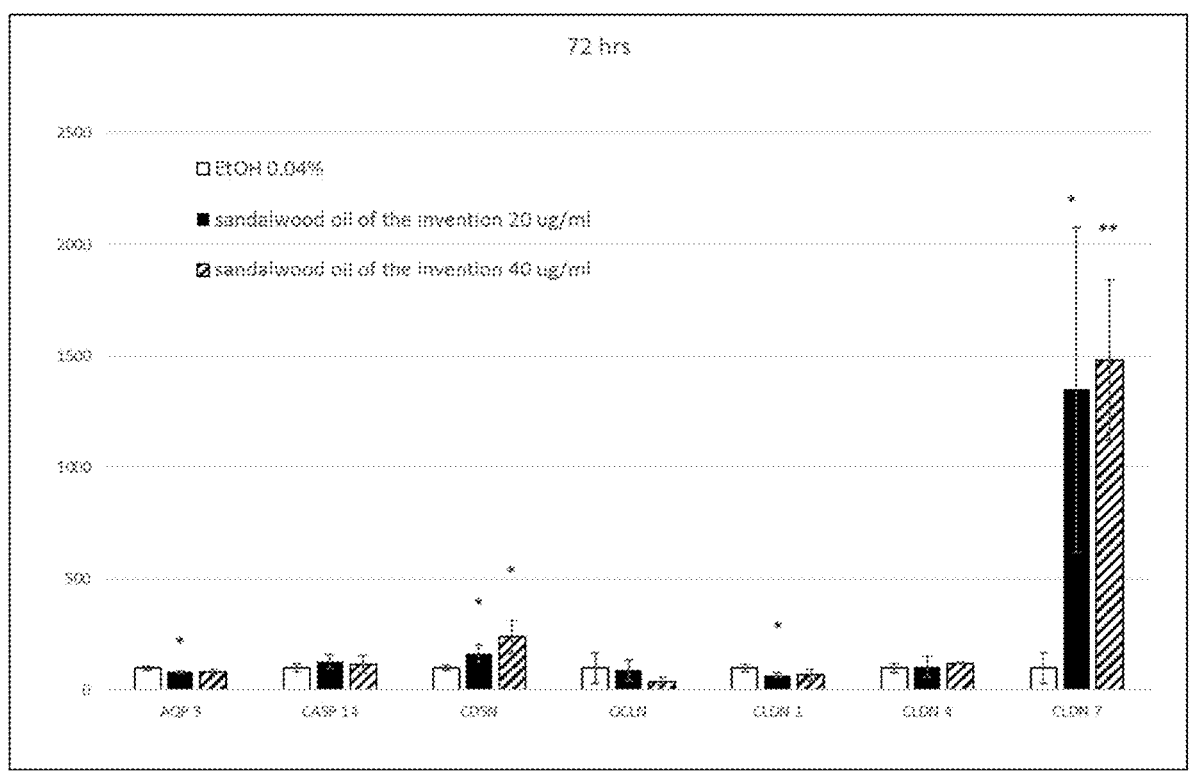

The data presented in FIG. 6 demonstrates a 33% and 50% reduction in the number of mosquito landings when the ingredient was tested at 0.4 mg/ml and 10 mg/ml, respectively.

Hence the sandalwood oil of the invention shows mosquito repellency.

Example 5: Effect of Sandalwood Oil of the Invention on Gene Expression and Protein Abundance in Normal Human Epidermal Keratinocytes Cells (NHEKs Methods
Cell Culture Conditions Normal Human foreskin-derived Epidermal Keratinocytes (NHEKs; Lonza, 00192906) were grown in Epilife medium (Fisher Scientific, M-EPI-500-A) supplemented with Human Keratinocyte Growth Supplement (HKGS; Fisher Scientific, S-001-5) and antibiotics (Gentamycin, Fisher Scientific, 15710-049).

Gene Expression Analysis

NHEKs were seeded into flasks (25 cm$^2$) and maintained in a humidified incubator at 37° C. with 5% $CO_2$ atmosphere. After 24 h, sandalwood oil of the invention was applied at 3 concentrations (10-20 and 40 μg/ml) for 24 h. Cells were rinsed with cold PBS and lysed in the ad hoc buffer. Total RNA was extracted using the Qiagen RNeasy kit (Qiagen, 74106), following the supplier's instructions. The collected RNAs were stored at −80° C. The RNA concentration was determined by spectrophotometric measurement (QIAxpert, Qiagen) and the RNA quality was analyzed by visualization of intact ribosomal RNA bands by capillarity electrophoresis (1.9 kb for the 18S-RNA and 4.7 kb for the 28S-RNA).

Modification of expression of 11 target genes in response to treatment was measured by TaqMan assays. Reverse transcription was performed with the high capacity RNA-to-cDNA kit (Applied Biosystems, 438706) from total RNA according to the manufacturer's instructions. The cDNAs were then stored at −20° C. until use in polymerase chain reactions (PCR).

PCRs were executed with the Quantstudio7 Real-Time PCR System (Applied Biosystems). In brief, 4 μl cDNA (4ng) were mixed with 10 μl of TaqMan Fast Advanced Master Mix (Applied Biosystems), 1 μl of TaqMan Gene Expression Assay and 5 μl of RNAse free water. The thermal cycles were programmed with one first denaturation step at 95° C. for 20s. The amplification protocol was followed with 40 cycles (is at 95° C. and 20s at 60° C.).

In order to normalize the results, a housekeeping gene (B2M; β-microglobulin) was amplified from the same cDNA samples. A control without cDNA was performed in parallel as negative control of amplification. This allowed to verify the absence of contaminants.

The relative expression levels were calculated by the comparative Ct (ΔΔCt) method (Pfaffl, M. W. A new mathematical model for relative quantification in real-time RT-PCR. *Nucleic Acids Res.* 29, e45 (2001); Livak, K. J. & Schmittgen, T. D. Analysis of relative gene expression data using real-time quantitative PCR and the 2(-Delta Delta C(T)) Method. *Methods San Diego Calif* 25, 402-408 (2001). All the measurements were performed from triplicates of culture (n=3). Values of $0.01 < p < 0.05$ are considered significant (*), $0.001 < p < 0.01$ are considered highly significant () and $p < 0.001$ are very highly significant (*) (Student's test).

Protein Immunostaining and Quantification on NHEKs Keratinocytes

NHEKs keratinocytes were seeded on 0.7 cm2 glass slides (Millipore, PEZGS0816) in complete medium, 24 h before the treatment. They were then treated for 0 h, 24 h or 72 h with sandalwood oil of the invention at 20 and 40 μg/ml. Culture triples (n=3) were made for each target analysis.

NHEKs were fixed and exposed to the primary antibody specific for the proteins of interest. Fluorescein-conjugated secondary antibodies were then used to detect the primary antibodies. DAPI or 4',6'-diamidino-2-phenylindole, a fluorescent molecule able of binding to the adenine and thymine bases of DNA, was used to detect the nuclei of the keratinocytes. The slides were mounted using Mowiol (Sigma, 32.459-0) or ProLong Diamond Antifade mountant (Thermo Fisher, P36962).

Table 5 below gives the references of the primary and secondary antibodies used for each protein target.

TABLE 5

| Antibodies | Type/source | Suppliers | References |
|---|---|---|---|
| AQP3 | Primary (Rabbit) | Abcam | Ab153694 |
| CDSN | | Thermo Fisher Scientific | PA5-97575 |
| OCLN | | Abcam | Ab31721 |
| CASP14 | | Abcam | Ab174847 |
| CLDN1 | | Thermo Fisher Scientific | 51-9000 |

TABLE 5-continued

| Antibodies | Type/source | Suppliers | References |
|---|---|---|---|
| CLDN4 | | Abcam | Ab53156 |
| CLDN7 | | Abcam | Ab207300 |
| ABCA12 | Primary (Goat) | Novus | NB100-93466 |
| CAMP | Primary (Mouse) | LS-Bio | LS-C136051 |
| Anti-Rabbit IgG Alexa Fluor 488 | Secondary (Goat) | Thermo Fisher Scientific | A11008 |

Results

To probe the in vitro potential of sandalwood oil of the invention to modulate genes and molecular pathways that are important for skin functions, the simultaneous analysis of the expression of a gene panel was performed on NHEKs cells by Taqman low density array (TLDA) after treatment with sandalwood oil of the invention at 10, 20 and 40 µg/ml for 24 h. This analysis focused on 96 genes which are known to play key role in epidermal benefit, such as epidermal biology, cornification, cell junctions, lipid synthesis, melanin synthesis, neurogenic inflammation, antimicrobial and anti-oxidant defenses, etc.

The effect of sandalwood oil of the invention on keratinocytes seemed to impact mainly genes involved in the cell mechanisms responsible for epidermal barrier function and water retention, skin defense against threats and epidermal cohesion.

The effect of sandalwood oil of the invention on a limited subset of such genes was therefore reconfirmed by RT-qPCR. Sandalwood oil of the invention significantly upregulated the expression of aquaporin 3 (AQP 3), caspase 14 (CASP 14), hyaluronan synthase 2 and 3 (HAS 2 and HAS 3), claudin 1, 4 and 7 (CLD 1, CLD 4 and CLD 7), occludin (OCL), corneodesmosin (CDS), ATP-binding cassette subfamily A member 12 (ABCA 12) and cathelicidin antimicrobial peptide LL-37 (CAMP). The effect of sandalwood oil of the invention was also dose-dependent.

Following on from the above observations, we wanted to see if the increased gene expression also translated into a higher abundance of the correspondent protein markers. NHEKs cells were treated with sandalwood oil of the invention at 20 and 40 µg/ml for 72 hours. Protein detection and quantification was undertaken for 9 proteins by immunostaining (AQP3, CASP14, CLDN1, CLDN4, CLDN7, OCLN, CDSN, ABCA12 and CAMP/LL37) at 3 time-points (0, 24 and 72 hours from the beginning of treatment). However, ABCA12 detection with the available antibody was problematic and CAMP could only be detected after stimulation with vitamin D3 in hypercalcic conditions (a condition known to stimulate keratinocyte differentiation). The effect of the compound on these targets could not therefore be studied.

In line with the observation on gene expression, we found the abundance of aquaporin, caspase, claudin 4, claudin 1, claudin 7 and occludin increased after 24 hr of exposure to sandalwood oil of the invention, the first 3 markers in a statistically significant way.

Corneodesmosin and claudin 7 were also increased in a statistically significant way after 72 hr of exposure to the ingredient.

This demonstrates that the up-regulation detected at mRNA level translate into an increased protein abundance for the same markers, thereby indicating a functional effect of sandalwood oil of the invention.

The data generated in the experiments discussed above are show in Tables 6 and 7 and FIGS. 7A-7D and 8

TABLE 6

Effect of sandalwood oil of the invention on mRNA levels (gene expression)

| | | AQP3 | | | CASP14 | | | HAS2 | | | HAS3 | | | CLDN1 | | |
|---|---|---|---|---|---|---|---|---|---|---|---|---|---|---|---|---|
| | | mean | stdev | p-value* | mean | stdev | p-value* | mean | stdev | p-value* | mean | stdev | p-value* | mean | stdev | p-value* |
| | CTL EtOH 0.04% | 100 | 5 | — | 100 | 3 | — | 100 | 1 | — | 100 | 6 | — | 100 | 4 | — |
| sandalwood oil of the invention | 10 µg/ml | 206 | 16 | 0.0004 | 301 | 94 | 0.020 | 89 | 12 | 0.188 | 168 | 7 | 0.0002 | 126 | 5 | 0.005 |
| | 20 µg/ml | 225 | 23 | 0.0008 | 659 | 86 | 0.0004 | 133 | 18 | 0.034 | 265 | 52 | 0.0054 | 287 | 7 | 0.0009 |
| | 40 µg/ml | 379 | 48 | 0.0006 | 952 | 164 | 0.0008 | 248 | 17 | 0.0001 | 192 | 39 | 0.0156 | 1155 | 0 | 0.0001 |

| | | cell-cell junctions CLDN4 | | | cell-cell junctions CLDN7 | | | cell-cell junctions OCLN | | |
|---|---|---|---|---|---|---|---|---|---|---|
| | | mean | stdev | p-value* | mean | stdev | p-value* | mean | stdev | p-value* |
| | CTL EtOH 0.04% | 100 | 7 | — | 101 | 13 | — | 100 | 9 | — |
| sandalwood oil of the invention | 10 µg/ml | 266 | 32 | 0.0009 | 189 | 2 | 0.0003 | 212 | 15 | 0.0004 |
| | 20 µg/ml | 680 | 75 | 0.0002 | 509 | 62 | 0.0004 | 509 | 50 | 0.0002 |
| | 40 µg/ml | 7335 | 1666 | 0.0017 | 2663 | 449 | 0.0006 | 3586 | 149 | 0.000002 |

TABLE 6-continued

Effect of sandalwood oil of the invention on mRNA levels (gene expression)

|  |  | Cell-cell junctions/ Desquamation CDSN | | | Lipids synthesis & transport ABCA12 | | | antimicrobial defense CAMP (LL-37) | | |
| --- | --- | --- | --- | --- | --- | --- | --- | --- | --- | --- |
|  |  | mean | stdev | p-value* | mean | stdev | p-value* | mean | stdev | p-value* |
|  | CTL EtOH 0.04% | 100 | 8 | — | 100 | 63 | — | 100 | 1 | — |
| sandalwood oil of the invention | 10 µg/ml | 138 | 21 | 0.0440 | 282 | 217 | 0.191 | 591 | 85 | 0.0006 |
|  | 20 µg/ml | 237 | 57 | 0.0146 | 665 | 141 | 0.0020 | 801 | 43 | 0.0000 |
|  | 40 µg/ml | 570 | 73 | 0.0004 | 3317 | 688 | 0.0008 | 797 | 213 | 0.0048 |

*versus CTL EtOH

TABLE 7

Effect of sandalwood oil of the invention on protein abundance

|  |  | AQP 3 | CASP 14 | CDSN | OCLN | CLDN 1 | CLDN 4 | CLDN 7 |
| --- | --- | --- | --- | --- | --- | --- | --- | --- |
| 24 hr EtOH 0.04% | mean | 100 | 100 | 100 | 100 | 100 | 100 | 100 |
|  | st dev | 8 | 30 | 39 | 25 | 78 | 84 | 22 |
| sandalwood oil of the invention 20 ug/ml | mean | 148 | 160 | 96 | 181 | 299 | 728 | 114 |
|  | st dev | 31 | 16 | 8 | 149 | 160 | 130 | 8 |
|  | p-value$^S$ | 0.0589 | 0.0383* | 0.855 | 0.4084 | 0.1247 | 0.0022** | 0.35 |
| sandalwood oil of the invention 40 ug/ml | mean | 184 | 131 | 120 | 379 | 513 | 712 | 193 |
|  | st dev | 41 | 30 | 14 | 438 | 363 | 326 | 86 |
|  | p-value$^S$ | 0.0249* | 0.2749 | 0.4544 | 0.388 | 0.1263 | 0.0346* | 0.14 |
| 72 hr EtOH 0.04% | mean | 100 | 100 | 100 | 100 | 100 | 100 | 100 |
|  | st dev | 11 | 20 | 12 | 71 | 17 | 22 | 70 |
| sandalwood oil of the invention 20 ug/ml | mean | 81 | 129 | 167 | 91 | 66 | 104 | 1348 |
|  | st dev | 5 | 32 | 37 | 48 | 10 | 48 | 731 |
|  | p-value$^S$ | 0.0493* | 0.2548 | 0.0392* | 0.8701 | 0.0416* | 0.9106 | 0.042* |
| sandalwood oil of the invention 40 ug/ml | mean | 81 | 118 | 240 | 39 | 69 | 123 | 1480 |
|  | st dev | 12 | 40 | 75 | 19 | 26 | 1 | 360 |
|  | p-value$^S$ | 0.0993 | 0.5192 | 0.0336* | 0.2242 | 0.1671 | 0.1421 | 0.0029** |

$^S$versus EtOH 0.04%

Values of $0.01 < p < 0.05$ are considered significant (*), $0.001 < p < 0.01$ are considered highly significant () and $p < 0.001$ are very highly significant (*) (Student's test).

Example 6: Effect of Sandalwood Oil of the Invention on the Permeability of Reconstructed Human Epidermis (RHE Methods Human epidermis was reconstituted in vitro with NHEKs keratinocytes (RHE, StratiCELL, batches: AW0320/4 and AW0520/7). The tissues were cultured at the air-liquid interface on polycarbonate filters in Epilife medium (Fisher Scientific, M-EPI-500-A) containing supplements and antibiotics (Gentamycin, Fisher Scientific, 15710-049). They were maintained in a humid atmosphere at 37° C. with 5% $C_{02}$. After 14 days, the RHE were multi-layered and fully differentiated, as verified by histology. After RHE reconstruction, the test compounds were applied for 48 h (from day 14 to day 16) in the culture medium. RHE tissues were treated with sandalwood oil of the invention at 20 µg/ml and 40 µg/ml. In parallel, a reference condition (SDS at 0.005%) was applied to alter RHE barrier function and validate the methodology. At the end of treatment (n=6), RHE were rinsed twice in a solution of PBS/CaCl$_2$. Then, the cell membrane-impermeable marker molecule EZ-link Sulfo-NHS-LC-Biotin (Thermo Fisher Scientific, 21335) was applied at 2 mg/ml in PBS to the basal side of the RHE. After 30 min of incubation at 37° C., tissues were rinsed twice in a solution of PBS/CaCl$_2$/Glycine, before being fixed in 4% formaldehyde, dehydrated and embedded in paraffin. Sections of 6 µm thickness were generated using a Leica microtome RM2245 and laid over microscopic slides. One section of each sample was dewaxed and rehydrated. The slides were then incubated in the presence of a streptavidin conjugated to Alexa Fluor® 488 (Thermo Fisher Scientific, S32354) that allowed the detection of the biotin which has diffused into the epidermal layers. The slides were then mounted using a specific mounting solution (SlowFade Diamond Antifade Mountant with DAPI; Thermo Fisher Scientific, S36964). This solution contains DAPI, a fluorescent molecule capable of binding to the adenine and thymine bases of DNA, and therefore to highlight the nuclei of epidermal keratinocytes.

The slides were stored at 4° C. and in the dark until images were captured per replicate, using a Leica microscope (DM 2000, lens 40x) combined to a Leica camera (DFC420C). Image quantification was performed using the QWin 3 analysis software (Leica). Each treatment was applied to 6 RHE and 9 images were taken and quantified for each RHE, giving a total of 54 measures per condition. RHE treated with sandalwood oil of the invention at 20 µg/ml and 40 µg/ml were compared to RHE treated with solvent (ethanol 0.04%). Intact skin barrier function will slow down biotin diffusion, whereas impaired barrier function will allow the diffusion of the dye. Values of $0.01 < p < 0.05$ are considered significant (*), $0.001 < p < 0.01$ are considered highly significant () and $p < 0.001$ are very highly significant (*) (Student's test).

Results

The reference treatment, SDS, reduced the barrier function of epidermis as compared to untreated control, thereby increasing dye diffusion through the cell layers. This validated the method of analysis.

The treatment with sandalwood oil of the invention at 20 µg/ml did not have a significant effect as compared to the control condition (ethanol 0.04%). However, at the concentration of 40 µg/ml, sandalwood oil of the invention significantly reinforced the barrier property of RHE, given that the biotin diffusion was decreased by 30%, as compared to ethanol 0.04% (control condition). This difference was statistically significant (p=0.015)

Figure 9A:
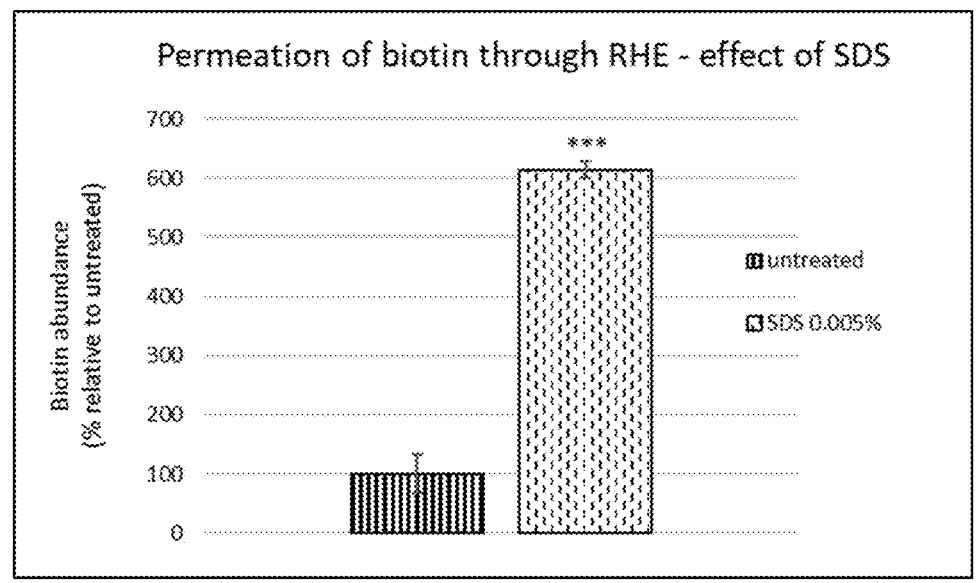
FIG. 9: Effect of sandalwood oil of the invention at 20 and 40 µg/ml on biotin diffusion in Reconstituted Human Epidermis
Figure 9B:
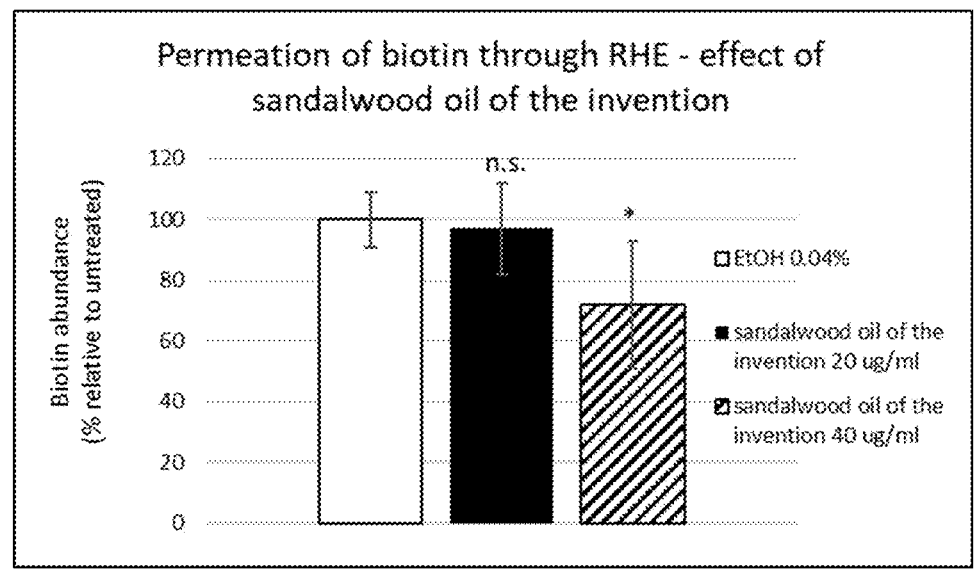

The data generated in the experiments discussed in this example are show in Table 8 and FIG. 9

TABLE 8

| | Surface stained*mean intensity/surface area | biotin abundance (% relative to untreated) | ST dev | p-value | Comment |
|---|---|---|---|---|---|
| untreated | 17 | 100 | 32 | — | |
| SDS 0.005% | 103 | 614 | 14 | 6.80E−12*** | versus untreated |
| EtOH 0.04% | 27 | 100 | 9 | 0.002** | versus untreated |
| sandalwood oil of the invention 20 ug/ml | 26 | 97 | 15 | 0.69 | versus EtOH 0.04% |
| sandalwood oil of the invention 40 ug/ml | 20 | 72 | 21 | 0.015* | versus EtOH 0.04% |

$0.01 < p < 0.05$ are considered significant (*), $0.001 < p < 0.01$ are considered highly significant () and $p < 0.001$ are very highly significant (*)

Example 7: Effects of Sandalwood Oil of the Invention on Gene and Protein Expression in a Model of Reconstructed Human Epidermis (RHE) Mimicking Sensitive Skin Methods
Reconstitution of Human Epidermis Human epidermis was reconstituted in vitro as described previously. After full tissue differentiation (day 16), the RHE tissues were treated with three interleukins (IL-4; 50 ng/ml, IL-13; 50 ng/ml and IL-25; 20 ng/ml) for 48 hours in order to induce changes typical of a sensitive skin phenotype (De Vuyst, et al., 2016). Sandalwood oil of the invention was diluted at 20 µg/ml and 40 µg/ml in culture medium and added together with the cytokine cocktail during the same 48 h. The reference compound GW3965 (10 µM), a synthetic nonsteroidal liver X receptor (LXR) agonist was applied in the culture medium for 48 h as well.

Gene Expression Analysis

Total RNA was extracted using the Qiagen RNeasy kit (Qiagen, 74106). Cells were rinsed with cold PBS and lysed in the ad hoc buffer provided in the kit. Extraction was performed according to the supplier's recommendations. The collected RNAs were stored at −80° C. The RNA concentration was determined by spectrophotometric measurement (QIAxpert, Qiagen) and the RNA quality was analyzed by visualization of intact ribosomal RNA bands by capillarity electrophoresis (1.9 kb for the 18S-RNA and 4.7 kb for the 28S-RNA). Reverse transcription was performed with the high capacity RNA-to-cDNA kit (Applied Biosystems, 438706) from total RNA according to the manufacturer's instructions. The cDNAs were then stored at −20° C. until use in polymerase chain reactions.

The TaqMan low density arrays were designed by the service provider (StratiCELL) and manufactured on demand by Applied Biosystems. Three reference genes (house-keeping) and 93 genes of interest were studied. The TaqMan arrays were processed as described by the manufacturer's instructions (Micro Fluidic Card Getting Started Guide, Applied Biosystems). Briefly, cDNAs were mixed with a specific buffer (TaqMan Fast Advanced Master Mix, 4444557, Applied Biosystems) before being injected into the arrays and dispersed into the wells by centrifugation. Arrays were sealed and qPCRs were run using the Quantstudio7 Real-Time PCR System (Applied Biosystems) and its software (QuantStudio real time PCR Software v0.3. software, Applied Biosystems). Threshold cycles (Ct) were obtained for each gene. Results files were exported from the qPCR device and analyzed using the DataAssist Software (v3.01, Applied Biosystems) designed to perform relative quantification of gene expression using the comparative Ct (ΔΔCt) method (Pfaffl, M. W. A new mathematical model for relative quantification in real-time RT-PCR. *Nucleic Acids Res.* 29, e45 (2001); Livak, K. J. & Schmittgen, T. D. Analysis of relative gene expression data using real-time quantitative PCR and the 2(-Delta Delta C(T)) Method. *Methods San Diego Calif* 25, 402-408 (2001). The Ct values were normalized to the Ct of a housekeeping gene (B2M) present on the array. The maximum Ct cut-off value was fixed at 36 cycles. All the measurements were performed from triplicates (n=3).

Protein Expression Analysis

Protein levels of loricrin, involucrin and HAS3 were quantified at the end of the treatments by immuno-fluorescence. One section of each sample was dewaxed and rehydrated and the slides were incubated in the presence of the primary antibody specific for each of the 3 target proteins. Fluorescein-conjugated secondary antibodies were then used to detect the primary antibodies. DAPI Slowfade Diamond was used to detect the nuclei of the cells. The antibodies used are listed in Table 9 below

TABLE 9

| Antibodies | Type/source | Suppliers | References |
|---|---|---|---|
| Anti-LOR | Primary/Rabbit | Abcam | ab85679 |
| Anti-INV | Primary/Rabbit | Abcam | ab53112 |
| Anti-HAS3 | Primary/Rabbit | LsBio | LS-B10150-200 |
| Anti-Rabbit IgG Alexa Fluor 488 | Secondary/Goat | Thermo Fisher Scientific | A11008 |

Results

We wanted to evaluate the potential of the sandalwood oil of the invention to protect and/or restore a RHE, which had been challenged with interleukins in order to induce modifications mimicking sensitive skin. This model was described in the research paper by Hubaux, R., et al. *Exp. Dermatol.* 27, 1403-1407 (2018) and allows to reproduce in vitro the disruptions found in sensitive skin with atopic tendency. Such disruptions include skin barrier alteration and the modification of a panel of genes related to skin barrier, itching, inflammation and lipids homeostasis. At the end of the culture process and treatments, RNA samples were prepared from treated and control RHE. The protective effect of the treatment with sandalwood oil of the invention was studied through the analysis of gene regulation for 93 epidermal markers which were previously shown to be altered in a context of sensitive and/or atopic skin.

Treatment with sandalwood oil of the invention at both 20 and 40 μg/ml induced significant changes in the expression of several genes compared to the solvent alone (ethanol 0.04%), which are summarized in the table below. For clarity, quantification of gene expression is expressed in a relative fashion (RQ=relative quantification), either versus untreated RHE, or versus RHE challenged with the cytokine mix, or versus RHE challenged with the cytokine mix and the solvent. Downregulation of gene expression is represented by values <1, whereas overexpression is indicated by values >1. Statistical analysis was performed with a specialized software (DataAssist) and statistical significance is highlighted in light grey.

As compared to untreated controls, the treatment with cytokines altered gene expression—mostly by downregulation of key genes implicated in lipid homeostasis, inflammation, skin barrier function and itch/pruritus. The gene coding for periostin was instead upregulated (POSTN). The treatment with sandalwood oil of the invention at 20 and 40 μg/ml showed a tendency to re-equilibrate these unbalances (i.e. increasing the expression of down-regulated genes and decreasing the expression of up-regulated genes) towards a situation similar to that of the untreated controls.

Similarly to what done for the modulation of gene expression, we also studied the potential rebalancing effect of sandalwood oil of the invention on 3 specific protein targets using immunostaining. The levels of involucrin (IVL), loricrin (LOR) and hyaluronan synthase 3 (HAS3) were quantified and compared to untreated RHE, or versus RHE challenged with the cytokine mix, or versus RHE challenged with the cytokine mix and the solvent. GW3965 is a an LXR receptor agonist, which is known to reverse the effect of cytokine stimulation on involucrin and hyaluronan synthase 3. This molecule was therefore used as positive control for the experiment. As precursors of the cornified envelope, it is well accepted that involucrin and loricrin play a critical role for the barrier function of the skin. During the development of the epidermis, cornified envelope precursors become covalently cross-linked to form a mature envelope adjacent to the cell membrane. The integrity of the corneocytes depends on this outer cornified envelope and is essential for maintenance of the barrier function.

Hyaluronan synthase 3 (Has 3) is the major producer of hyaluronan in the epidermis and is known to be upregulated in atopic skin. Hyaluronan is present in the extracellular space between the stratified keratinocytes of epidermis and is involved in the proliferation, differentiation, and migration of keratinocytes, as well as in the establishment of the epidermal barrier.

Abundance of both loricrin and involucrin was diminished in RHE challenged with the mixture of cytokines that were used to induce a response similar to that of sensitive skin. Sandalwood oil of the invention increased both proteins to a level that was statistically superior as compared to challenged RHE, in the presence of solvent. Hyaluronan synthase 3, as expected, was increased in RHE challenged with the mixture of cytokines that were used to induce a response similar to that of sensitive skin. Sandalwood oil of the invention decreased the abundance of this protein down to levels comparable to those of the untreated controls and, when tested at 40 μg/ml, down at a level that was statistically relevant as compared to that of challenged RHE, in the presence of solvent.

Sensitive skin is characterized by alterations of the skin barrier and lipids homeostasis, itching, and inflammation. Sandalwood of the invention can be useful to alleviate sensitive skin condition since it was shown here to rebalance the expression of genes and proteins that are altered in a RHE sensitive skin model, especially addressing the compromised skin barrier function.

Figure 10:
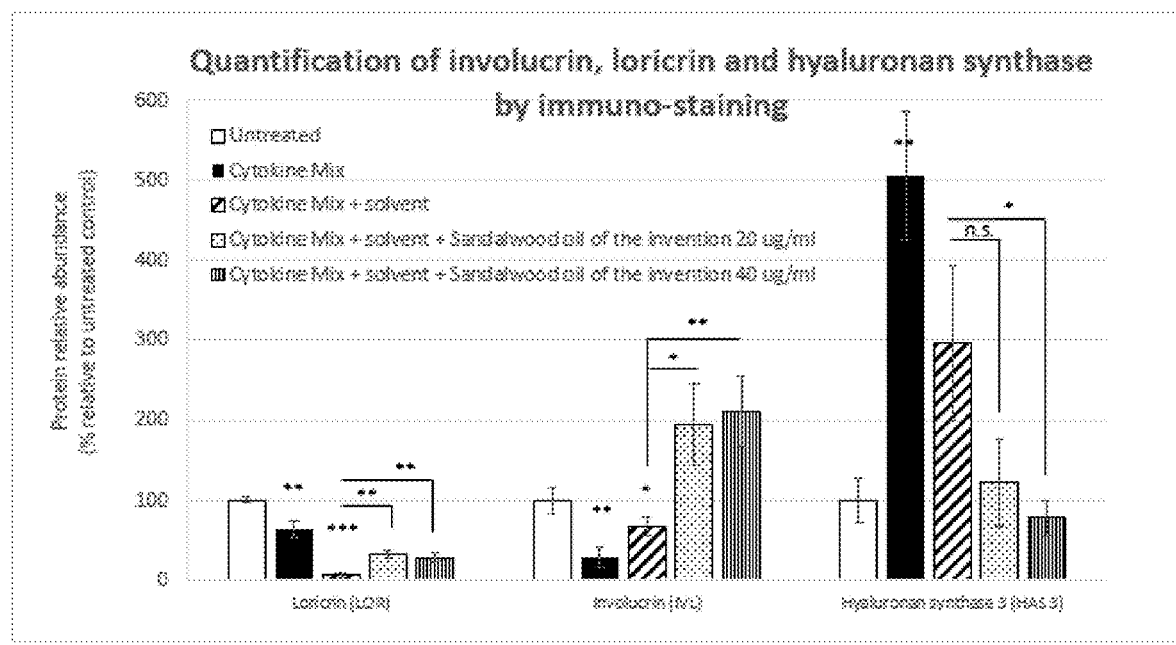
FIG. 10: Effect of sandalwood oil of the invention at 20 and 40 µg/ml on the expression levels of loricrin, involucrin and hyaluronan synthase 3 in a reconstituted human epidermis model mimicking sensitive skin

The data generated in the experiments discussed in this example are show in Tables 10 and 11 and FIG. 10

TABLE 10

| Function | Gene Name | Cytokine Mix | | Cytokine Mix + solvent | | Cytokine Mix + solvent + Sandalwood oil of the invention 20 μg/ml | |
| --- | --- | --- | --- | --- | --- | --- | --- |
| | | RQ | p-value | RQ | p-value | RQ | p-value |
| Lipids homeostasis | ABCA1 | 0.4625 | 0.0286* | 0.5384 | 0.0561 | 0.5419 | 0.0389* |
| | | 1 | — | 1.164108108 | 0.2302 | 1.17167568 | 0.3514 |
| | | | | 1 | — | 1.00650074 | 0.9578 |
| Lipids homeostasis | ABCG1 | 0.7101 | 0.3489 | 0.7503 | 0.3861 | 0.9296 | 0.8053 |
| | | 1 | — | 1.056611745 | 0.8191 | 1.30911139 | 0.3269 |
| | | | | 1 | — | 1.23897108 | 0.3287 |
| Lipids homeostasis | FASN | 0.5223 | 0.0721 | 0.6268 | 0.1312 | 0.7866 | 0.2706 |
| | | 1 | — | 1.200076584 | 0.526 | 1.50603102 | 0.0011** |
| | | | | 1 | — | 1.25494576 | 0.3617 |
| Lipids homeostasis | HMGCS1 | 0.5445 | 0.3335 | 0.4954 | 0.2952 | 0.6692 | 0.4572 |
| | | 1 | — | 0.909825528 | 0.7371 | 1.22901745 | 0.2514 |
| | | | | 1 | — | 1.35082761 | 0.2687 |
| Lipids homeostasis | LPIN1 | 0.7245 | 0.1007 | 0.8365 | 0.5284 | 1.2501 | 0.3333 |
| | | 1 | — | 1.154589372 | 0.6488 | 1.72546584 | 0.0958 |
| | | | | 1 | — | 1.49444112 | 0.2148 |

TABLE 10-continued

| Function | Gene Name | | | | | |
|---|---|---|---|---|---|---|
| Inflammation | CCL20 | 0.5403 | 0.1801 | 0.592 | 0.211 | 0.8165 | 0.6896 |
| | | 1 | — | 1.095687581 | 0.4932 | 1.51119748 | 0.5179 |
| | | | | 1 | — | 1.37922297 | 0.593 |
| Barrier recovery | SPRR1A | 0.4271 | 0.2224 | 0.5092 | 0.2721 | 0.5991 | 0.3479 |
| | | 1 | — | 1.192226645 | 0.5319 | 1.40271599 | 0.0556 |
| | | | | 1 | — | 1.17655145 | 0.4923 |
| Barrier recovery | IVL | 0.518 | 0.1368 | 0.623 | 0.2081 | 0.6319 | 0.221 |
| | | 1 | — | 1.202702703 | 0.4496 | 1.21988417 | 0.2268 |
| | | | | 1 | — | 1.01428571 | 0.9383 |
| Hypersensitivity, itch, pruritus | F2RL1 | 0.7274 | 0.1053 | 0.6158 | 0.0536 | 0.6504 | 0.1013 |
| | | 1 | — | 0.846576849 | 0.3683 | 0.89414352 | 0.615 |
| | | | | 1 | — | 1.05618707 | 0.8348 |
| Hypersensitivity, itch, pruritus | NGFR | 0.3297 | 0.1783 | 0.7163 | 0.6195 | 0.7817 | 0.6112 |
| | | 1 | — | 2.172581134 | 0.4428 | 2.37094328 | 0.1389 |
| | | | | 1 | — | 1.09130253 | 0.8944 |
| Hypersensitivity, itch, pruritus | POSTN | 19.0811 | 0.001 | 22.0152 | 0.0036 | 16.5305 | 0.0158* |
| | | 1 | — | 1.153769961 | 0.2114 | 0.86632846 | 0.3697 |
| | | | | 1 | — | 0.75086758 | 0.0992 |
| Hypersensitivity, itch, pruritus | TSLP | 0.2811 | 0.1368 | 0.2656 | 0.1334 | 0.348 | 0.1554 |
| | | 1 | — | 0.944859481 | 0.7329 | 1.2379936 | 0.4767 |
| | | | | 1 | — | 1.31024096 | 0.3817 |

| | | Cytokine Mix + solvent + Sandalwood oil of the invention 40 µg/ml | | |
|---|---|---|---|---|
| Function | Gene Name | RQ | p-value | Comparison |
| Lipids homeostasis | ABCA1 | 1.3964 | 0.1034 | vs untreated |
| | | 3.019243243 | 0.0158* | vs Cytokine Mix |
| | | 2.593610698 | 0.0272* | vs Cytokine Mix + solvent |
| Lipids homeostasis | ABCG1 | 1.0804 | 0.7996 | vs untreated |
| | | 1.521475848 | 0.1991 | vs Cytokine Mix |
| | | 1.43995735 | 0.2206 | vs Cytokine Mix + solvent |
| Lipids homeostasis | FASN | 0.8278 | 0.3674 | vs untreated |
| | | 1.584912885 | 0.0517 | vs Cytokine Mix |
| | | 1.320676452 | 0.2894 | vs Cytokine Mix + solvent |
| Lipids homeostasis | HMGCS1 | 1.0799 | 0.8734 | vs untreated |
| | | 1.98328742 | 0.2111 | vs Cytokine Mix |
| | | 2.179854663 | 0.1811 | vs Cytokine Mix + solvent |
| Lipids homeostasis | LPIN1 | 1.2784 | 0.105 | vs untreated |
| | | 1.76452726 | 0.0045** | vs Cytokine Mix |
| | | 1.528272564 | 0.1521 | vs Cytokine Mix + solvent |
| Inflammation | CCL20 | 0.7173 | 0.3595 | vs untreated |
| | | 1.32759578 | 0.3189 | vs Cytokine Mix |
| | | 1.211655405 | 0.4629 | vs Cytokine Mix + solvent |
| Barrier recovery | SPRR1A | 0.7513 | 0.5496 | vs untreated |
| | | 1.759072817 | 0.1815 | vs Cytokine Mix |
| | | 1.475451689 | 0.2955 | vs Cytokine Mix + solvent |
| Barrier recovery | IVL | 0.878 | 0.6712 | vs untreated |
| | | 1.694980695 | 0.1425 | vs Cytokine Mix |
| | | 1.409309791 | 0.266 | vs Cytokine Mix + solvent |
| Hypersensitivity, itch, pruritus | F2RL1 | 0.9082 | 0.5604 | vs untreated |
| | | 1.248556503 | 0.2 | vs Cytokine Mix |
| | | 1.47482949 | 0.0954 | vs Cytokine Mix + solvent |
| Hypersensitivity, itch, pruritus | NGFR | 0.9318 | 0.8677 | vs untreated |
| | | 2.826205641 | 0.0552 | vs Cytokine Mix |
| | | 1.300851598 | 0.6621 | vs Cytokine Mix + solvent |
| Hypersensitivity, itch, pruritus | POSTN | 17.6447 | 0.0004*** | vs untreated |
| | | 0.924721321 | 0.4244 | vs Cytokine Mix |
| | | 0.80147807 | 0.0713 | vs Cytokine Mix + solvent |
| Hypersensitivity, itch, pruritus | TSLP | 0.4748 | 0.2158 | vs untreated |
| | | 1.68907862 | 0.2834 | vs Cytokine Mix |
| | | 1.787650602 | 0.258 | vs Cytokine Mix + solvent |

*$0.01 < P < 0.05$;
**$0.001 < P < 0.01$ and
***$P < 0.001$.

TABLE 11

| | | Untreated | | | Cytokine Mix | | | Cytokine Mix + solvent | | |
|---|---|---|---|---|---|---|---|---|---|---|
| | | | | | | | p-value | | | p-value |
| Function | Protein | RQ | ST Dev | p-value | RQ | ST Dev | (vs untreated) | RQ | ST Dev | (vs untreated) |
| Skin Barrier | Loricrin (LOR) | 100 | 3.1 | — | 63 | 10 | 0.0036** | 6 | 3.1 | 0.000003*** |
| Skin Barrier | Involucrin (IVL) | 100 | 16.5 | — | 29 | 12.6 | 0.0039** | 67 | 11.8 | 0.047* |
| Skin barrier, keratinocyte differentiation | Hyaluronan synthase 3 (HAS 3) | 100 | 27.2 | — | 506 | 79.6 | 0.0011** | 297 | 97.3 | 0.027* |

| | | Cytokine Mix + solvent + Sandalwood oil of the invention 20 µg/ml | | | Cytokine Mix + solvent + Sandalwood oil of the invention 40 µg/ml | | |
|---|---|---|---|---|---|---|---|
| | | | | p-value (vs cytokine mix + solvent) | | | p-value (vs cytokine mix + solvent) |
| Function | Protein | RQ | ST Dev | | RQ | ST Dev | |
| Skin Barrier | Loricrin (LOR) | 33 | 5.2 | 0.002** | 29 | 4.7 | 0.002** |
| Skin Barrier | Involucrin (IVL) | 195 | 50.3 | 0.012* | 211 | 43.4 | 0.005** |
| Skin barrier, keratinocyte differentiation | Hyaluronan synthase 3 (HAS 3) | 122 | 54.2 | 0.052 | 78 | 22.2 | 0.018* |

RQ = Relative Quantification (with respect to untreated samples)
Values of $0.01 < p < 0.05$ are considered significant (*), $0.001 < p < 0.01$ are considered highly significant () and $p < 0.001$ are very highly significant (*) (Student's test).

TABLE 12

| | Untreated | | | Cytokine Mix | | | Cytokine Mix + solvent | | | Cytokine Mix + solvent + GW3965 10 uM | | |
|---|---|---|---|---|---|---|---|---|---|---|---|---|
| | | | | | | p-value | | | p-value | | | p-value |
| Protein | RQ | ST Dev | p-value | RQ | ST Dev | (vs untreated) | RQ | ST Dev | (vs untreated) | RQ | ST Dev | (vs cytokine mix + solvent) |
| Involucrin (IVL) | 100 | 16.5 | — | 29 | 12.6 | 0.0039 | 47 | 5.9 | 0.006 | 160 | 5.6 | 0.0000177 |
| Hyaluronan synthase 3 (HAS 3) | 100 | 27.2 | — | 506 | 79.6 | 0.0011 | 314 | 67 | 0.0068 | 106 | 32.8 | 0.0084 |

```
Sequence listing.
Codon optimized cDNA encoding for a SaCP816 N-terminal variant
SEQ ID NO: 1:
ATGGCACTGTTGTTGGCGGTTTTCTGGAGCGCTTTGATTATTCTGGTTAGCATCTTATTGCGTCGTCGTCAAAAACG

CAACAATTTGCCACCGGGCCCACCGGCCCTGCCGATCATCGGTAACATTCACATTCTGGGCACCCTGCCGCACCAGA

GCCTGTACAATCTGGCGAAGAAGTACGGTCCGATCATGTCCATGCGTTTGGGCTTGGTTCCGGCGGTGGTCATCAGC

AGCCCGGAAGCGGCCGAGCTGGTCCTGAAAACCCACGACATCGTTTTTGCTTCTCGCCCTCGTCTGCAAGTTGCAGA

TTACTTTCACTATGGCACCAAAGGCGTGATTCTGACCGAATATGGTACCTACTGGCGTAACATGCGTCGCCTGTGCA

CGGTCAAACTGCTGAACACCGTTAAGATTGATAGCTTTGCAGGCACCCGCAAGAAAGAAGTCGCTAGCTTCGTTCAG

AGCCTGAAAGAAGCAAGCGTGGCGCACAAAATGGTTAACCTGTCCGCACGCGTCGCTAATGTTATTGAGAATATGGT

TTGTCTGATGGTTATTGGTAGATCGTCTGACGAGCGTTTCAAGCTGAAAGAAGTGATCCAAGAAGCGGCACAGCTGG

CGGGTGCCTTCAATATTGGTGACTATGTCCCGTTTCTGATGCCGCTGGATCTGCAGGGCCTGACTCGCCGTATCAAG

AGCGGTAGCAAGGCATTCGATGACATCCTCGAGGTCATTATCGACGAGCATGTGCAAGACATTAAAGATCATGACGA

TGAGCAGCATGGTGACTTCATCGACGTGCTGCTGGCGATGATGAATAAGCCGATGGATTCTCGTGAGGGTCTGTCCA

TCATTGATCGCACGAACATTAAAGCGATCCTGGTGGATATGATCGGTGCCGCGATGGACACGAGCACCAGCGGTGTG
```

-continued
```
GAGTGGGCGATTTCGGAGCTGATTAAGCATCCTCGTGTCATGAAGAAACTGCAAGACGAAGTGAAAACCGTAATCGG

TATGAACCGCATGGTGGAAGAAGCGGATCTGCCGAAACTGCCGTACCTGGACATGGTTGTCAAGGAAACGATGCGTC

TGCATCCGCCAGGCCCGCTGCTGGTGCCGCGTGAAAGCATGGAAGATATTACGATCAACGGTTACTATATCCCGAAG

AAATCCCGCATTATTGTGAATGCATGGGCGATCGGCCGTGACACCAACGCCTGGAGCAATAATGCGCACGAGTTTTT

CCCTGAGCGTTTTATGAGCTCTAACGTTGATCTGCAAGGCCAGGACTTCCAGCTGATCCCGTTCGGTAGCGGTCGTC

GCGGTTGTCCGGGCATGCGTCTGGGTCTGACGACGGTCCGCTTGGTGCTGGCCCAACTGATTCACTGCTTCGACCTG

GAGCTTCCGAAGGGCACCGTCGCGACTGACCTGGATATGAGCGAGAAGTTTGGTCTGGCAATGCCGCGTGCGCAGCA

CTTACTGGCCTTTCCGACCTACCGTCTGGAGAGCTAA
```

SaCP816 N-terminal variant, amino acid sequence
SEQ ID NO: 2:
```
MALLLAVFWSALIILVSILLRRRQKRNNLPPGPPALPIIGNIHILGTLPHQSLYNLAKKYGPIMSMRLGLVPAVVIS

SPEAAELVLKTHDIVFASRPRLQVADYFHYGTKGVILTEYGTYWRNMRRLCTVKLLNTVKIDSFAGTRKKEVASFVQ

SLKEASVAHKMVNLSARVANVIENMVCLMVIGRSSDERFKLKEVIQEAAQLAGAFNIGDYVPFLMPLDLQGLTRRIK

SGSKAFDDILEVIIDEHVQDIKDHDDEQHGDFIDVLLAMMNKPMDSREGLSIIDRTNIKAILVDMIGAAMDTSTSGV

EWAISELIKHPRVMKKLQDEVKTVIGMNRMVEEADLPKLPYLDMVVKETMRLHPPGPLLVPRESMEDITINGYYIPK

KSRIIVNAWAIGRDTNAWSNNAHEFFPERFMSSNVDLQGQDFQLIPFGSGRRGCPGMRLGLTTVRLVLAQLIHCFDL

ELPKGTVATDLDMSEKFGLAMPRAQHLLAFPTYRLES
```

Codon optimized cDNA encoding for CPRm
SEQ ID NO: 3:
```
ATGGAACCTAGCTCTCAGAAACTGTCTCCGTTGGAATTTGTTGCTGCTATCCTGAAGGGCGACTACAGCAGCGGTCA

GGTTGAAGGTGGTCCACCGCCAGGTCTGGCAGCTATGTTGATGGAAAATAAGGATTTGGTGATGGTTCTGACGACGT

CCGTGGCAGTCCTGATCGGCTGTGTCGTGGTCCTGGCATGGCGTCGTGCGGCAGGTAGCGGTAAGTACAAGCAACCT

GAACTGCCTAAACTGGTGGTCCCGAAAGCAGCCGAACCGGAGGAGGCAGAGGATGATAAAACCAAGATCAGCGTGTT

TTTCGGCACCCAAACCGGTACGGCAGAAGGTTTCGCGAAGGCTTTTGTTGAAGAGGCCAAGGCGCGTTATCAGCAGG

CCCGTTTCAAAGTTATCGACCTGGACGACTATGCGGCAGACGATGACGAGTACGAAGAGAAACTGAAGAAGGAAAAC

TTGGCATTCTTCTTCTTGGCGTCCTACGGTGACGGCGAGCCGACGGACAACGCGGCACGCTTTTACAAATGGTTTAC

GGAGGGTAAGGACCGTGGTGAATGGCTGAACAATCTGCAGTACGGCGTTTTTGGTCTGGGTAACCGTCAATATGAGC

ATTTCAATAAGATCGCCATTGTCGTCGATGATCTGATCTTCGAGCAAGGTGGCAAGAAGCTGGTTCCGGTGGGTCTG

GGTGACGATGACCAGTGCATTGAGGATGATTTTGCGGCGTGGCGTGAACTGGTCTGGCCGGAACTGGATAAACTGCT

GCGTAACGAAGACGACGCTACCGTGGCAACCCCGTACAGCGCCGCTGTGCTGCAATACCGCGTGGTTTTCCACGATC

ACATTGACGGCCTGATTAGCGAAAACGGTAGCCCGAACGGTCATGCTAATGGCAATACCGTGTACGATGCGCAACAC

CCGTGCCGTAGCAACGTCGCGGTCAAGAAGGAATTGCATACTCCGGCGAGCGATCGCAGCTGCACCCACCTGGAATT

TAACATTAGCGGTACCGGCCTGATGTACGAGACGGGTGACCACGTCGGTGTGTATTGCGAGAACCTGTTGGAAACCG

TGGAGGAGGCCGAGAAGTTGTTGAACCTGAGCCCGCAGACGTACTTCTCCGTTCACACCGACAACGAGGACGGTACG

CCGTTGAGCGGCAGCAGCCTGCCGCCACCGTTTCCGCCGTGCACCTTGCGCACGGCATTGACCAAATACGCAGACTT

GACTTCTGCACCGAAAAAGTCGGTGCTGGTGGCGCTGGCCGAGTACGCATCTGACCAGGGTGAAGCGGATCGTTTGC

GTTTCTTGGCGAGCCCGAGCGGCAAAGAGGAATATGCACAGTACATCTTGGCAAGCAGCGCACGCTGCTGGAGGTC

ATGGCGGAGTTCCCGTCGGCGAAACCGCCGCTGGGTGTCTTTTTCGCGGGTGTCGCTCCGCGCCTGCAGCCGCGTTT

CTATTCCATTAGCTCTAGCCCGAAGATCGCACCGTTCCGTATTCACGTGACCTGCGCCCTGGTTTATGACAAATCCC

CTACCGGTCGCGTTCATAAGGGCATCTGTAGCACGTGGATGAAAAATGCGGTCCCGCTGGAAGAAAGCAACGATTGT

TCCTGGGCTCCGATCTTCGTCCGCAACAGCAACTTCAAGCTGCCGACCGACCCGAAGGTTCCGATTATCATGATTGG

TCCGGGTACCGGTCTGGCCCCTTTTCGTGGCTTTTTGCAAGAGCGCTTGGCGTTGAAAGAGAGCGGTGCTGAATTGG

GTCCGGCGATCTTGTTCTTTGGTTGCCGTAACCGTAAAATGGACTTTATTTACGAGGATGAACTGAATGATTTCGTC
```

-continued

```
AAAGCGGGCGTTGTCAGCGAGCTGATCGTCGCTTTTAGCCGCGAAGGCCCGATGAAAGAATACGTGCAACACAAAAT
GAGCCAACGTGCCTCCGATGTGTGGAACATCATTAGCGACGGTGGTTATGTTTATGTTTGCGGTGACGCGAAGGGTA
TGGCTCGTGATGTTCACCGTACCCTGCATACCATCGCACAGGAGCAAGGTAGCATGTCCAGCTCGGAGGCCGAAGGT
ATGGTCAAAAACCTGCAAACCACCGGTCGTTACCTGCGTGATGTGTGGTAATAA
```

CPRm amino acid sequence
SEQ ID NO: 4:

```
MEPSSQKLSPLEFVAAILKGDYSSGQVEGGPPPGLAAMLMENKDLVMVLTTSVAVLIGCVVVLAWRRAAGSGKYKQP
ELPKLVVPKAAEPEEAEDDKTKISVFFGTQTGTAEGFAKAFVEEAKARYQQARFKVIDLDDYAADDDEYEEKLKKEN
LAFFFLASYGDGEPTDNAARFYKWFTEGKDRGEWINNLQYGVFGLGNRQYEHENKIAIVVDDLIFEQGGKKLVPVGL
GDDDQCIEDDFAAWRELVWPELDKLLRNEDDATVATPYSAAVLQYRVVFHDHIDGLISENGSPNGHANGNTVYDAQH
PCRSNVAVKKELHTPASDRSCTHLEFNISGTGLMYETGDHVGVYCENLLETVEEAEKLLNLSPQTYFSVHTDNEDGT
PLSGSSLPPPFPPCTLRTALTKYADLTSAPKKSVLVALAEYASDQGEADRLRFLASPSGKEEYAQYILASQRTLLEV
MAEFPSAKPPLGVFFAGVAPRLQPRFYSISSSPKIAPFRIHVTCALVYDKSPTGRVHKGICSTWMKNAVPLEESNDC
SWAPIFVRNSNFKLPTDPKVPIIMIGPGTGLAPFRGFLQERLALKESGAELGPAILFFGCRNRKMDFIYEDELNDFV
KAGVVSELIVAFSREGPMKEYVQHKMSQRASDVWNIISDGGYVYVCGDAKGMARDVHRTLHTIAQEQGSMSSSEAEG
MVKNLQTTGRYLRDVW
```

Codon optimized cDNA encoding for SaTps8201
SEQ ID NO: 5:

```
ATGGACAGCAGCACCGCCACCGCAATGACCGCACCATTCATCGACCCGACGGATCATGTGAATCTGAAAACCGACAC
GGATGCGAGCGAAAATCGTCGTATGGGTAACTACAAGCCGAGCATTTGGAACTACGATTTTCTGCAGTCCCTGGCGA
CGCACCACAACATTGTTGAAGAGCGTCACCTGAAGCTGGCAGAGAAACTGAAAGGTCAAGTGAAATTCATGTTCGGT
GCGCCGATGGAGCCATTGGCTAAGTTGGAGCTGGTTGATGTGGTGCAACGCTTGGGTCTGAACCACCTGTTCGAGAC
TGAAATCAAAGAAGCTCTGTTCAGCATCTACAAAGATGGCAGCAATGGCTGGTGGTTTGGCCATCTGCATGCTACCT
CTTTGCGCTTCCGTCTGTTGCGCCAATGTGGCCTGTTTATCCCGCAGGACGTTTTCAAAACCTTTCAAAACAAGACC
GGTGAGTTTGACATGAAGCTGTGGGACAACGTTAAGGGCCTGCTGAGCCTGTACGAGGCGAGCTACCTGGGCTGGAA
GGGCGAGAACATCTTGGATGAAGCAAAGGCGTTCACGACCAAGTGCCTGAAGAGCGCATGGGAGAACATTAGCGAGA
AGTGGCTGGCGAAGCGTGTTAAACATGCGTTGGCGCTGCCGCTGCACTGGCGTGTTCCGCGTATTGAAGCACGCTGG
TTTATCGAGGTGTACGAACAAGAGGCCAATATGAATCCGACGCTGCTGAAACTGGCGAAACTGGACTTCAACATGGT
CCAAAGCATTCACCAGAAAGAAATCGGTGAACTGGCCCGCTGGTGGGTTACTACCGGCCTGGACAAGCTGGATTTCG
CACGCAACAATCTGTTGCAGTCTTATATGTGGAGCTGCGCCATCGCGTCCGACCCGAAATTCAAACTGGCGCGTGAA
ACCATTGTCGAGATCGGTTCCGTGTTGACGGTTGTCGACGACGGCTATGATGTGTACGGTTCTATGGATGAGCTGGA
CCTGTACACCAGCTCGGTGGAGCGTTGGTCCTGTGTCAAAATTGACAAGCTGCCTAATACGCTGAAGCTGATCTTTA
TGTCTATGTTCAACAAAACCAACGAGGTGGGTCTGCGTGTTCAACACGAGCGTGGTTACAATAGCATCCCGACCTTC
ATTAAGGCGTGGGTGGAACAGTGTAAGAGCTATCAAAAAGAGGCGCGTTGGTTTCATGGTGGTCACACGCCTCCGCT
GGAAGAATACAGCCTGAACGGTCTGGTCAGCATTGGTTTTCCGCTGTTGCTGATCACCGGCTATGTTGCGATTGCTG
AGAATGAAGCAGCCCTGGATAAAGTCCACCCGCTGCCGGACCTGCTGCATTATTCCAGCTTGCTGAGCCGTCTGATT
AATGATATCGGCACTAGCCCGGATGAAATGGCGCGTGGTGACAATCTGAAGAGCATTCACTGCTATATGAATGAAAC
CGGTGCCAGCGAAGAGGTCGCACGCGAGCACATCAAAGGCGTCATCGAAGAGAATTGGAAAATTCTGAACCAGTGTT
GCTTTGACCAGTCCCAGTTCCAGGAGCCGTTCATCACGTTTAACCTGAACAGCGTGCGCGGCTCGCATTTCTTCTAT
GAATTTGGTGATGGTTTTGGTGTTACCGACAGCTGGACCAAGGTGGATATGAAAGCGTCCTGATTGATCCGATTCC
GCTGGGTGAAGAGTAA
```

SaTps8201 amino acid sequence.
SEQ ID NO: 6:
MDSSTATAMTAPFIDPTDHVNLKTDTDASENRRMGNYKPSIWNYDFLQSLATHHNIVEERHLKLAEKLKGQVKFMFG

APMEPLAKLELVDVVQRLGLNHLFETEIKEALFSIYKDGSNGWWFGHLHATSLRFRLLRQCGLFIPQDVFKTFQNKT

GEFDMKLWDNVKGLLSLYEASYLGWKGENILDEAKAFTTKCLKSAWENISEKWLAKRVKHALALPLHWRVPRIEARW

FIEVYEQEANMNPTLLKLAKLDFNMVQSIHQKEIGELARWWVTTGLDKLDFARNNLLQSYMWSCAIASDPKFKLARE

TIVEIGSVLTVVDDGYDVYGSMDELDLYTSSVERWSCVKIDKLPNTLKLIFMSMFNKTNEVGLRVQHERGYNSIPTF

IKAWVEQCKSYQKEARWFHGGHTPPLEEYSLNGLVSIGFPLLLITGYVAIAENEAALDKVHPLPDLLHYSSLLSRLI

NDIGTSPDEMARGDNLKSIHCYMNETGASEEVAREHIKGVIEENWKILNQCCFDQSQFQEPFITFNLNSVRGSHFFY

EFGDGFGVTDSWTKVDMKSVLIDPIPLGEE synthetic operon encoding for SaCP816, CPRm and SaSAS
SEQ ID NO: 7:
CATATGGCACTGTTGTTGGCGGTTTTCTGGAGCGCTTTGATTATTCTGGTTAGCATCTTATTGCGTCGTCGTCAAAA

ACGCAACAATTTGCCACCGGGCCCACCGGCCCTGCCGATCATCGGTAACATTCACATTCTGGGCACCCTGCCGCACC

AGAGCCTGTACAATCTGGCGAAGAAGTACGGTCCGATCATGTCCATGCGTTTGGGCTTGGTTCCGGCGGTGGTCATC

AGCAGCCCGGAAGCGGCCGAGCTGGTCCTGAAAACCCACGACATCGTTTTTGCTTCTCGCCCTCGTCTGCAAGTTGC

AGATTACTTTCACTATGGCACCAAAGGCGTGATTCTGACCGAATATGGTACCTACTGGCGTAACATGCGTCGCCTGT

GCACGGTCAAACTGCTGAACACCGTTAAGATTGATAGCTTTGCAGGCACCCGCAAGAAAGAAGTCGCTAGCTTCGTT

CAGAGCCTGAAAGAAGCAAGCGTGGCGCACAAAATGGTTAACCTGTCCGCACGCGTCGCTAATGTTATTGAGAATAT

GGTTTGTCTGATGGTTATTGGTAGATCGTCTGACGAGCGTTTCAAGCTGAAAGAAGTGATCCAAGAAGCGGCACAGC

TGGCGGGTGCCTTCAATATTGGTGACTATGTCCCGTTTCTGATGCCGCTGGATCTGCAGGGCCTGACTCGCCGTATC

AAGAGCGGTAGCAAGGCATTCGATGACATCCTCGAGGTCATTATCGACGAGCATGTGCAAGACATTAAAGATCATGA

CGATGAGCAGCATGGTGACTTCATCGACGTGCTGCTGGCGATGATGAATAAGCCGATGGATTCTCGTGAGGGTCTGT

CCATCATTGATCGCACGAACATTAAAGCGATCCTGGTGGATATGATCGGTGCCGCGATGGACACGAGCACCAGCGGT

GTGGAGTGGGCGATTTCGGAGCTGATTAAGCATCCTCGTGTCATGAAGAAACTGCAAGACGAAGTGAAAACCGTAAT

CGGTATGAACCGCATGGTGGAAGAAGCGGATCTGCCGAAACTGCCGTACCTGGACATGGTTGTCAAGGAAACGATGC

GTCTGCATCCGCCAGGCCCGCTGCTGGTGCCGCGTGAAAGCATGGAAGATATTACGATCAACGGTTACTATATCCCG

AAGAAATCCCGCATTATTGTGAATGCATGGGCGATCGGCCGTGACACCAACGCCTGGAGCAATAATGCGCACGAGTT

TTTCCCTGAGCGTTTTATGAGCTCTAACGTTGATCTGCAAGGCCAGGACTTCCAGCTGATCCCGTTCGGTAGCGGTC

GTCGCGGTTGTCCGGGCATGCGTCTGGGTCTGACGACGGTCCGCTTGGTGCTGGCCCAACTGATTCACTGCTTCGAC

CTGGAGCTTCCGAAGGGCACCGTCGCGACTGACCTGGATATGAGCGAGAAGTTTGGTCTGGCAATGCCGCGTGCGCA

GCACTTACTGGCCTTTCCGACCTACCGTCTGGAGAGCTAAGTCGACTAACTTTAAGAAGGAGATATATCCATGGAAC

CTAGCTCTCAGAAACTGTCTCCGTTGGAATTTGTTGCTGCTATCCTGAAGGGCGACTACAGCAGCGGTCAGGTTGAA

GGTGGTCCACCGCCAGGTCTGGCAGCTATGTTGATGGAAAATAAGGATTTGGTGATGGTTCTGACGACGTCCGTGGC

AGTCCTGATCGGCTGTGTCGTGGTCCTGGCATGGCGTCGTGCGGCAGGTAGCGGTAAGTACAAGCAACCTGAACTGC

CTAAACTGGTGGTCCCGAAAGCAGCCGAACCGGAGGAGGCAGAGGATGATAAAACCAAGATCAGCGTGTTTTTCGGC

ACCCAAACCGGTACGGCAGAAGGTTTCGCGAAGGCTTTTGTTGAAGAGGCCAAGGCGCGTTATCAGCAGGCCCGTTT

CAAAGTTATCGACCTGGACGACTATGCGGCAGACGATGACGAGTACGAAGAGAAACTGAAGAAGGAAAACTTGGCAT

TCTTCTTCTTGGCGTCCTACGGTGACGGCGAGCCGACGGACAACGCGGCACGCTTTTACAAATGGTTTACGGAGGGT

AAGGACCGTGGTGAATGGCTGAACAATCTGCAGTACGGCGTTTTTGGTCTGGGTAACCGTCAATATGAGCATTTCAA

TAAGATCGCCATTGTCGTCGATGATCTGATCTTCGAGCAAGGTGGCAAGAAGCTGGTTCCGGTGGGTCTGGGTGACG

ATGACCAGTGCATTGAGGATGATTTTGCGGCGTGGCGTGAACTGGTCTGGCCGGAACTGGATAAACTGCTGCGTAAC

-continued

```
GAAGACGACGCTACCGTGGCAACCCCGTACAGCGCCGCTGTGCTGCAATACCGCGTGGTTTTCCACGATCACATTGA
CGGCCTGATTAGCGAAAACGGTAGCCCGAACGGTCATGCTAATGGCAATACCGTGTACGATGCGCAACACCCGTGCC
GTAGCAACGTCGCGGTCAAGAAGGAATTGCATACTCCGGCGAGCGATCGCAGCTGCACCCACCTGGAATTTAACATT
AGCGGTACCGGCCTGATGTACGAGACGGGTGACCACGTCGGTGTGTATTGCGAGAACCTGTTGGAAACCGTGGAGGA
GGCCGAGAAGTTGTTGAACCTGAGCCCGCAGACGTACTTCTCCGTTCACACCGACAACGAGGACGGTACGCCGTTGA
GCGGCAGCAGCCTGCCGCCACCGTTTCCGCCGTGCACCTTGCGCACGGCATTGACCAAATACGCAGACTTGACTTCT
GCACCGAAAAAGTCGGTGCTGGTGGCGCTGGCCGAGTACGCATCTGACCAGGGTGAAGCGGATCGTTTGCGTTTCTT
GGCGAGCCCGAGCGGCAAAGAGGAATATGCACAGTACATCTTGGCAAGCCAGCGCACGCTGCTGGAGGTCATGGCGG
AGTTCCCGTCGGCGAAACCGCCGCTGGGTGTCTTTTTCGCGGGTGTCGCTCCGCGCCTGCAGCCGCGTTTCTATTCC
ATTAGCTCTAGCCCGAAGATCGCACCGTTCCGTATTCACGTGACCTGCGCCCTGGTTTATGACAAATCCCCTACCGG
TCGCGTTCATAAGGGCATCTGTAGCACGTGGATGAAAAATGCGGTCCCGCTGGAAGAAAGCAACGATTGTTCCTGGG
CTCCGATCTTCGTCCGCAACAGCAACTTCAAGCTGCCGACCGACCCGAAGGTTCCGATTATCATGATTGGTCCGGGT
ACCGGTCTGGCCCCTTTTCGTGGCTTTTTGCAAGAGCGCTTGGCGTTGAAAGAGAGCGGTGCTGAATTGGGTCCGGC
GATCTTGTTCTTTGGTTGCCGTAACCGTAAAATGGACTTTATTTACGAGGATGAACTGAATGATTTCGTCAAAGCGG
GCGTTGTCAGCGAGCTGATCGTCGCTTTTAGCCGCGAAGGCCCGATGAAAGAATACGTGCAACACAAAATGAGCCAA
CGTGCCTCCGATGTGTGGAACATCATTAGCGACGGTGGTTATGTTTATGTTTGCGGTGACGCGAAGGGTATGGCTCG
TGATGTTCACCGTACCCTGCATACCATCGCACAGGAGCAAGGTAGCATGTCCAGCTCGGAGGCCGAAGGTATGGTCA
AAAACCTGCAAACCACCGGTCGTTACCTGCGTGATGTGTGGTAATAAAAGCTTAGGAGGTAAAACATATGGACAGCA
GCACCGCCACCGCAATGACCGCACCATTCATCGACCCGACGGATCATGTGAATCTGAAAACCGACACGGATGCGAGC
GAAAATCGTCGTATGGGTAACTACAAGCCGAGCATTTGGAACTACGATTTTCTGCAGTCCCTGGCGACGCACCACAA
CATTGTTGAAGAGCGTCACCTGAAGCTGGCAGAGAAACTGAAAGGTCAAGTGAAATTCATGTTCGGTGCGCCGATGG
AGCCATTGGCTAAGTTGGAGCTGGTTGATGTGGTGCAACGCTTGGGTCTGAACCACCTGTTCGAGACTGAAATCAAA
GAAGCTCTGTTCAGCATCTACAAAGATGGCAGCAATGGCTGGTGGTTTGGCCATCTGCATGCTACCTCTTTGCGCTT
CCGTCTGTTGCGCCAATGTGGCCTGTTTATCCCGCAGGACGTTTTCAAAACCTTTCAAAACAAGACCGGTGAGTTTG
ACATGAAGCTGTGGGACAACGTTAAGGGCCTGCTGAGCCTGTACGAGGCGAGCTACCTGGGCTGGAAGGGCGAGAAC
ATCTTGGATGAAGCAAAGGCGTTCACGACCAAGTGCCTGAAGAGCGCATGGGAGAACATTAGCGAGAAGTGGCTGGC
GAAGCGTGTTAAACATGCGTTGGCGCTGCCGCTGCACTGGCGTGTTCCGCGTATTGAAGCACGCTGGTTTATCGAGG
TGTACGAACAAGAGGCCAATATGAATCCGACGCTGCTGAAACTGGCGAAACTGGACTTCAACATGGTCCAAAGCATT
CACCAGAAAGAAATCGGTGAACTGGCCCGCTGGTGGGTTACTACCGGCCTGGACAAGCTGGATTTCGCACGCAACAA
TCTGTTGCAGTCTTATATGTGGAGCTGCGCCATCGCGTCCGACCCGAAATTCAAACTGGCGCGTGAAACCATTGTCG
AGATCGGTTCCGTGTTGACGGTTGTCGACGACGGCTATGATGTGTACGGTTCTATGGATGAGCTGGACCTGTACACC
AGCTCGGTGGAGCGTTGGTCCTGTGTCAAAATTGACAAGCTGCCTAATACGCTGAAGCTGATCTTTATGTCTATGTT
CAACAAAACCAACGAGGTGGGTCTGCGTGTTCAACACGAGCGTGGTTACAATAGCATCCCGACCTTCATTAAGGCGT
GGGTGGAACAGTGTAAGAGCTATCAAAAAGAGGCGCGTTGGTTTCATGGTGGTCACACGCCTCCGCTGGAAGAATAC
AGCCTGAACGGTCTGGTCAGCATTGGTTTTCCGCTGTTGCTGATCACCGGCTATGTTGCGATTGCTGAGAATGAAGC
AGCCCTGGATAAAGTCCACCCGCTGCCGGACCTGCTGCATTATTCCAGCTTGCTGAGCCGTCTGATTAATGATATCG
GCACTAGCCCGGATGAAATGGCGCGTGGTGACAATCTGAAGAGCATTCACTGCTATATGAATGAAACCGGTGCCAGC
GAAGAGGTCGCACGCGAGCACATCAAAGGCGTCATCGAAGAGAATTGGAAAATTCTGAACCAGTGTTGCTTTGACCA
GTCCCAGTTCCAGGAGCCGTTCATCACGTTTAACCTGAACAGCGTGCGCGGCTCGCATTTCTTCTATGAATTTGGTG
ATGGTTTTGGTGTTACCGACAGCTGGACCAAGGTGGATATGAAAAGCGTCCTGATTGATCCGATTCCGCTGGGTGAA
GAGTAAGCTTGC
```

The invention claimed is:

1. A sandalwood oil comprising at least 85% santalol and bergamotol and 1% or less cis-lanceol, wherein the oil has one or more of the following features:
   i) 5% or less alpha-santalal;
   ii) 5% or less farnesol; and
   iii) 0.5% or less spirosantalol;
   wherein the sandalwood oil is not prepared from the sandalwood tree.

2. The sandalwood oil of claim 1, wherein the at least 85% santalol and bergamotol comprises 37-65% alpha-santalol, 13-37% beta-santalol and 1 to 35% bergamotol.

3. The sandalwood oil of claim 1, wherein a ratio of cis-alpha-santalol to trans-alpha-santalol is 90:1 or less.

4. The sandalwood oil of claim 1, wherein the alpha-santalal is 90% or more trans-alpha-santalal.

5. The sandalwood oil of claim 1, wherein the oil comprises 0-1% cis-beta-sinensol.

6. The sandalwood oil of claim 1, comprising:
   i) 50-60% alpha-santalol;
   ii) 20-35% beta-santalol;
   iii) 5% or less alpha-santalal;
   iv) 5% or less farnesol;
   v) 0.5% or less spirosantalol;
   vi) 4-10% bergamotol;
   vii) 0-5% cis-beta-sinensol; and
   viii) 5% or less epi-beta-santalol.

7. The sandalwood oil of claim 1, comprising:
   i) 54%-59% alpha-santalol;
   ii) 25.1%-30% beta-santalol;
   iii) 0.7%-3% alpha-santalal;
   iv) 1%-2.3% farnesol;
   v) 0.5% or less spirosantalol;
   vi) 6.3%-7.2% bergamotol;
   vii) 0.6%-1.4% cis-beta-sinensol; and
   viii) 1%-2% epi-beta-santalol.

8. The sandalwood oil of claim 1, wherein the oil is microbially produced.

9. A method of preparing the sandalwood oil of claim 1, the method comprising: (i) cultivating a genetically engineered organism capable of producing FPP and which expresses a suitable sesquiterpene synthase, cytochrome P450 and CPR, and (ii) isolating the sandalwood oil.

10. The sandalwood oil of claim 1, wherein the oil is encapsulated within a matrix material.

11. A perfuming composition comprising:
i) the sandalwood oil of claim 1,
ii) at least one ingredient selected from the group consisting of a perfumery carrier and a perfumery base; and
iii) optionally at least one perfumery adjuvant.

12. A perfumed consumer product comprising the sandalwood oil of claim 1.

13. The perfumed consumer product according to claim 12, wherein the perfumed consumer product is a perfume, a fabric care product, a body-care product, a cosmetic preparation, a skin-care product, an air care product, a home care product, a fine perfume, a splash perfume, an eau de perfume, a cologne, a shave lotion, an after-shave lotion, a liquid detergent, a solid detergent, a fabric softener, a fabric refresher, an ironing water, a paper, a bleach, a carpet cleaner, curtain-care products, a shampoo, a coloring preparation, a color care product, a hair shaping product, a dental care product, a disinfectant, an intimate care product, a hair spray, a vanishing cream, a deodorant, an antiperspirant, hair remover, tanning product, sun product, nail products, skin cleansing products, a makeup, a perfumed soap, shower mousse, bath mousse, oil, gel, foot/hand care products, a hygiene product, an air freshener, a "ready to use" powdered air freshener, a mold remover, furnisher care, a wipe, a dish detergent, a hard-surface detergent, a leather care product, or a car care product.

14. An arthropod control composition comprising the sandalwood oil of claim 1.

15. A method of using the sandalwood oil of claim 1, the method comprising using the sandalwood oil for treatment of a microbial infection, an inflammatory condition and/or to increase skin moisturizing, or for treatment of acne, eczema, psoriasis, seborrheic or atopic dermatitis.

16. A perfumed consumer product comprising the perfuming composition according 11.

17. The perfumed consumer product according to claim 16, wherein the perfumed consumer product is a perfume, a fabric care product, a body-care product, a cosmetic preparation, a skin-care product, an air care product, a home care product, a fine perfume, a splash perfume, an eau de perfume, a cologne, a shave lotion, an after-shave lotion, a liquid detergent, a solid detergent, a fabric softener, a fabric refresher, an ironing water, a paper, a bleach, a carpet cleaner, curtain-care products, a shampoo, a coloring preparation, a color care product, a hair shaping product, a dental care product, a disinfectant, an intimate care product, a hair spray, a vanishing cream, a deodorant, an antiperspirant, hair remover, tanning product, sun product, nail products, skin cleansing products, a makeup, a perfumed soap, shower mousse, bath mousse, oil, gel, foot/hand care products, a hygiene product, an air freshener, a "ready to use" powdered air freshener, a mold remover, furnisher care, a wipe, a dish detergent, a hard-surface detergent, a leather care product, or a car care product.

* * * * *